United States Patent
Josephsen et al.

(10) Patent No.: US 6,300,109 B1
(45) Date of Patent: *Oct. 9, 2001

(54) **PLASMID-DERIVED LLAD II RESTRICTION-MODIFICATION SYSTEM FROM *LACTOCOCCUS LACTIS***

(76) Inventors: Jytte Josephsen, Magnoliavej 34; Finn Kvist Vogensen, Nordre Fasanvej 28, both of Fredericksberg DK-2000; Annette Madsen, Apartment 605 Thyrasgade 4, Copenhagen N. DK-2200, all of (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,159
(22) PCT Filed: Feb. 19, 1996
(86) PCT No.: PCT/DK96/00076
§ 371 Date: Dec. 19, 1997
§ 102(e) Date: Dec. 19, 1997
(87) PCT Pub. No.: WO96/25503
PCT Pub. Date: Aug. 22, 1996

(30) Foreign Application Priority Data

Feb. 17, 1995 (DK) .................................. 0179/95

(51) Int. Cl.$^7$ .............................. C12N 9/10; C12N 9/22; C12N 15/54; C12N 15/55
(52) U.S. Cl. ...................... 435/193; 435/199; 435/320.1; 435/236; 435/252.3; 536/23.2
(58) Field of Search ...................................... 435/199, 193, 435/320, 1, 236, 252.3; 536/23.2

(56) References Cited

PUBLICATIONS

Andresen, A.A., Geis, U. Krusch, and M. Teuber. Plasmidmuster milchwirtschaftlich genutzter Starterkulturen. Milchwissenschaft 39 (1984): 140–143.
Bickle, T.A. and Krüger, D.H.: Biology of DNA restriction Microbiol. Rev. 57 (1993): 434–450.
Boyer, H.W., and Roulland–Dussoix, D.: A complementation analysis of the restriction and modification of DNA in *Escherichia coli*. J. Mol. Biol. 41 (1969): 459.
Cerritelli, S., S.S. Springhorn, and S.A. Lacks: DpnA, a methylase for single–strand DNA in the DpuII restriction system, and its biological function. Proc. Natl. Acad. Sci. USA 86 (1989): 9223–9227.
Chopin, A.., Chopin, M.–C., Moillo–Batt, A. and Langella, P.: Two plasmid–determined restriction and modification systems in *Streptococcus lactis*. Plasmid 11 (1984): 260–263.

Daly, C. and Fitzgerald, G.F.: Mechanisms of bacteriophage insensitivity in the lactic streptococci. In: Ferretti, J.J. and Curtis III, R. (Eds.), Streptococcus Genetics. American Society for Microbiology, Washington, D.C., 1987, pp. 259–268.
Dao, M.L. and Ferretti, J.J.: *Streptococcus–Escherichia coli* shuttle vector pSA3 and its use in the cloning of streptococcal genes. Appl. Environ. Microbiol. 49 (1985): 115–119.
Davis, R., van der Lelie, D., Mercenier, A., Daly, C. and Fitzgerald, G.F.: ScrFI restriction–modification system of *Lactococcus lactis* subsp. *cremoris* UC503: cloning and characterization of two ScrFI Mtase genes. Appl. Environ. Microbiol. 59 (1993): 777–785.
de la Campa, A.G., Kale, P., Springhorn, S.S. and Lacks, S.A.: Proteins encoded by the DpnII restriction gene cassette. Two methylases and an endonuclease. J. Mol. Biol. 196 (1987): 457–469.
Devereux, J., P. Haeberli and O. Smithies: A comprehensive set of sequence analysis programs for the VAX. Nucl. Acids Res. 12 (1984): 387–395.
Fitzgerald, G.F., Daly, C., Brown, L.R. and Gingeras, T.R.: ScrFI, a new sequence–specific Enase from *Streptococcus cremoris*. Nucleic Acids Res. 10 (1982): 8171–8179.
Gasson, M.J.: Plasmid complements of *Streptococcus lactis* NCDO 712 and other lactic streptocci after prptoplast–induced curing. J. Bacteriol. 154 (1983): 1–9.
Gautier, M., and Chopin, M.–C.: Plasmid–determined systems for restriction and modification activity and abortive infection in *Streptococcus cremoris*. Appl. Environ. Microbiol. 53 (1987): 923–927.
Gordon, J.–J. Delome, C., Ehrlich, S.D., and Renault, P.: Divergence of genome sequences between *Lactococcus lactis* subsp. *lactis* and *Lactococcus lactis* subsp. *cremoris*. Appl. Environ. Microbiol. 58 (1992): 4045–4047.
Hayes, F., Daly, C., and Fitzgerald, G.F.: Identification of the minimal replicon of *Lactococcus lactis* subsp. *lactis* UC317 plasmid pCI305. Appl. Environ. Microbiol. 56 (1990): 202–209.

(List continued on next page.)

Primary Examiner—Charles L. Patterson, Jr.
(74) Attorney, Agent, or Firm—Darby & Darby

(57) ABSTRACT

A number of type II restriction-modification (R-M) systems have been derived from plasmids found in *Lactococcus lactis* strains from the Danish starter culture TK5. The R-M systems LlaAI, LlaBI and LlaDII are claimed with their nucleotide sequences containing open reading frames (ORFs) coding for restriction endonucleases and corresponding methylases. Also a DNA cassette comprising one or more of the R-M systems and fragments thereof in combination with DNA encoding other phage resistance mechanisms is claimed as are cloning and expression vectors including DNA selected from the group consisting of the R-M systems, fragments thereof and DNA cassette, cells transformed with the expression vectors, a method of conferring increased virus resistance on a cell, and the individual restriction endonucleases and methylases of the R-M systems.

36 Claims, 4 Drawing Sheets

OTHER PUBLICATIONS

Higgins, D.L., Sanozky–Dawes, R.B. and Klaenhammer, T.R.: Restriction and modification activities from *Streptococcus lactis* ME2 are encoded by a self–transmissible plasmid, pTN20, that forms cointegrates during mobilization of lactose–fermenting ability. J. Bacteriol. 170 (1988): 3435–3442.

Hill, C., Pierce, K. and Klaenhammer, T.R.: The conjugative plasmid pTR2030 encodes two bacteriophage defense mechanisms in lactococci, restriction modification (R+/M+) and abortive infections (Hsp+). Appl. Environ. Microbiol. 55 (1989): 2416–1419.

Hill, C., Miller, L.A. and Klaenhammer, T.R.: In vivo genetic exchange of a functional domain from a type II A methylase between lactococcal plasmid pTR2030 and a virulent bacteriophage. J. Bacteriol. 173 (1991): 4363–4370.

Holo, H. and Nes, I.F.: High–frequency transformation, by electroporation, of *Lactococcus lactis* subsp. *cremoris* grown with glycine in osmotically stabilized media. Appln. Environ. Microbiol. 55 (1989): 3119–3123.

Janulaitis, A., Petrusyte, M., Maneliene, Z., Klimasauskas, S. and Butkus, V.: Purification and properties of the Eco571 restriction endonuclease and methylase–prototypes of a new class (type IV). Nucleic Acids Res. 20 (1992): 6043–6049.

Janulaitis, A., Vaisvila, R., Timinskas, A., Klimasauskas, S., and Butkus, V.: Cloning and sequence analysis of the gene coding for Eco571 type IV restriction–modification enzymes. Nucleic Acids Res. 20 (1992): 6051–6056.

Josephsen, J. and Nielsen, E.W.: Plasmid profiles and bacteriophage sensitivity of bacteria of a Cheddar starter used for five years without rotation. Milchwissenschaft 43 (1988): 219–223.

Josephsen, J. and Vogensen, F.K.: Identification of three different plasmid encoded restriction/modification systems in *Streptococcus lactis* subsp. *cremoris* W56. FEMS Microbiol. Lett. 59 (1989): 161–166.

Josephsen, J. and Klaenhammer, T.R.: Stacking of three different restriction and modification systems in *Lactococcus lactis* by cotransformation. Plasmid 23 (1990): 71–75.

Keogh, B.P. and Shimmin, P.D.: Morphology of the bacteriophages of lactic streptococcal bacteriophages. Appl. Microbiol. 27 (1974): 411–415.

Klaenhammer, J.R.: Plasmid–directed mechanisms for bacteriophage defense in lactic streptococci. FEMS Microbiol. Rev. 46 (1987): 313–325.

Klaenhammer, T.R. and Fitzgerald, G.F.: Bacteriophages and bacteriophage resistance. In: M.G. Gasson and W.M. de Vos (Eds.), Genetics and Biotechnology of Lactic Acid Bacteria. Blackie, London, 1994, pp. 106–168.

Lacks, S.A., Mannarelli, B.M., Springhorn, S.S., and Greenberg, B.: Genetic basis of the complementary Dpnl and Dpnll restriction systems of *S. pneumoniae*: An intercellular cassette mechanism. Cell 46 (1986): 993–1000.

Lauster, R.: Evolution of Type II DNA Methytransferases, J. Mol. Biol., 206 (1989): 313–321.

Lauster, R.: Trauter, T.A. and Noyer–Weidner, M.,: Cytosine–specific Type II DNA Methyltransferases. A conserved enzyme core with variable target–recognizing domains. J. Molecular Biology 206 (1989): 305–312.

Lubys, A., and Janulaitis, A.: Cloning and analysis of the plasmid–borne genes encoding the Bsp61 restriction and modification enzymes. Gene 157 (1995): 25–29.

Mayo, B., C. Hardisson and A.F. Brana. Nucleolytic activities in *Lactococcus lactis* subsp. *lactis* NCDO 497. FEMS Microbiol. Lett. 79 (1991): 195–198.

Nielsen, E. Waagner, Josephsen, J. and Vogensen, F.K.: Lactic starters–improvement of bacteriophage resistance and application of DNA–technology. Danish J. Agro. Special Issue Mar. 1987, 35–45.

Nyengaard, N., Vogensen, F.K. and Josephsen, J.: LlaAl and LlaBl, two type–II restriction endonucleases from *Lactococcus lactis* subsp. *cremoris* W9 and W56 recognizing, respectively, 5'–/GATC–3 and 5'–C/TRYAG–3'. Gene 136 (1993): 371–372.

Pósfai, J., Bhagwat, S.A., Pósfai, G., and Roberts, R.J.: Predictive motifs derived from cytosine methyltransferases. Nucleic. Acids Res. 17 (1989): 2421–2435.

Roberts, R.J.: Restriction enzymes and their isochizomers. Nucleic Acids Res. 18 (1990): 2331–2365.

Sanders, M.A.: Phage resistance in lactic acid bacteria. Biochimie 70 (1988): 411–421.

Sanger, F., S. Nickelsen and A.R. Coulson: DNA sequencing with chain terminating inhibitors. Proc. Natl. Acad. Sci. 74 (1977), 5463–5467.

Schleifer, K.H., Kraus, J., Dvorak, C., Kilpper–Bälz, R., Collins, M.D., Fischer, W., Transfer of *Streptococcus lactis* and related streptococci to the genus Lactococcus gen. nov. System. Appl. Microbiol. 6 (1985): 183–195.

Sing. W.D. and Klaenhammer, T.R.: Characterization of restriction–modification plasmids from *Lactococcus lactis* ssp. *cremoris* and their effect when combined with pTR2030.J. Dairy Sci. 74 (1991): 1133–1144.

Sing, W.D. and Klaenhammer, T.R.: A strategy for rotation of different bacterioplhage defenses in a lactococca single–strain starter culture system. Appl. Environ. Microbiol. 59 (1993): 365–372.

Tao, T., and Blumenthal, R.M.: Sequence and characterization of pvuIIR, the PvuII endonuclease gene, and of pvuIIC, its regulatory gene. J. Bacteriol. 174 (1992): 3395–3398.

Terzaghi, B.E., and W.E. Sandine. Improved medium for lactic streptococci and their bacteriophages. Appl. Microbiol. 29 (1975): 807–813.

Twomey, D.P., Davis, R., Daly, C., and Fitzgerald, G.F.: Sequence of the gene encoding a second ScrFl $m^5C$ methyltransferase of *Lactococcus lactis*. Gene 136 (1993): 205–209.

Tynkkynen, S., Buist, G., Kunji, E., Kok, J., Poolman, B., Venema, G., and Haandrikman, A.J.: Genetic and biochemical characterization of the oligopeptide transport system of *Lactococcus lactis*. J. Bacteriol. 175 (1993): 7523–7532.

Ueno, T., Ito, H., Kimizuka, F., Kotani, H. and Nakajima, K.: Gene structure and expression of the Mbol restriction—modification system, Nucleic Acids Research 21 (1993): 2309–2313.

Walsh, P.M., and McKay: Recombinant plasmid associated with cell aggregation and high frequency conjugation of *Streptococcus lactis* ML3. J. Bacteriol. 146 (1981): 937–944.

Wilson, G.C.: Organization of restriction–modification systems. Nucleic Acids Res. 19 (1991): 2539–2566.

Wilson, G.G.: Amino acid sequence arrangements of DNA–methltransferases. Methods in Enzymology 216 (1992): 259–279.

Wilson, G.G. and Murray, N.E.: Restriction and Modification system, Ann. Rev. Genet 25 (1991): 585–627.

Withers, B.E., Ambroso, L.A. and Dunbar, J.C.: Structure and evolution of the XcyI restriction–modification system, Nucleic Acids Research 20 (1992): 6267–6273.

von Wright, A., Tynkkynen, S. and Suominen, M.: Cloning of a *Streptococcus lactis* subsp. *lactis* chromosomal fragment associated with the ability to grow in milk. Appl. Environ. Microbiol. 53 (1987): 1584–1588.

Chopin, et al., GIM 90 (Pt. I, 467–76)(1990).

Moineau, et al., Applied and Enviromental Microbiology, 1995, 61(6):2193–2202.

Nyengaard, et al., Gene, 1995, 157:13–18.

O'Sullivan, et al., Journal of Bacteriology, 1995, 177(1):134–143.

PLASMID-DERIVED LLAD II RESTRICTION-MODIFICATION SYSTEM FROM *LACTOCOCCUS LACTIS*

This invention relates to plasmid-derived type II restriction-modification (R-M) systems from *Lactococcus lactis*, DNA fragments coding for individual methylases and restriction endonucleases thereof, DNA cassettes for increasing phage resistance in lactic acid bacteria, cloning and expression vectors including the R-M systems, a method of conferring increased phage resistance on a lactic acid bacterium, lactic acid bacteria and *Lactococcus lactis* strains carrying the expression vectors, as well as methylases and restriction endonucleases encoded by the R-M systems.

BACKGROUND OF THE INVENTION

Lactococcus strains are used as starter cultures for the production of cheeses and fermented milks. Bacteriophage infection of the starter culture remains a serious problem for the cheese industry and can result in a slow or dead cheese vat. Several mechanisms of phage defense have been identified in lactococci. These include adsorption blocking, abortive infection, and R-M systems (26). A report has shown the beneficial effect of using different phage resistance mechanisms in rotation (42). By cloning phage resistance mechanisms from lactococci it would be possible to construct a "cassette" like system consisting of different phage resistance mechanisms.

Restriction-modification (R-M) systems have been found in a wide range of bacteria. At least three different types of R-M systems, type I, II and III, have been found and characterized with respect to their requirement of $Mg^{2+}$, ATP and S-adenosyl-methionine (2). The type II R-M system is by far the most simple and best understood of the R-M systems, containing a separate methylase (MTase) which uses S-adenosyl-methionine as the methyl donor and an endonuclease (ENase), both recognizing the same sequence. Today more than 200 different type II R-M systems have been identified and more than 100 of them have been cloned, mainly because of their importance as tools in molecular biology and the important knowledge which is achieved of protein-DNA interactions. The genetic characterization of type II R-M systems shows that the genes for the ENase and the MTase are closely located, although not always in the same orientation. The MTase and the ENase from the same type II R-M system normally do not show any homology to each other at the amino acid level despite the fact that they recognize the same DNA-sequence. Comparisons between type II MTases have shown that strong similarities exist within the group consisting of 5-methylcytosine MTases ($m^5C$ MTases) and within the group consisting of N4-methylcytosine ($m^4C$) and N6-methyladenosine ($m^6A$) MTases (29). The $m^5C$ MTases have about ten common amino acid sequence motifs, whereas the $m^4C$ and $m^6A$ MTases share two major common amino acid sequence motifs. In contrast, the ENases have generally very little homology in common, and no strong sequence motifs have been found.

Several plasmids encoding R-M systems have been found in lactococci. However they have not been characterized at the molecular level, but only in vivo by their efficiency in restricting phages (38). Fitzgerald et al. (11) examined eight different strains and found only one type II endonuclease activity, R, ScrFI, in one strain, *L. lactis* UC503 (originally designated *Streptococcus cremoris* F). This first type II R-M system, ScrFI, isolated and characterized from a *L. lactis* strain, has been found to be chromosomally encoded (11, 8). Later Daly and Fitzgerald (6) examined seven strains more from different starter cultures and found that six of the strains had ENase activity similar to R, ScrFI. No other type II ENase activities were found. The ENase from ScrFI recognized 5'-CC↓NGG-3'. Two ScrFI MTase-encoding genes have been cloned and characterized, but neither of the two isolated M,ScrFI-carrying clones exhibited any ScrFI ENase activity (8). The nucleotide sequences of the two MTase-encoding genes have been determined (8, 45). Both contained all ten of the predictive motifs normally found in $m^5C$ MTases. Mayo et al. (32) have reported type II activity, LlaI recognizing the sequence CC↓WGG from *L. lactis* NCDO497, but they did not determine whether it was chromosomally or plasmid encoded.

A type IIS system, LlaI, has been identified on the lactococcal plasmid pTR2030, which also codes for an abortive infection mechanism (17). The nucleotide sequence of a type IIS MTase, M,LlaI, from the plasmid pTR2030 has been identified and determined (18).

TK5 is a Danish starter culture, which has been used for the production of Cheddar cheese since 1982 (33). This starter culture has a marked resistance to phages as the dairy during 11 years of continuous production did not observe any delay in acidification due to a phage infection, even though phages were isolated from the whey. The starter originates from an old traditional dairy starter culture, which consists of an unknown number of *L. lactis* strains. Sixty-two bacterial isolates were purified from the TK5 starter. 33 of the isolates were arranged according to their plasmid profiles into six groups of identical or nearly identical profiles; 27 of the isolates showed unique plasmid profiles (22). All isolates have between 5 and 10 plasmids.

In order to identify plasmid-encoded phage resistance in Lactococcus a cotransformation procedure was used. Total plasmid DNA from *L. lactis* strain W56 isolated from the TK5 starter culture (33) was transformed together with the vector pVS2 (53) into *Lactococcus lactis* subsp. *cremoris* MG1614. We selected for the $Cm^R$ marker on pVS2. Transformants were tested for increased phage resistance. In this way we identified three plasmids (pJW563, pJW565, and pJW566) which coded for R-M systems in W56 (23). These plasmids ranged in size from 11 to 25 kb. The efficiency of plating (EOP) for the isometric-headed phage p2 (16) varied from $10^{-2}$ to $10^{-3}$ for different plasmids. The existence of multiple R-M encoding plasmids in Lactococci's strains has previously been reported by Chopin's group in France (5, 13).

That multiple R-M-encoding plasmids can increase phage resistance was confirmed by stacking two-three plasmids (23, 24). The data in the following Table A show the efficiency of plating (EOP) of phage p2 on the various transformants, the numbers in parentheses in column 2 show the EOP of phage p2 with the R-M plasmid alone in *L. lactis* MG1614.

TABLE A

Plasmid encoding R-M systems assembled in *L. lactis* and their effects on the EOP of phage p2 or jj50[a].

| Transformants[b] | Plasmid encoding R-M | EOP |
|---|---|---|
| MG1614 | none | 1 |
| T128 | pJW563 ($10^{-3}$) + pJW565 ($10^{-2}$) | $10^{-5}$ |
| T46 | pJW563 ($10^{-3}$) + pJW566 (2 × $10^{-2}$) | 4 × $10^{-6}$ |
| T45 | pJW565 ($10^{-2}$) + pJW566 (2 × $10^{-2}$) | $10^{-3}$ |
| T8 | pJW563 ($10^{-3}$) + pJW565 ($10^{-2}$) + pJW566 (2 × $10^{-2}$) | 3 × $10^{-6}$ |
| J96 | pJW563 ($10^{-3}$) + pFV1001 ($10^{-1}$) | $10^{-5}$ |
| J92 | pJW563 ($10^{-3}$) + pFV1201 ($10^{-1}$) | $10^{-5}$ |

TABLE A-continued

Plasmid encoding R-M systems assembled in *L. lactis* and their effects on the EOP of phage p2 or jj50[a].

| Transformants[b] | Plasmid encoding R-M | EOP |
|---|---|---|
| J75 | pJW563 ($10^{-3}$) + pFV1001 ($10^{-1}$) + pTRK12 ($10^{-1}$) | $4 \times 10^{-7}$ |

[a]Phages p2 and jj50 were propagated on *L. lactis* MG1614[pVS2]. *L. lactis* MG1614 is a sm$^R$, Opp$^d$ derivative of *L. lactis* MG1363 (46).
[b]All transformants also harbored pVS2.

As shown in Table A, the effect of assembling R-M plasmids were additive in most cases. This supports the importance of R-M systems in the phage resistance of the TK5 starter. We did not obtain completely phage resistant strains, however, Sing and Klaenhammer (41) showed that in combination with other phage resistance mechanisms, e.g., abortive infection, R-M systems are powerful tools.

Transformant T1.1 (*L. lacits* MG1614+pJW563) and a transformant harbouring a plasmid pFW094 from *L. lactis* W9 (34) exhibited type II endonuclease activity showing that type II R-M systems can be plasmid encoded in *Lactococcus lactis*.

The ENases R.LlaAI and R.LlaBI from W9 and W56, respectively, were partially purified; and the recognition sequences for both ENases were identified by digesting well known DNA (pBR322/328, λ DNA) with the respective ENases, treating the fragments with either the Klenow fragment of DNA polymerase or mung bean nuclease and ligating the resulting fragments into pBluescriptIISK+ (Stratagene, La Jolla, Calif., USA) digested with EcoRV. By sequencing the junction fragments of the obtained clones, the recognition sequence of the respective ENases could be determined (34).

We found that R.LlaAI and R.LlaBI recognized 5'-↓GATC-3' and 5'-C↓TRYAG-3', respectively, digesting as indicated by the arrows. ENase R.LlaAI is therefore an isoschizomer of MboI from *Moraxella bovis* and DpnII from *Streptococcus pneumoniae*. R.LlaBI is an isoschizomer of SfcI from *Enterococcus faecium*. Identical ENase cleavage patterns were obtained in digests of pBluescriptIISK+, pBR322 and M13mp20 with R.LlaAI and MboI, and with R.LlaBI and SfcI, respectively.

SUMMARY OF THE INVENTION

Attempts to clone LlaAI or LlaBI in *Escherichia coli* by screening the transformants for increased phage resistance to λvir were unsuccessful. However, it was possible to clone and subclone the LlaAI, LlaBI and LlaDII R-M systems directly in Lactococcus (see the following examples). When fragments from LlaAI and LlaDII were later transferred to *E. coli*, only the MTase activity was expressed, while ENase activity could not be detected. It was not possible to clone the entire LlaBI system or the gene encoding the methylase in *E. coli*.

From the nucleotide sequence of LlaAI we could identify three ORFs, transcribed in the same direction and coding for putative proteins of 284, 269 (or 257) and 304 amino acids. By comparison of the deduced amino acid sequences with data in EMBL and GenBank we found that two of the proteins had about 80% homology to the two MTases from the DpnII R-M system, while the third had about 30% homology to the corresponding ENase. This indicates that the LlaAI R-M system consisted of two putative MTases and one putative ENase. Based on the observation that the two ENases, R.LlaAI and DpnII, recognize the same nucleotide sequence, 5'-GATC-3', that both have two MTases, that the two MTases of DpnII methylate adenine (9), and that the LlaAI ENase is sensitive to methylated DNA from dam$^+$ *E. coli* strain, we conclude that the LlaAI MTases most probably methylate adenine. It has been suggested that the previously sequenced lactococcal MTases, M,LlaI and M,ScrFI, methylate adenine and cytosine, respectively (18, 8).

From the nucleotide sequence of LlaBI we could identify two ORFs with predicted proteins of 580 and 299 amino acids. They are transcribed divergently. We did not find any very strong homology to other ENases or MTases in the EMBL and GenBank.

Accordingly, in a first aspect the present invention provides a plasmid-derived type II restriction-modification (R-M) system, termed LlaAI, from *Lactococcus lactis* subsp. *cremoris* W9, said system encoding at least one methylase and a restriction endonuclease with the recognition sequence 5'-↓GATC-3', characterized in that the system comprises i) an open reading frame, termed ORF1, from nucleotide 769 to nucleotide 1620 in the enclosed SEQ ID No. 1, coding for a methylase, termed M.LlaAIA, having the amino acid sequence shown in the enclosed SEQ ID No. 2;

ii) an open reading frame, termed ORF2, from nucleotide 1613 to nucleotide 2419 in the enclosed SEQ ID No. 3 (same as SEQ ID No. 1) or from nucleotide 1649 to nucleotide 2419 in the enclosed SEQ ID No. 5 (same as SEQ ID No. 1), coding for a methylase, termed M.LlaAIB, having the amino acid sequence shown in the enclosed SEQ ID No. 4 or SEQ ID No. 6, respectively; and iii) an open reading frame, termed ORF3, from nucleotide 2412 to nucleotide 3323 in the enclosed SEQ ID No.7 (same as SEQ ID No. 1), coding for a restriction endonuclease, termed R.LlaAI, having the amino acid sequence shown in the enclosed SEQ ID No. 8.

This aspect of the invention also includes DNA fragments comprising each of the ORFs in the R-M system LlaAI, i.e.

a) A DNA fragment coding for a methylase, termed M.LlaAIA, said fragment comprising the DNA sequence from nucleotide 769 to nucleotide 1620 in the enclosed SEQ ID No. 1.

b) A DNA fragment coding for a methylase, termed M.LlaAIB, said fragment comprising the DNA sequence from nucleotide 1613 to nucleotide 2419 or from nucleotide 1649 to nucleotide 2419 in the enclosed SEQ ID No. 1.

c) A DNA fragment coding for a restriction endonuclease, termed R.LlaAI, said fragment comprising the DNA sequence from nucleotide 2412 to nucleotide 3323 in the enclosed SEQ ID No. 1.

In a second aspect the present invention provides a plasmid-derived type II restriction-modification (R-M) system, termed LlaBI, from *Lactococcus lactis* subsp. *cremoris* W56, said system encoding at least one methylase and a restriction endonuclease with the recognition sequence 5'-C↓TRYAG-3', characterized in that the system comprises i) an open reading frame, termed ORF1, from nucleotide 422 to nucleotide 2161 in the enclosed SEQ ID No. 9, coding in the complementary strand for a methylase, termed M.LlaBI, having the amino acid sequence shown in the enclosed SEQ ID No. 10; and ii) an open reading frame, termed ORF2, from nucleotide 2464 to nucleotide 3360 in the enclosed SEQ ID No. 9, coding for a restriction endonuclease, termed R.LlaBI, having the amino acid sequence shown in the enclosed SEQ ID No. 11.

This aspect of the invention also includes DNA fragments comprising each of the ORFs in the R-M system LlaBI, i.e.

d) A DNA fragment coding in the complementary strand for a methylase, termed M.LlaBI, said fragment comprising the DNA sequence from nucleotide 422 to nucleotide 2161 in the enclosed SEQ ID No. 9.

e) A DNA fragment coding for a restriction endonuclease, termed R.LlaBI, said fragment comprising the DNA sequence from nucleotide 2464 to nucleotide 3360 in the enclosed SEQ ID No. 9.

In a third aspect the present invention provides a plasmid-derived type II restriction-modification (R-M) system, termed LlaDII, from *Lactococcus lactis* subsp. *cremoris* W39, said system encoding at least one methylase and a restriction endonuclease, characterized in that the system comprises i) an open reading frame, termed ORF1, from about nucleotide 743 to nucleotide 1282 in the enclosed SEQ ID No. 12, coding for a restriction endonuclease, termed R.LlaDII, having the amino acid sequence essentially as shown in the enclosed SEQ ID No.13 and with the recognition sequence 5'-GC↓NGC-3', and ii) an open reading frame, termed ORF2, from nucleotide 1391 to nucleotide 2341 in the enclosed SEQ ID No. 12, coding for a methylase, termed M.LlaDII, having the amino acid sequence shown in the enclosed SEQ ID No. 14.

This aspect of the invention also includes DNA fragments comprising each of the ORFs in the R-M system LlaDII, i.e.

f) A DNA fragment coding for a restriction endonuclease, termed R.LlaDII, said fragment comprising the DNA sequence from about nucleotide 743 to nucleotide 1282 in the enclosed SEQ ID No. 12.

g) A DNA fragment coding for a methylase, termed M.LlaDII, said fragment comprising the DNA sequence from nucleotide 1391 to nucleotide 2341 in the enclosed SEQ ID No. 12.

Further, the invention includes a DNA cassette comprising one or more of the R-M systems and DNA fragments according to the invention in combination with DNA encoding other phage resistance mechanisms selected from the group consisting of adsorption blocking, abortive infection and R-M systems.

The invention also provides a cloning vector including DNA selected from the group consisting of R-M systems, DNA fragments and DNA cassettes according to the invention, and more specifically the plasmid pSNA1 introduced in *Lactococcus lactis* MG1614 and deposited under the accession number LMG P-15720, the plasmid pAG55 introduced in *Lactococcus lactis* MG 1614 and deposited under the accession number LMG P-15719, and the plasmid pCAD1 introduced in *Lactococcus lactis* subsp. *cremoris* LM2301 and deposited under the accession number LMG P-16901.

The invention also provides an expression vector including DNA selected from the group consisting of R-M systems, DNA fragments and DNA cassettes according to the invention under the control of a promoter capable of providing expression thereof in a host cell, particularly a Gram-positive bacterium, and more particularly a lactic acid bacterium, especially *Lactococcus lactis*.

Further, the invention provides a method of conferring increased virus resistance on a cell wherein said cell is transformed with an expression vector according to the invention. In particular the invention provides a method of conferring phage resistance on a Gram-positive bacterium, more particularly a lactic acid bacterium, and especially a *Lactococcus lactis* strain, wherein said bacterium is transformed with an expression vector according to the invention. The invention also comprises a cell, particularly a Gram-positive bacterium, more particularly a lactic acid bacterium, and especially a *Lactococcus lactis* strain, which carries an expression vector according to the invention.

In addition, the invention provides:

a methylase, termed M.LlaAIA, having the amino acid sequence shown in the enclosed SEQ ID No. 2;

a methylase, termed M.LlaAIB, having the amino acid sequence shown in the enclosed SEQ ID No. 4 or SEQ ID No. 6;

a restriction endonuclease, termed R.LlaAI, with the recognition sequence 5'-↓GATC-3', said endonuclease having the amino acid sequence shown in the enclosed SEQ ID No. 8;

a methylase, termed M.LlaBI, having the amino acid sequence shown in the enclosed SEQ ID No. 10;

a restriction endonuclease, termed R.LlaBI, with the recognition sequence 5'-C↓TRYAG-3', said endonuclease having the amino acid sequence shown in the enclosed SEQ ID No. 11;

a restriction endonuclease, termed R.LlaDII, with the recognition sequence 5'-GC↓NGC-3', said endonuclease having the amino acid sequence essentially as shown in the enclosed SEQ ID No. 13; and a methylase, termed M.LlaDII, having the amino acid sequence shown in the enclosed SEQ ID No. 14.

DETAILED DESCRIPTION OF THE INVENTION

Figure 1:
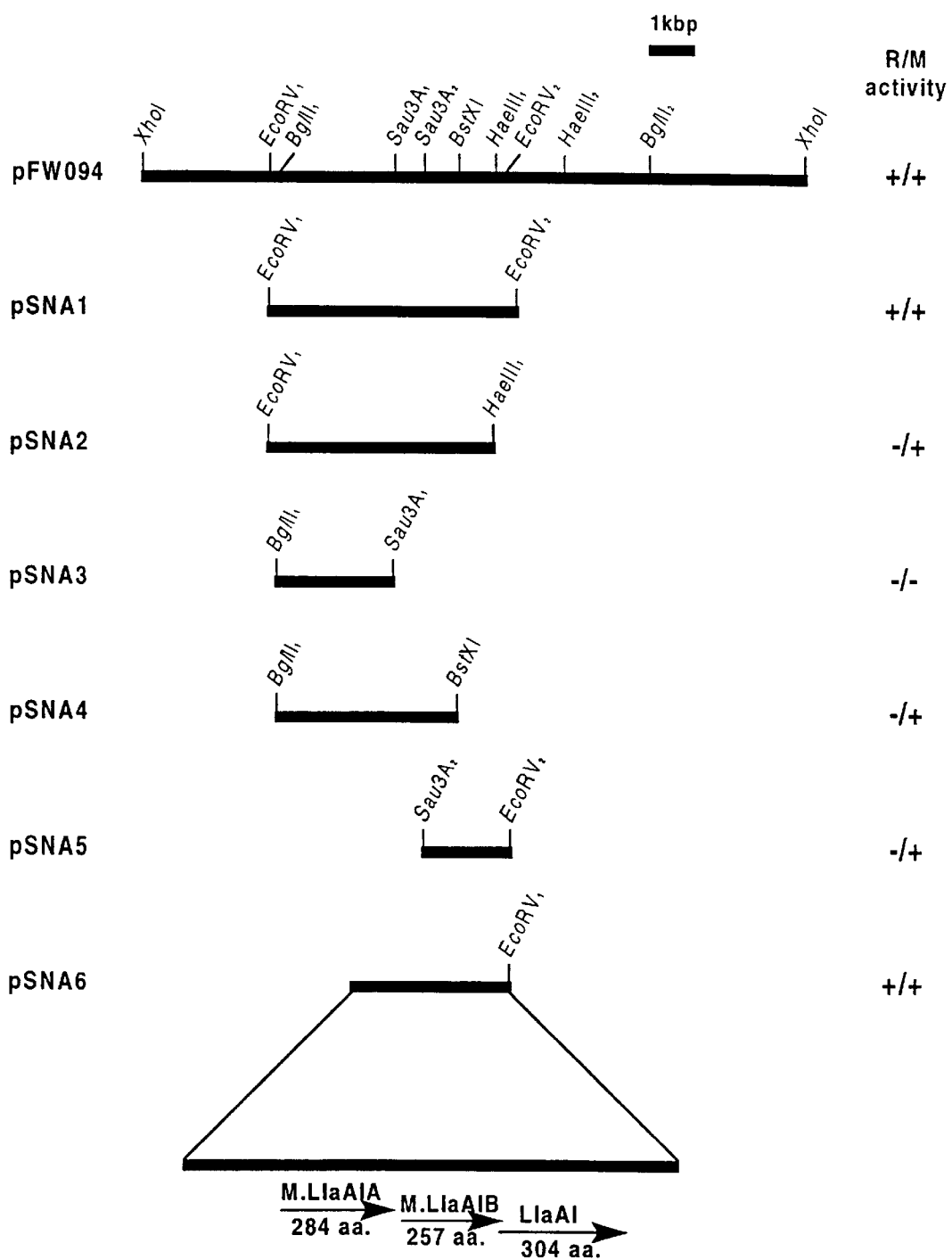
FIG. 1. Maps, restriction and modification activities of pFW094 and subclone fragments thereof and the products of the LlaAI genes. pFW094 is a wild-type plasmid and is shown linearised by cleavage at a XhoI site. Arrows indicate the position of the putative open reading frames and the direction of transcription. The putative sizes in amino acids are indicated for the open reading frames.

In order to determine the biological diversity of the R-M systems we compared six plasmids isolated in our laboratory with three isolated in Chopin's laboratory and one from Klaenhammer's laboratory by use of the prolate headed phage c2 (25). Phage c2 was propagated on each plasmid-containing strain and tested for restriction by all strains. The results are assembled in the following Table 1.

TABLE 1

The EOP of phage c2 on L. lactis strains carrying different R-M encoding plasmids.

| Plasmid from isolate | MG1614 none | T1.1[a] pJW563 W56 | T21.5[d] pJW565 W56 | T46.22[a] pJW566 W56 | T3442.7[a] pFV0802 T29W5 | T912.2[a] pFV1001 V32.2 EOP[d] | T2235.5[a] pFV1201 KH | TB123[b] pTRK12 NCK40 | IL1420[c] pIL6 IL594 | IL1530[c] pIL7 IL594 | IL181 pIL10 IL96 |
|---|---|---|---|---|---|---|---|---|---|---|---|
| MG1614 | 1 | 1 | 1 | 1 | 1 | 1 | 1 | 1 | 1 | 1 | 1 |
| T1.1 | $3 \times 10^{-1}$ | 1 | $3 \times 10^{-1}$ | $3 \times 10^{-1}$ | $10^{-1}$ | $10^{-1}$ | $2 \times 10^{-1}$ | 1 | $4 \times 10^{-1}$ | $2 \times 10^{-1}$ | $4 \times 10^{-1}$ |
| T21.5 | $8 \times 10^{-4}$ | $4 \times 10^{-3}$ | 1 | $7 \times 10^{-3}$ | $10^{-3}$ | $10^{-3}$ | $7 \times 10^{-3}$ | $4 \times 10^{-2}$ | $2 \times 10^{-3}$ | $5 \times 10^{-4}$ | $2 \times 10^{-3}$ |
| T46.22 | $5 \times 10^{-3}$ | $9 \times 10^{-3}$ | $5 \times 10^{-3}$ | 1 | 1 | $3 \times 10^{-3}$ | $3 \times 10^{-3}$ | $7 \times 10^{-3}$ | $4 \times 10^{-3}$ | $5 \times 10^{-3}$ | $10^{-2}$ |
| T3442.7 | $10^{-2}$ | $8 \times 10^{-3}$ | $6 \times 10^{-3}$ | 1 | 1 | $10^{-2}$ | $6 \times 10^{-3}$ | $10^{-2}$ | $7 \times 10^{-3}$ | $6 \times 10^{-3}$ | $10^{-2}$ |
| T912.2 | $9 \times 10^{-2}$ | $3 \times 10^{-1}$ | $2 \times 10^{-1}$ | $4 \times 10^{-1}$ | $4 \times 10^{-1}$ | 1 | $2 \times 10^{-1}$ | $5 \times 10^{-2}$ | $4 \times 10^{-2}$ | $10^{-1}$ | $10^{-1}$ |
| T2235.5 | $6 \times 10^{-2}$ | $8 \times 10^{-2}$ | $2 \times 10^{-1}$ | $9 \times 10^{-2}$ | $10^{-1}$ | $8 \times 10^{-2}$ | 1 | $3 \times 10^{-1}$ | $8 \times 10^{-2}$ | $7 \times 10^{-2}$ | $10^{-1}$ |
| TB123 | $4 \times 10^{-2}$ | $3 \times 10^{-2}$ | $10^{-1}$ | $9 \times 10^{-2}$ | $10^{-1}$ | $4 \times 10^{-2}$ | $10^{-2}$ | 1 | $10^{-1}$ | $5 \times 10^{-2}$ | $10^{-1}$ |
| IL1420 | $7 \times 10^{-4}$ | $2 \times 10^{-4}$ | $2 \times 10^{-5}$ | $5 \times 10^{-4}$ | $2 \times 10^{-4}$ | $10^{-4}$ | $7 \times 10^{-2}$ | $3 \times 10^{-6}$ | $7 \times 10^{-2}$ | $2 \times 10^{-5}$ | $4 \times 10^{-4}$ |
| IL1530 | $6 \times 10^{-3}$ | $6 \times 10^{-3}$ | $2 \times 10^{-3}$ | $6 \times 10^{-3}$ | $10^{-3}$ | $9 \times 10^{-4}$ | $10^{-3}$ | $8 \times 10^{-3}$ | $10^{-1}$ | $10^{-1}$ | $4 \times 10^{-3}$ |
| IL1813 | $3 \times 10^{-5}$ | $10^{-4}$ | $4 \times 10^{-5}$ | $4 \times 10^{-5}$ | $10^{-5}$ | $2 \times 10^{-5}$ | $3 \times 10^{-5}$ | $7 \times 10^{-5}$ | $2 \times 10^{-5}$ | $3 \times 10^{-6}$ | 1 |
| Type-II[e] | — | +(LlaBI) | — | — | — | — | — | — | — | — | — |

[a]The plasmids were cotransformed into L. lactis MG1614 together with pVS2 and afterwards cured for pVS2 by growing the cells in the presence of novobiocin.
[b]A gift from T. Klaenhammer. The plasmid is in L. lactis MG1363.
[c]A gift from M.-C. Chopin. The plasmids are in L. lactis IL1403. (5).
[d]EOP was calculated as the phage titer on the test strain divided by the titer on L. lactis MG1614. The EOP is an average of at least four experiments.
[e]Type-II ENase activity was carried out as written in FIG. 1. +. indicate activity and –. no activity.

The results in Table 1 demonstrate that phages propagated on T46.22 [pJW566] and T3442.7 [pFV0802] were not restricted by each other. This showed that pJW566 and pFV0802 probably code for identical R-M systems. T1.1 did not restrict phages propagated on TB123, but TB123 restricted T1.1 propagated phages. This indicated either that two R-M systems could be encoded on pTRK 12, one of which is identical to the one encoded by pJW563, or that the MTase encoded by pTRK12 cross-protects against the pJW563-encoded R-M system. We also observed that phage c2 propagated on IL1420 or IL1530 gave a lower titer on the propagating host, than on the plasmid-free strain L. lactis MG1614. This is not due to differences in strain background, since this effect was not found in L. lactis IL1813. These data imply that in addition to a R-M system, pIL6 and pIL7 also code for an additional phage resistance mechanism, not previously identified. The remaining MTases were not able to protect the phage from restriction by the other R-M systems, indicating that they are different from each other. This shows that L. lactis strains have a large diversity of plasmid-encoded R-M systems.

The diversity of R-M-encoding plasmids identified in Lactococcus made us screen all isolates from the TK5 starter for the presence of type II ENase activity. Five different type II ENase activities, R.LlaAI, R.LlaBI, R.LlaCI, R.LlaDI and R.LlaEI, were identified. Table 2 depicts the distribution of ENase activity among the TK5 isolates.

TABLE 2

Type-II ENase activity in L. lactis isolates from the TK5 starter culture.

| | Type II ENase activity[b] | | | | |
|---|---|---|---|---|---|
| Group[a] | R. LlaAI | R. LlaBI | R. LlaCI | R. LlaDI | R. LlaEI |
| | L. lactis strains | | | | |
| 1: (16) | W21, W70 | | | | |
| 2: (4) | | | | | |
| 3: (5) | W9, W25, W69, W71, W72 | | | | |

TABLE 2-continued

Type-II ENase activity in L. lactis isolates from the TK5 starter culture.

| | Type II ENase activity[b] | | | | |
|---|---|---|---|---|---|
| Group[a] | R. LlaAI | R. LlaBI | R. LlaCI | R. LlaDI | R. LlaEI |
| | L. lactis strains | | | | |
| 4: (5) | | W3, W52, W56, W66, W67 | | | |
| 5: (4) | W41, W43 | | | | |
| 6: (2) | | | W40 | | |
| outside: (29) | W14, W53, W54 | | W15 | W39 | W12 |

[a]The isolates were grouped according to their plasmid profile (22). Numbers in parentheses show the number of isolates belonging to the group.

It is seen from Table 2 that none of the screened isolates expressed more than one type II ENase activity. The most common ENase was the R.LlaAI, which was found in 12 (19 %) of the isolates. R.LlaBI was found in five (8%), R.LlaCI in two (3%), with R.LlaDI and R.LlaEI in one (2%) of the isolates. Thus, approximately 1/3 of the strains in the TK5 starter culture contained a type II R-M system.

From two of the strains that showed type II ENase activity, W9 (Group 3) and W56 (Group 4), we had previously isolated R-M-encoding plasmids. This enabled us to test if the activity was chromosomally or plasmid encoded. The transformants T1.1[pJW563], T21.5[pJW565], T46.22 [pJW566] (Table 1) carried plasmids from W56; TW093 [pFW093] and TW094[pFW094] carried plasmids from W9. These were examined and we found that only T1.1 and TW094 exhibited type II ENase activity. The two systems identified in the TK5 isolates W12 and W15 quite likely are plasmid encoded. In order to determine whether the LlaDI endonuclease was plasmid encoded, the cotransformation procedure into L. lactis MG1614 was made with total plasmid DNA from W39. We found that only transformant L. lactis MG1614[pHW393] expressed LlaDI endonuclease activity which shows that also the LlaDI R-M system is plasmid encoded. The other transformants from Table 1 were also examined. None of these strains exhibited type II ENase activity. This suggests that other ENase activity than type II exists in Lactococcus. Additional experiments are required to determine the type of R-M systems coded for on these plasmids.

The recognition sequences for LlaCI, LlaDI and LlaEI have not yet been determined. It is interesting that we have found a much wider diversity of type II ENases in Lactococcus, than previously reported (27). Also the two ENases characterized by us have recognition sequences with at least 50% A+T, in contrast to the 5 bp-recognizing ENases (5'-CCNGG-3' or 5'-CCWGG-3') reported for Latococcus and *Streptococcus thermophilus* (27). This may have practical implications, as Lactococcus and lactococcal phages have approximately 60% A+T in their genomes (40).

When we tried to clone the LlaDI R-M system we discovered that the plasmid pHW393 also coded for another type II R-M system which we designated LlaDII.

The cloning and sequencing of the R-M systems LlaAI, LlaBI and LlaDII is described in the following Examples 1, 2 and 3, respectively.

EXAMPLE 1

In the following we describe the identification, cloning and sequence of the plasmid-derived LlaAI R-M system from *Lactococcus lactis* subsp. *cremoris* W9. We show that the plasmid-free Lactococcus strain MG1614 obtains a higher degree of phage resistance with the plasmid pFW094 or the plasmid pSNA1 than without it. The cloning and sequence of the LlaAI R-M system is shown, and the putative ORFs and orientation of two MTases and one ENase are shown. The deduced amino acid sequences were compared with known type II R-M systems and, surprisingly, strong homology was found to the isoschizomer DpnII R-M system from *Diplococcus pneumoniae* and to MboI from *Morexella bovis*.

Materials and Methods

Strains, phages, plasmids and growth condition. *Lactococcus lactis* subsp. *cremoris* (*L. lactis*) W9 obtained from E. Waagner Nielsen (22), and *Lactococcus lactis* subsp. *cremoris* MG1614 (12) (previously designated *L. lactis* subsp. *lactis* MG1614 (14)), obtained from Atte von Wright, was grown at 30° C. in M17 medium (44) supplemented with 0,5% glucose (GM17). When required, 10 µg/ml chloramphenicol or 5 µg/ml erythromycin was added. The *Escherichia coli* strains, XL1-Blue (Stratagene) and TC1685. obtained from Tove Atlung, were grown at 37° C. in LB supplemented with chloramphenicol, erythromycin, tetracycline or ampicillin at the concentrations 10, 100, 12,5 and 100 µg/ml, respectively. Plasmid pVS2 was cured with 1 µg/ml novobiocin. The isometric headed phages jj50 (23) and c2 (25) were propagated and plaque assayed as described by Terzaghi and Sandine (44). Phage sensitivity was performed by plaque assay and cross streaking with phage jj50 as described previously (23). Phage λ b2 was propagated as described by Sambrook et al (37). The plasmids used in this study are shown in Table 3.

TABLE 3

Plasmids.

| Plasmid | Relevant characteristics | Source or reference |
|---|---|---|
| pFW094 | 15.5 kbp isolated from *L. lactis* W9 | this work |
| pVS2 | 5.0 kbp, Cm$^R$, Ery$^R$ | A. von Wright |
| pSA3 | shuttle vector, Ery$^R$ in Lactococcus Cm$^R$ in *E. coli* | (7) |
| pBluescriptIISK+ | Am$^R$ | Stratagene |
| Name cloned in pSA3 | Name cloned in pIISK+ | |
| pSNA1 | pNA1 | 6.0 kbp EcoRV fragment of pFW094 | this work |
| pSNA2 | pNA2 | 5.5 kbp EcoRV-HaeIII fragment of pSNA1 | this work |
| pSNA3 | pNA3 | 3.1 kbp Bg/II-Sau3 A fragment of pSNA1 | this work |
| pSNA4 | pNA4 | 4.6 kbp Bg/II-BstXI fragment of pSNA1 | this work |
| pSNA5 | pNA5 | 2.1 kbp Sau3A-EcoRV fragment of pSNA1 | this work |
| pSNA6 | pNA6 | 3.7 kbp deletion-EcoRV fragment of pNA1 | this work |

Preparation of cell extracts. A 500 ml fresh over-night culture of *L. lactis* or *E. coli* was harvested by centrifugation at 8 000×g, washed twice in ice-cold lysis buffer (50 mM Tris-HCl pH 7.6, 10 mM MgCl$_2$, 25 mM NaCl, 7 mM mercaptoethanol). Cell were suspended in 10 ml cold lysis buffer and disrubted using a French press (Aminco, USA) at 1 000 psi (6,9 MPa). The crude extract was centrifugated for 30 min at 40 000×g before glycerol was added to a final concentration of 20%. Aliquots were stored at −20° C. Small scale preparation of *E. coli* extract was carried out by centrifugation of a 10 ml overnight culture at 15 000×g, washing twice with lysis buffer. The cells were resuspended in 0.5 ml lysis buffer before sonical disruption. After centrifugation at 15 000×g the supernatant was stored at −20° C. in 20% glycerol.

Determination of endonuclease activity. Type II endonuclease activity in vitro was determined by incubating cell extract or purified enzyme with pBluescriptIISK+ or phage λ DNA in 50 mM Tris-HCl pH 7.6, 80 mM NaCl, 10 mM MgCl$_2$, 0.001 M DTT. After 2 hrs at 37° C. the reaction mixtures were analyzed by horizontal electrophoresis in agarose gel with TEA buffer (37). In vitro endonuclease activity was determined as an average of three independent determinations of the efficiency of plating (EOP) performed as described earlier (23).

Determination of methylase activity. Phage jj50, or λ b2 was purified three times over single plaques and propagated on the selected strains. Phage DNA was isolated by standard procedure (37). Phage DNA was incubated with purified LlaAI endonuclease (33) as described above. In vitro methylase activity was observed if the DNA was protected against cleavage with the purified LlaAI endonuclease. In vivo LlaAI methylase activity was determined by plaque assays as described previously (23).

Transformation. Protoplast transformation of Lactococcus was conducted as previously described (23). *L. lactis* MG1614 was grown with 4% glycine and transformed by electroporation using a Bio-Rad Gene Pulser apparatus (Bio-Rad Laboratories, Richmond, Calif., USA) as described by Holo and Nes (19). *E. coli* was transformed by the CaCl$_2$ standard procedure as described by Sambrook et al (37).

DNA isolation and cloning. Plasmid DNA was extracted from *L. Lacks* by the method of Andresen et al (1) and further purified by CsCl-EtBr gradients (37). Plasmid was isolated from *E. coli* by alkaline lysis (37) and further purified by QIAGEN kit (QIAGEN Inc., Chatsworth, USA) or by CsCl-EtBr gradient (37). Phage DNA was purified by the methods described by Sambrook et al (37). Deletions were performed with the 'Erase-a-base' system (Promega Corp., Madison, USA). Blunt ends were created by filling in with Klenow fragment of DNA polymerase (Boehringer Mannheim, Mannheim, Germany). Restriction endonuclease, T4 ligase, and Calf Intestine Alkaline Phosphase (CIP), were purchased from Boehringer Mannheim (Mannheim, Germany) or New England Biolabs (Beverly, USA). All enzymes and kits were used according to the manufacturers recommendations.

DNA sequencing. The nucleotide sequence was determined by the dideoxynucleotide chain termination method (39) using double-stranded DNA as template. Restriction fragments and deleted fragments in pBluescriptIISK+ were sequenced in both directions with the Sequenase version 2.0 Kit (United States Biochemical, Cleveland, Ohio) using [$^{35}$S]-dATP (Amersham, England) and standard primers (Stratagene). A few non-overlapping sequences were sequenced directly on the intact pFW094 plasmid using synthetic primers purchaced from P. Hobolt (Department of Microbiology, The Technical University, Denmark). Compressed DNA sequences were resolved by using Ampli-Cycle™ Sequencing kit (Perkin Elmer). Computer analysis was based on GCG sequence analysis program (Version 7.0) (10).

Sequences comparison. The sequence of the LlaAI gene was compared with R-M genes from the GenBank and the EMBL data bank.

Results

Identification and isolation of the R-M encoding plasmid pFW094. Total plasmid DNA from *L. Lactis* W9 was isolated and protoplast transformed together with pVS2 (chloramphenicol marker) into the plasmid-free strain *L. Lactis* MG1614 (23). Cm$^R$ transformants were tested for phage resistance with phage jj50/MG1614. Phage jj50 was propagated and plaque assayed on *L. Lactis* MG1614 and on transformants with increased phage resistance (data not shown). By this method two R-M coding plasmids, pFW093 and pFW094, 12.7 kbp and 15.5 kbp, respectively, were identified. The transformants, TW093 and TW094, carrying pFW093 and pFW094, respectively, were isolated after curing of pVS2. Transformants TW093 and TW094 restricted phage jj50 with an EOP of 10$^{-3}$ and 10$^{-5}$ respectively, indicating that both plasmids code for phage resistance mechanisms.

Cell extracts from *L. Lactis* W9, TW093 and TW094 were screened for type II endonuclease activity. Only *L. Lactis* W9 and the transformant TW094 expressed type II activity, designated LlaAI. The endonuclease was purified and its recognition sequence determined as earlier described (34). The LlaAI system recognized the sequence 5'-↓GATC-3' (34). LlaAI is an isoschizomer of MboI from *Moraxella bovis* and DpnII from *Streptococcus pneumoniae*. λ DNA and plasmid DNA isolated from dam$^+$ *E. coli* strains were refractory to digestion with the restriction endonuclease LlaAI, indicating that methylation of the adenine in the recognition sequence protected against cleavage by the LlaAI endonuclease.

Plasmid pFW094 was stably maintained during at least 500 generations in *L. lactis* MG1614 without any loss of the capability to restrict phages.

Cloning of the R-M system. A restriction map of pFW094 was constructed as shown in FIG. 1. Different restriction fragments were ligated into the shuttle vector pSA3 and transformed into *L. lactis* MG1614 selecting for Ery$^R$. Transformants were examined for expression of R-M activity, and the resulting EPOs of phages jj50 and c2 are shown in Table 4.

TABLE 4

Restriction activity of *Lactococcus lactis* MG1614 harbouring different plasmids on the phages jj50 and c2.

| | EOP of phage: | | |
|---|---|---|---|
| Strain: | jj50/MG1614 | c2/MG1614 | jj50/MG1614[pFW094] |
| MG1614 | 1 | 1 | 1 |
| MG1614 [pFW094] | 10$^{-5}$ | 10$^{-4}$ | 1 |
| MG1614 [pSNA1] | 10$^{-7}$ | 10$^{-6}$ | 1 |
| MG1614 [pSNA2] | 10$^{-1}$ | 10$^{-1}$ | 1 |
| MG1614 [pSNA6] | 10$^{-7}$ | 10$^{-6}$ | 1 |

[ ] denotes the plasmid

Plasmid pSNA1 was constructed by cloning a 6,0 kbp EcoRV fragment from pFW094 into pSA3. *L. lactis* MG1614 [pSNA1] restricted phages jj50 and c2 to an EOP of 10$^{-7}$ and 10$^{-6}$, respectively (Table 4), showing that both the endonuclease and methylase activity was expressed by the plasmid in *L. lactis* MG1614 (FIG. 1). Deletions of the HaeIII-EcoRV$_2$ fragment from pSNA1, resulted in plasmid pSNA2, which did not restrict phages in *L. lactis* MG1614 (EOP increased from 10$^{-7}$ resp. 10$^{-6}$ to 10$^{-1}$), but it had methylase activity (FIG. 1). This showed that the HaeIII site was located within the gene encoding the endonuclease LlaAI. To localize the LlaAI methylase, the subclones, pSNA3, pSNA4 and pSNA5 were constructed by cloning of restriction fragments of pSNA1 into pSA3, as shown in FIG. 1. The plasmid pSNA3 contained the 3.1 kbp BglII-Sau3A$_1$ fragment, pSNA4 the 4.6 kbp BglII-BstXI fragment, and pSNA5 the 2.1 kbp Sau3A$_2$-EcoRV$_2$ fragment, all inserted into pSA3. None of the three clones restricted phages and only pSNA4 expressed methylase activity. This indicates that the the Sau3A-BstXI fragment is part of the methylase gene.

Plasmid pNA1 was constructed by cloning the 6.0 kbp EcoRV fragment in pBluescriptIISK+ in *E.coli* XL1-Blue. Deletions were made from the EcoRV$_1$ site of plasmid pNA1.

From one of the generated derivatives pNA6, the overhangs of a 3.7 kbp BssHII-EcoRV$_2$ fragment was filled in and cloned into the EcoRV site of pSA3 yielding pSNA6. *L. lactis* MG1614 [pSNA6] restricted phage jj50 with an EOP of 10$^{-7}$ (Table 2), indicating that the 3.7 kbp BssHII-EcoRV$_2$ fragment is the smallest fragment obtained that contains all the information necessary for the expression of the R-M system in Lactococcus.

*E. coli* TC1685 (dam$^-$) was transformed with plasmids pSNA1 and pSNA6. None of the transformants expressed endonuclease activity as determined by plaque assay with phage λ b2 or by assaying *E. coli* cell extracts for endonuclease activity (data not shown). However, when phage λ b2 DNA was propagated through TC1685 containing pSNA1 or pSNA6, the λ DNA was refractory to digestion with the purified endonuclease LlaAI, indicating that the phage DNA was fully methylated and that plasmid pSNA1 and pSNA6 had expressed methylase activity.

Deposit. *Lactococcus lactis* MG1614 transformed with plasmid pSNA1 comprising the LlaAI R-M system has been deposited at the Belgian Coordinated Collections of Microorganisms (BCCM), Laboratorium voor Microbiologie—Bacteriënverzameling (LMG), Universiteit Gent, Belgium, under the accession number LMG P-15720.

Gene organization and DNA sequence. Subfragments of the 6.0 kbp EcoRV fragment were cloned in the cloning vector pBluescriptIISK+ and transformed into E.coli XL1-Blue. Several of the clones were deleted in one direction as described in Material and Methods. The nucleotide sequence of a 3.7 kbp region containing the LlaAI R-M genes was determined on both strands. Three open reading frames, ORF1, ORF2 and ORF3, were located on the same strand of DNA (SEQ ID No. 1). The ORF1 was located between nt 769 to 1620. The ORF1 contained an initiation codon (ATG) and a putative but unusual ribosomal binding site (RBS) (GGTATAA) located at position 755 to 761. If the initiation codon at position 769 is used, ORF1 should encode a protein of 284 amino acid. Since the plasmid pSNA4, containing ORF1 and part of ORF2, expressed LlaAI methylase activity (FIG. 1), ORF1 must encode a methylase, M.LlaAIA. The ORF2 is presumably positioned 29 bp downstream of ORF1 and correspond to position 1649 to 2419. The initiation codon at position 1649 is preceded by a RBS (GGAGG) that conforms well to the consensus RBS (GGAGG) positioned 7 bp upstream of a putative ATG start codon. If this start codon is used, the ORF2 should encode a protein of 257 amino acids. However, there is another initiation codon at position 1613, but it is not preceded by a consensus RBS. If this is used as the start codon, the ORF2 should encode a protein of 269 amino acids. It is not yet known which of the two initiation codons is actually used. The ORF3 is located between nucleotides 2412 and 3323 with a 8 bp overlap to the ORF2 and is preceded by a possible RBS 7 bp upstream (AAGGAG). The protein which could be translated from ORF3 starting at position 2412 would contain 304 amino acids. Deletions of the region downstream to the HaeIII$_1$ site at position 3203 abolished endonuclease activity in plasmid pSNA2, showing that ORF3 code for the endonuclease, R,LlaAI. A putative promoter for the LlaAI R-M system could be located from position 699 to 726. The putative promoter region might contain a −10 region (TATTTA), which has good homology to the consensus, and a −35 region (TTAAGA) with low homology to consensus, 16 bp upstream. Downstream the IlaAI gene with a 6 bp overlap is a putative rho-independent transcriptional terminator structure with a −G=−26 kJ/mol. No terminator-like structures were found downstream of ORF1 and ORF2. This indicated that the LlaAI R-M system consisted of three ORFs, possibly transcribed as a single polycistronic mRNA. ORF1 codes for a methylase, M.LlaAIA, and ORF3 for a restriction endonuclease, R,LlaAI.

Comparison of amino acid sequences. No primary sequence homology was found between the restriction endonuclease R,LlaAI and the methylase M.LlaAIA or the deduced protein encoded by ORF2, and no sequence similarities besides motifs I and II (se below) were found between the methylase M.LlaAIA and the deduced ORF2 encoded protein. The deduced protein encoded by ORF1 contained the motif I, PFXGXGAhXXG, and the motif II, DhVhXDPPYh, often found in adenine methylases (29) indicating that this ORF most likely codes for an adenine methylase. The same motifs were found in the deduced protein from ORF2 indicating that this ORF most likely also encode an adenine methylase. The deduced amino acid sequences from the LlaAI R-M system were compared to the isoschizomeric systems, DpnII from *Diplococcus pneumoniae* (28) and MboI from *Moraxella bovis* (47). Based on amino acid sequence alignments of the three R-M systems, LlaAI, DpnII and MboI, the calculated identity is shown in Table 5.

TABLE 5

Amino acid sequence identity between the LlaAI R-M system and the DpnII and MboI R-M systems.

| | DpnM | DpnA | DpnB | MboA | MboI | MboC |
|---|---|---|---|---|---|---|
| M. LlaAIA | 75% | — | — | 45% | — | — |
| M. LlaAIB | — | 86% | — | — | — | 50% |
| R. LlaAI | — | — | 32% | — | 36% | — |

The three R-M systems are very homologous, especially the two methylases from the DpnII and the deduced M.LlaAIA and ORF2 encoded protein of the LlaAI systems were highly homologous (Table 5). The identity between the methylase M.LlaAIA and DpnM was 75%, and between the methylase DpnA and the protein from ORF2 86%. The results are consistent with the proposal that both ORF1 and ORF2 encodes adenine methylases designated M.LlaAIA and M.LlaAIB, respectively, and similar to DpnM and DpnA. Less amino acid identity was found between the methylases from the LlaAI and the MboI systems, 45% and 50% identity, respectively, (Table 5). The identity between the M. LlaAIA and the Dam methylase from *E. coli* was even lower (32%, data not shown). As expected the identity between the endonuclease from the three R-M systems was not as significant as between the methylases. However, the identity between R,LlaAI, and R,MboI and R,DpnII was 36% and 32%, respectively (Table 5). The LlaAI endonuclease did not show any strong homology to other endonucleases from the GenBank database. The LlaAI and the DpnII systems have the same gene organization: Genes encoding methylases are located upstream of the gene encoding the endonuclease, whereas in the MboI system, the gene encoding the endonuclease is located between the two methylases.

Discussion

LlaAI is the first R-M system from *Lactococcus lactis*, with known recognition sequence, which has been cloned and completely sequenced. The LlaAI system has a recognition sequence 5'-↓GATC-3' deviating from the recognition sequences of ScrFI and LlaAI , recognizing 5'-CC↓NGG-3' and 5'-CC↓WGG-3', respectively (27), in being more AT rich. This may have practical implication, since Lactococcus has AT rich DNA (34–40% CG (40)). The genes were localized to a 3.7 kbp fragment. Interestingly, when the 3.7 kbp fragment cloned in pSA3 (pSNA6) was introduced into *L. lactis* MG1614, it restricted phage jj50 with an even higher efficiency ($10^{-7}$) than the wild-type plasmid. This may be due to a slightly higher plasmid copy number of pSNA6 compared to pFW094 and therefor a higher level of expression of the LlaAI genes involved in the R-M phage resistance mechanism. In *E. coli* TC1685, however, pSNA6 only expressed methylase activity. Whether this is due to instability of the mRNA or to a regulatory mechanism of the LlaAI endonuclease, that does not function in *E. coli*, is not known.

We found that the R-M system consisted of three ORF's putatively transcribed on a polycistronic mRNA. The gene organization: two methylase genes followed by the endonuclease gene, is the same as for the genes encoding the DpnII R-M system (28) but not like the MboI system (47), which has the endonuclease gene surrounded by the two methylase genes.

The two LlaAI methylases showed a very high degree of identity (75 and 86%) to the two methylases from the DpnII R-M systems. From the DpnII R-M system it has been found, that one of the DpnII methylases, DpnM, is an N6-adenine methylase that methylate hemimethylated DNA (9) in the sequence 5'-GATC-3', whereas the other methylase, DpnA, methylate single stranded DNA (4). The sensitivity of the LlaAI endonuclease to dam methylation and the high identity between the DpnM and M.LlaAIA suggests that M.LlaAIA also is a N6-adenine methylase methylating hemi-methylated DNA. The high identity between the DpnA and M.LlaAIB suggests that M.LlaAIB may act like DpnA and methylate single stranded DNA. The homologies found between Dam, DpnM, MboA and M,LlaAI indicate a strong relationship between the four 5'-GATC-3' N6-Adenine methylases. Despite the fact, that the Dam methylase has an other biological function than DpnM, M.MboA and M,LlaAI, it appears that the four methylases originate from a common ancestor and that the methylases have diverged into different biological functions. No homology besides the two motifs I and II was found between the two LlaAI methylases, M.LlaAIA and M.LlaAIB, indicating that the two LlaAI methylases are not a result of gene duplication, but have evolved independently of each other.

The homology between the endonuclease from LlaAI and those from DpnII (32%) and MboI (36%) is unusually high for isoschizomers, indicating a common ancestor. Similar results have been seen before (52), but most often no similarities are seen between isoschizomers (52).

EXAMPLE 2

Here we report the cloning and nucleotide sequence of the genes coding for the LlaBI system from *Lactococcus lactis* subsp. *cremoris* W56. The LlaBI endonuclease is an isoschizomer to SfcI from *Enterococcus faecium. L. Iactis* W56 has previously been isolated from the Danish mixed Cheddar starter, TK5 (22). It was shown that *L. lactis* W56 harbors at least three plasmids, pJW563, pJW565, and pJW566, which encode distinct R-M systems (23). It was found that transformants harbouring the plasmid pJW563 expressed type II activity, named LlaBI (34).

Materials and Methods

Strains, phages, plasmids and growth conditions. The strains *Lactococcus lactis* subsp. *cremoris* W56, obtained from E. Waagner Nielsen (22) and *Lactococcus lactis* subsp. *cremoris* MG1614, originally classified as *Lactococcus lactis* subsp. *lactis* (12; 14), obtained from Atte von Wright, were grown at 30° C. in M17 media (Oxoid) supplemented with 0,5% glucose (GM 17) and 5 mM $CaCl_2$ when phages were used. The antibiotics were purchased from Sigma and were used at the following concentrations: chloramphenicol, 10 μg/ml; erythromycin and tetracycline, 5 μg/ml. *Eschericia coli* strains XL1l-Blue (Stratagene) and HB101 (3) were grown at 37° C. in LB supplemented with chloramphenicol, erythromycin, tetracycline or ampicillin at 10, 100, 12,5 and 100 μg/ml, respectively, when needed. The isometric headed phage jj50 and the prolate headed phage c2 (25) were propagated and titrated by the method of Terzaghi and Sandine (34). λ b2 phage was propagated as described by Sambrook (37). The plasmids used in this study are shown in Table 6.

TABLE 6

Plasmids.

| Plasmid | Relevant characteristics | Source or reference |
|---|---|---|
| pJW563 | $r^4/m^4$ | (23) |
| pSA3 | shuttle vector | (7) |
| pBluescriptIISK+ | | Stratagene |
| pUC7, erm | pUC7::1.1 kbp HinPI pIL253 erm | W. M. de Vos, NIZO, Ede, The Netherlands |
| pJWC1 | pJW563::cam cassette in ClaI site | this work |
| pJWC2 | pJWC1::deletion of 1.2 kbp BCII fragment | this work |
| pJWE1 | pJWC1::1.1 kbp ery cassette in BglII site | this work |
| pSNB1 | pSA3::4.0 kbp HindIII pJW563 | this work |
| pSK-cm1 | pBluescriptIISK+::3.9 kbp pVC5 cam | Finn K. Vogensen |
| pAG55 | pSK-cm1::3.1 kbp HindIII pJW565;::6.4 kbp EcoRI pJW563 | this work |

Preparation of cell extracts. A 500 ml fresh over-night culture of *L. lactis* was harvested by centrifugation at 8 000×g washed twice in 10 ml cold lysis buffer (50 mM Tris-HCl pH 7.6, 10 MM $MgCl_2$, 25 mM NaCl, 7 mM mercaptoethanol) and suspended in 10 ml cold lysis buffer. A French press (Aminco, USA) was used to disrupt the cells at 1 000 psi (6,9 MPa). The crude extracts were centrifugated for 30 mn at 40 000×g before glycerol was added to the supernatant to a final concentration of 20%. Aliquots of the extract were stored at −20° C.

Determination of endonuclease activity. Type II endonuclease activity in vitro was determined by incubating cell extract or purified enzyme (34) with pBluescriptIISK+ or phage λ DNA in 50 mM Tris-HCl pH 7.9, 10 mM NaCl, 10 mM $MgCl_2$, 100 μg/ml BSA, 0.001 M DTT. After 2 hrs incubation at 37° C. the reaction mixture was analyzed by horizontal electrophoresis in agarose gel with TAE buffer (37). The in vivo endonuclease activity was determined as an average of three independent determinations of the efficiency of plating (EOP) performed as described earlier (23).

Transformation. *L. Iactis* MG1614 was grown with 4% glycine and transformed by electroporation using a Bio-Rad Gene Pulser apparatus (Bio-Rad Laboratories, Richmond, USA) as described by Holo and Nes (19). *E. coli* strains were transformed by the $CaCl_2$ standard procedure (37).

DNA isolation and cloning. Plasmid DNA was extracted from *L. lactis* strains by the method of Andresen et al (1) and purified by the CsCl gradient method (37). Plasmid DNA isolation from *E. coli* was performed by alkaline lysis (37). DNA was further purified by QIAGEN coloums (QIAGEN Inc., Chatsworth, USA) or by CsCl-EtBr gradients (37). Phage DNA was isolated as described by Sambrook et al. (37). Restriction endonucleases, T4 ligase, and Calf Intestine Alkaline Phosphase (CIP) were purchased from Boehringer Mannheim (Mannheim, Germany) or New England Biolabs (Beverly, USA). Deletions of subcloned fragments were obtained by using the 'Erase-a-base' system (Promega Corp., Madison, USA). All enzymes and kits were used according to the manufacturer's recommendations.

DNA sequencing. The nucleotide sequence was determined by the dideoxynucleotide chain termination method (39) using double-stranded DNA as templates. Restriction fragments and deleted fragments cloned in pBluescriptIISK+ were sequenced using the Sequenase version 2.0 kit (United States Biochemical, Cleveland, Ohio, USA). The sequencing was done in both directions using

[35S]-dATP (Amersham, England) and standard primers (Stratagene) complementary to the region of the plasmid upstream of the deleted fragments. A few regions were sequenced by PCR directly from the intact pJW563 plasmid using synthetic primers provided by P. Hobolt (Department of Microbiology, The Technical University, Denmark). In case of compression, DNA sequencing was carried out with AmpliCycle™ Sequencing kit (Perkin Elmer). All computer analysis was done with GCG sequence analysis program (Version 7.0) (10).

Sequence comparisons. The sequence of the LlaBI genes was compared to R-M genes from the GenBank and the EMBL data bank.

Results

Figure 2:
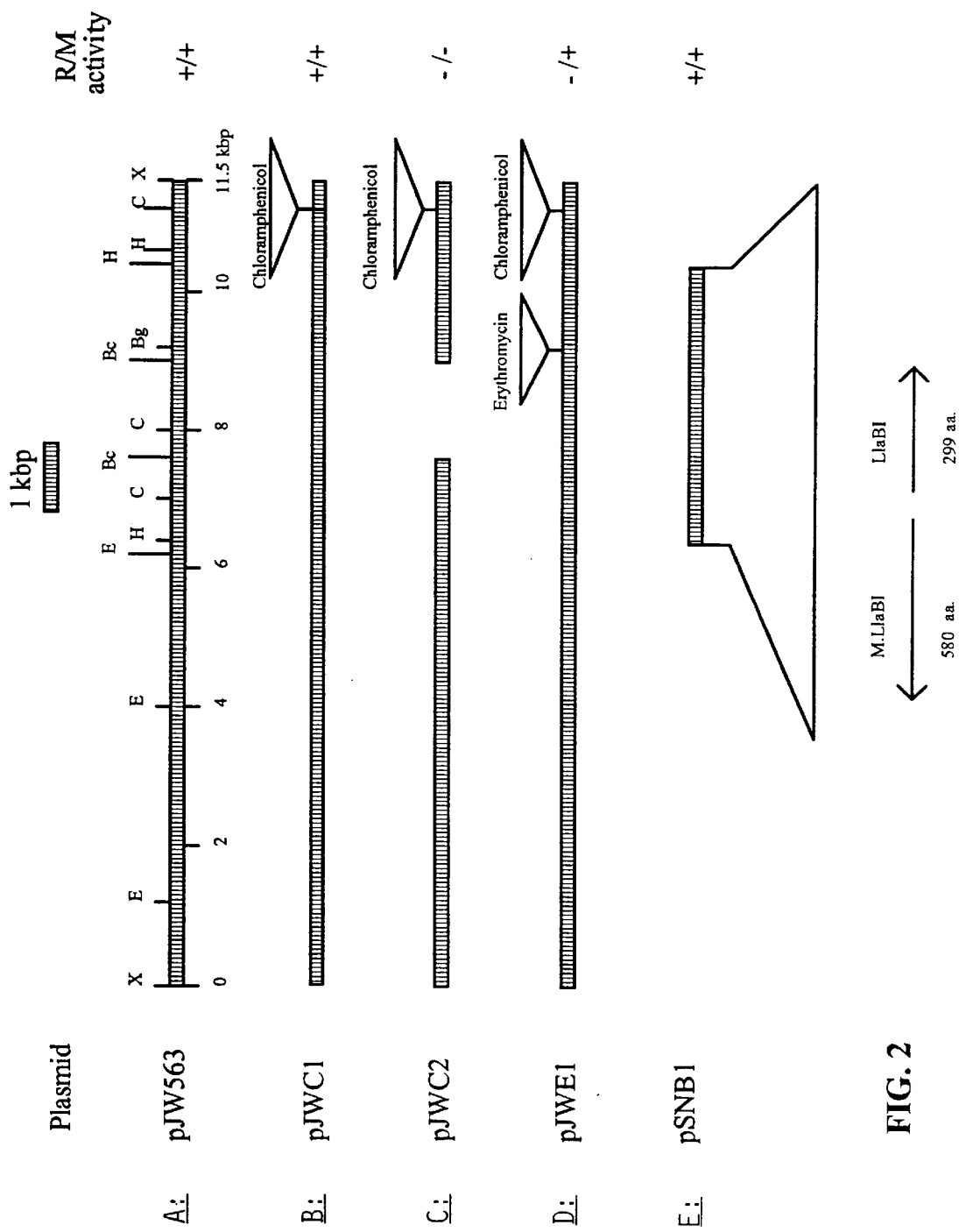
FIG. 2. Maps, restriction and modification activities of pJW563, its derivatives and the subclone fragment in pSNB1 as well as the products of the LlaBI genes. pJW563 is a wild-type plasmid. Plasmids are shown linearised by cleavage at a XhoI site. Arrows indicate the position of the putative open reading frames and the direction of transcription. The putative sizes in amino acids are indicated for the open reading frames. The figure illustrates the activity measured for the different plasmids constructed. A: restriction map of pJW563; B: effect on R-M activity by introducing a chloramphenicol resistance cassette in the ClaI site at position 11 kbp, C: effect on R-M activity by deletion of the 1.2 kbp BclI fragment; D effect on R-M activity by introducing an erythromycin resistance cassette in the BglII site at position 9.2 kbp; and E: cloning of the 4.0 kbp HindIII fragment. Abbreviations: Bc, BclI; Bg, BglII, E, EcoRI; H, HindIII X, XhoI.

Cloning and localization of the LlaBI R-M system. Cell extracts from *L. lactis* W56, T1.1 [pJW563], T21.5 [pJW565] and T46.22 [pJW566] were screened for type II endonuclease activity. Only *L. lactis* W56 and the transformant T1.1 expressed type II activity, designated LlaBI. A restriction map of the plasmid pJW563 was made (FIG. 2). Direct cloning of the entire R-M system in *E. coli* in different vectors was not successful (data not shown). Therefor cloning of pJW563 was carried out in *L. lactis* MG1614. Due to problems in cloning the entire system in *L. lactis* MG1614 it was decided to determine the location of the genes for the R-M system on the plasmid pJW563. A chloramphenicol resistance cassette was inserted into one of the ClaI sites, resulting in the plasmid pJWC1 (data not shown). *L. lactis* MG1614[pJWC1] expressed R-M activity like the wild type plasmid. Bidirectional deletions were made showing that the R-M system was located around the BglII site (data not shown). An erythromycin cassette with compatible BamHI linker ends was inserted into the unique BglII site of pJW563, and the resulting plasmid, pJWE1, was electroporated into *L. lactis* MG1614 (FIG. 2). Cell lysate of the transformant did not express any LlaBI endonuclease activity and the transformant did not restrict phages. However, the transformant *L. lactis* MG1614[pJWE1] expressed methylase activity found by the fact that phages, propagated on the transformant, was not restricted by transformants containing pJW563. Deletion of the 1.2 kbp BclI fragment from pJWEI resulted in plasmid pJWE2, which showed neither endonuclease nor methylase activity (FIG. 2). These results indicated that the endonuclease gene was located near the BglII site, whereas at least a part of the methylase gene was located on the 1.2 kbp BclI fragment. The entire R-M system was then cloned in the vector pSA3 on a 4.0 kbp HindIII fragment containing the BglII and BclII sites, resulting in the plasmid pSNB1. Crude cell extracts prepared from *L. lactis* MG1614[pSNB1] transformants expressed LlaBI endonuclease activity (data not shown) and restricted phage jj50 with an (EOP) of $10^{-4}$ and phage c2 with and EOP of $10^{-3}$. Phage jj50 propagated on *L. lactis* MG1614[pSNB1] was not restricted by the *L. lactis* MG1614[pJW563] strain, indicating that phage jj50 DNA had been methylated, suggesting that the plasmid pSNB1 carried the genes encoding both the endonuclease and methylase from the LlaBI R-M system and that they function as a phage resistance mechanism. It was not possible to transform *E. coli* HB 101 with the plasmid pSNB1, which harboured the HindIII-fragment cloned in pSA3, indicating that the entire LlaBI R-M system is lethal to *E. coli*. The LlaBI encoding genes were also cloned as a 6.4 kbp EcoRI fragment from pJW563 in a BluescriptIISK+ derivative carrying a cassette encoding chloramphenicol resistance and a replicon from pJW565, resulting in plasmid pAG55. *L. lactis* MG1614[pAG55] restricted phage jj50 at the same order of magnitude as the wild-type plasmid pJW563.

Deposit. *Lactococcus lactis* subsp. *lactis* MG1614 transformed with plasmid pAG55 comprising the LlaBI R-M system has been deposited at the Belgian Coordinated Collections of Microorganisms (BCCM), Laboratorium voor Microbiologie—Bacteriënverzameling (LMG), Universiteit Gent, Belgium, under the accession number LMG P-15719.

Gene organization and DNA sequence. It was not possible to clone the 4.0 kbp HindIII fragment in pBluescriptIISK+ in *E. coli* XL1-Blue, indicating again that the endonuclease expression may be lethal to *E. coli*. Several of the clones were deleted in one direction as described in Materials and Methods. The nucleotide sequence of the 4.0 kbp HindIII fragment containing the LlaBI R-M genes was determined on both strands. Two major ORFs, ORF1 and ORF2, were found in the sequence (SEQ ID No. 9): ORF1 comprised 1740 bp, with a coding potential for a 580 aa protein, and ORF2 comprised 897 bp, capable of coding for a 299 aa protein. The two ORFs were separated by 302 bp and transcribed divergently. Both ORFs were preceded by putative Shine-Dalgarno sequences 7 bp in front of the ATG start codon. Putative −10 (sequence TATAAT and TATAAG) and −35 (sequence TTGACT and TCGTAA) consensus regions were found upstream of both ORFs. The sequenced region had only one BglII site, and it was located 138 bp downstream of the putative start codon in ORF2. This BglII site was inactivated in plasmids pJWE1 and pJWC1, which did not express endonuclease activity, showing that ORF2 codes for the LlaBI endonuclease. The 1.2 kbp BclI fragment, which was deleted in plasmid pJWE2 (FIG. 2), was found at position 1305 to 2520 covering 856 bp downstream in ORF1, showing that ORF1 codes for the methylase, M,LlaBI. A secondary structure indicating a putative terminator loop was found downstream of the methylase gene with a 2 bp overlap. The results show that the LlaBI R-M system consists of a methylase, M-LlaBI, putative of a 580 aa protein (65 kDa) and an endonuclease, R.LlaBI, putative of a 299 aa protein (33 kDa), transcribed divergently.

The r.llaBI gene is preceded by one short ORF, which extends over 90 bp and may code for a small protein of 30 amino acids. This ORF is aligned in the same orientation as the r.llaBI gene and separated therefrom by 110 bp.

Comparison of amino acid sequences. No primary sequence similarities were found between the restriction endonuclease R.LlaBI and the corresponding methylase M.LlaBI, or with other type II restriction endonucleases. The deduced amino acid sequence of the M.LlaBI methylase was compared with the amino acid sequence of other methylases in the data banks. The motif II, DhVhXDPPYh, which is common to all known adenine and cytosine methylases (29) was found in the sequence from nucleotide 1717 to 1688. The sequence lacked the motifs common to cytosine methylases (30). A motif similar to motif III (21), which is associated with adenine methylases like Eco57 1, PstI, PaeR71 and BsuBI, recognizing the sequence CTxxAG, was also found in LlaBI. Since these comparisons of the amino acid sequence of the M.LlaBI methylase to other type II methylases revealed a significant similarity to N6-adenine methylases and a lack of the numerous conserved motifs common to cytosine methylases, the M.LlaBI methylase most likely is a N6-adenine methylase.

Discussion

The R-M coding plasmid, pJW563, isolated from *L. lactis* W56, was previously reported to restrict the isometric headed phage jj50 with an efficiency of plating (EOP) of $10^{-3}$ and the prolate headed phage with an EOP of $10^{-2}$, clearly showing that it encodes a phage resistance mechanism (23). The system exhibiting type II endonuclease activity, designated R.LlaBI, was purified and its recognition sequence determined to be 5'-C↓TRYAG-3' (34). Two plasmids, pSNB1 and pAG55, harbouring the genes encoding the LlaBI R-M system, have been constructed. In *L. lactis* MG1614 the plasmids pSNB1 and pAG55 had the ability to restrict lactococcal phages with an EOP at the same level as found for the wild-type plasmid, pJW563. This showed that the genes can be cloned and used to increase the phage resistance in Lactococcus strains.

By cloning and sequencing the LlaBI R-M system, it was found that the R-M system consists of two ORFs putatively transcribed divergently. The methylase is encoded by an ORF of 1740 bp capable to code for a protein of 580 amino acid, while the putative endonuclease is encoded by an ORF of 897 bp capable to code for a protein of 299 amino acids. The size of the methylase (65 kDa) is considerably larger than most of the sequenced methylases, indicating that the M.LlaBI methylase may be a monomer. The deduced size of the restriction endonuclease (33 kDa) is comparable to the sizes of other endonucleases (51). Probably the endonuclease functions as a dimer like many other type II endonucleases. The missing primary sequence similarities between the M.LlaBI and the corresponding R.LlaBI supports the general assumption that type II restriction endonucleases and methylases are evolutionary unrelated and interact with target DNA sequences by different mechanisms (49).

Preceding the r.llaBI gene was a small ORF (90 bp) potentially encoding a protein of 30 amino acids. Probably this protein is too small to act as a trans-acting positive regulator of the r.llaBI gene, similar to pvuIIC, found in the PvuII system (43) and other systems with divergently transcribed genes.

The motif II is presumably involved in the general steps of DNA methylation, probably in the transfer of the methyl group (29). The structural similarity of the methylases recognizing the sequence CTXXAG suggests that motif III may be involved in the sequence recognition of the methylases. From cytosine methylases, however, experimental evidence suggests that the large amount of conserved motifs (29) may be involved in the proper folding of the protein, while the variable regions may be responsible for sequence specificity (35). It cannot be excluded that motif III is involved in the folding of the methylases.

During the cloning of the LlaBI system it was found that the plasmid pJW563 was resistant to digestion by the PstI restriction endonuclease (data not shown) although subclones of pJW563 containing fragments of the M.LlaBI methylase were not resistant to PstI restriction. The PstI endonuclease recognises 5'-CTGCA↓G-3' and cuts as indicated by the arrow. LlaBI can recognise the same sequence, 5'-C↓TGCAG-3' (and 5'-C↓TATAG-3'), but will cut the recognition sequence at a different place (LlaBI generates 5'-overhangs while PstI gives 3'-overhangs). This indicates, that the adenine in the PstI recognition sequence has been methylated by the M.LlaBI methylase. This result, together with the homology found between the M.LlaBI methylase and other adenine methylases, and the lack of homology to common motifs in cytosine methylases, indicate that the M.LlaBI methylase is a N6-adenine methylase.

The average G+C content of the LlaBI genes is 27,8% (31,5% for the r.llaBI and 25,7% for m.llaBI), which is much lower than the 34 to 43% G+C content normally found in lactococci by measuring the melting temperature (40). This may indicate that the LlaBI R-M system originates from genus other than Lactococcus.

EXAMPLE 3

*L. lactis* W39 has previously been isolated from the Danish mixed Cheddar starter, TK5 (33). We found, as shown in Table 2, that *L. lactis* W39 expressed type II endonuclease activity, which we designated LlaDI. Here we report the cloning and nucleotide sequence of the genes coding for another type II R-M system from *L. lactis* W39, designated LlaDII, with an endonuclease having a different restriction pattern from that of LlaDI.

Materials and Methods

Strains, phages, plasmids and growth conditions. The strains and bacteriophages used in this study are listed in Table 7. The *L. lactis* strains were grown at 30° C. in M17 media (Oxoid) supplemented with 0,5% glucose (GM17) and 5 mM $CaCl_2$ when phages were used. *Escherichia coli* (*E. coli*) strains were grown at 37° C. in LB. The antibiotics (Sigma) were used at the following concentrations: in *L. lactis:* chloramphenicol, 6 µg/ml; in *E. coli:* chloramphenicol, 20 µg/ml; tetracycline, 12,5 µg/ml; and ampicillin, 100 µg/ml. Lactococcal phage propagation and plaque assays were carryed out as described by Terzaghi and Sandine (44). The plasmids used in this study are shown in Table 8.

TABLE 7

Bacterial strains and bacteriophages used

| Bacterial strain or phage | Relevant characteristics | Reference or source |
| --- | --- | --- |
| *L. lactis* subsp. cremoris: | | |
| W39 | industrial strain, multiple plasmids | E. Waagner Nielsen (22) |
| MG1614 | plasmid-free, host for jj50, p2 and c2 phages; transformation host. | A. von Wright (12) |
| LM2301 | plasmid-free, host for jj50, p2 and c2 phages; transformation host. | Stephen Wessels (48) |
| *E. coli:* | | |
| XL1-Blue MRF Phages: | Transformation host | Strategene |
| jj50 | Small isometric headed, 936 species | (23) |
| p2 | Small isometric headed, 936 species | T. R. Klaenhammer |
| c2 | Prolate headed, c2 species | T. R. Klaenhammer (25) |

TABLE 8

Plasmids used in this study.

| Plasmid | Relevant characteristics | Reference or source |
| --- | --- | --- |
| pHW393 | r+/m+ | this work |
| pCI3340 | shuttle vector | (15) |
| pVS2 | shuttle vector | (53) |
| pBluescript II SK+ | | Stratagene |
| pSA3 | plasmid | Dao and Ferretti (7) |
| pCAD1 | pCI3340::2.4 kb PstI-EcoRI | this work |
| pCAD2 | pCI3340::5.4 kb XbaI-EcoRI | this work |
| pSAD1 | pBluescriptIISK+::0.9 kb PstI-XhoI | this work |
| pSAD2 | pBluescriptIISK+::1.5 kb XhoI-EcoRI | this work |

Preparation of cell extracts. A 1 l fresh over-night culture of *L. lactis* was harvested and washed once in 10 ml cold lysis buffer (50 mM Tris-HCl pH 7.6, 10 mM $MgCl_2$, 25 mM NaCl, 7 mM mercaptoethanol) and suspended in 12–15 ml cold lysis buffer. A French press (Aminco, USA) was used to disrupt the cells at 1500 psi. The crude extracts were centrifugated for 2 hrs at 180 000×g before glycerol was added to the supernatant to a final concentration of 20%. Aliquots of the extract were stored at −20° C.

Determination of endonuclease activity. Type II endonuclease activity in vitro was determined by incubating cell extract or partially purified enzyme with plasmid DNA in NEBuffer 2 (10 mM Bis-Tris-propane-HCl pH 7.0, 10 mM $MgCl_2$, 1 mM DTT) from Biolabs (New England, USA). After 1 hr incubation at 37° C., the reaction mixture was analyzed by electrophoresis in agarose gel with TAE buffer (37). The in vivo endonuclease activity was determined as an average of three independent determination of the efficiency of plating (EOP) performed as described earlier (23).

Purification of restriction endonucleases. Cell extract, made as described, was purified by an one-step FPLC chromatographic procedure using a Mono Q column in buffer A (50 mM Tris-HCl pH 7.6, 10 mM $MgCl_2$, 5 mM mercaptoethanol). The enzyme was eluted with 1 M KCl in buffer A and collected in small fractions, which were assayed for endonuclease activity.

Determination of methylase activity. Plasmid DNA was incubated with purified LlaDII endonuclease as described above. Methylase activity was observed if the plasmid DNA encoding the methylase was protected against cleavage with the purified LlaDII endonuclease. In vivo LlaDII methylase activity was determined by plaque assays.

Transformation. *L. Lactis* LM2301 was grown with 3% glycine and transformed by electroporation using a Bio-Rad Gene Pulser apparatus (Bio-Rad Laboratories, Richmond, USA) as described by Holo and Nes (19). *E. coli* strains were transformed by the $CaCl_2$ standard procedure (37).

DNA isolation and cloning. Plasmid DNA was extracted from *L. lactis* strains by the method of Andresen et al (1) and purified by the CsCl gradient method (37). Plasmid DNA isolation from *E. coli* was performed by alkaline lysis and CsCl gradient method (37) or by QIAGEN columns (QIAGEN Inc., Chatsworth, USA). Restriction endonucleases, T4 ligase, and Calf Intestine Alkaline Phosphase (CIP) were purchased from Boehringer Mannheim (Mannheim, Germany), Amersham (Buckinghamshire, UK) or New England Biolabs (Beverly, USA). All enzymes and kits were used according to the manufacturers recommendations.

DNA sequencing. Double-stranded DNA templates for sequencing were obtained by subcloning various DNA fragments in pBluescript II SK+. Deletions of the entire fragments were obtained by using the 'Erase-a-base' system (Promega Corp., Madison, USA). The nucleotide sequence was determined by standard dideoxy sequencing using Auto Read™ Sequencing kit (Hoefer Pharmacia Biotech Inc., San francisco, USA). The fragments were sequenced on both strands using universal and reverse primers (Stratagene). Computer analyses were performed with the GCG sequence analysis program (Version 8.0) (10).

Sequence comparisons. The sequence of the LlaDII genes was compared with R-M genes from the NCBI database.

Results

Identification of a plasmid encoding the LlaDII R-M system. Total plasmid DNA from *L. lactis* W39 was cotransformed with pVS2 into *L. lactis* MG1614 selecting for chloramphenicol resistance (23). The phage sensitivity of the transformants were determined by crossstriking with phage jj50. It was found that cell extract from transformant *L. lactis* 39.26, which harboured plasmid pHW393 besides pVS2, expressed type II endonuclease activity designated LlaDI. *L. lactis* 39.26 restricted the small isometric headed phages jj50 and p2 with an efficiency of plating (EOP) of $10^{-4}$ and the prolate headed phage c2 with an EOP of $10^{-2}$. Phages propagated on the transformant circumvented the restriction, showing that plasmid pHW393 encodes a R-M system. The transformant 39.26 was cured for plasmid pVS2 by treatment with novobiocin, and pHW393 was retransformed into *L. lactis* LM2301. This transformant T39.3 restricted the phages jj50, p2 and c2 with the same EOP as tranformant 39.26.

Figure 3:
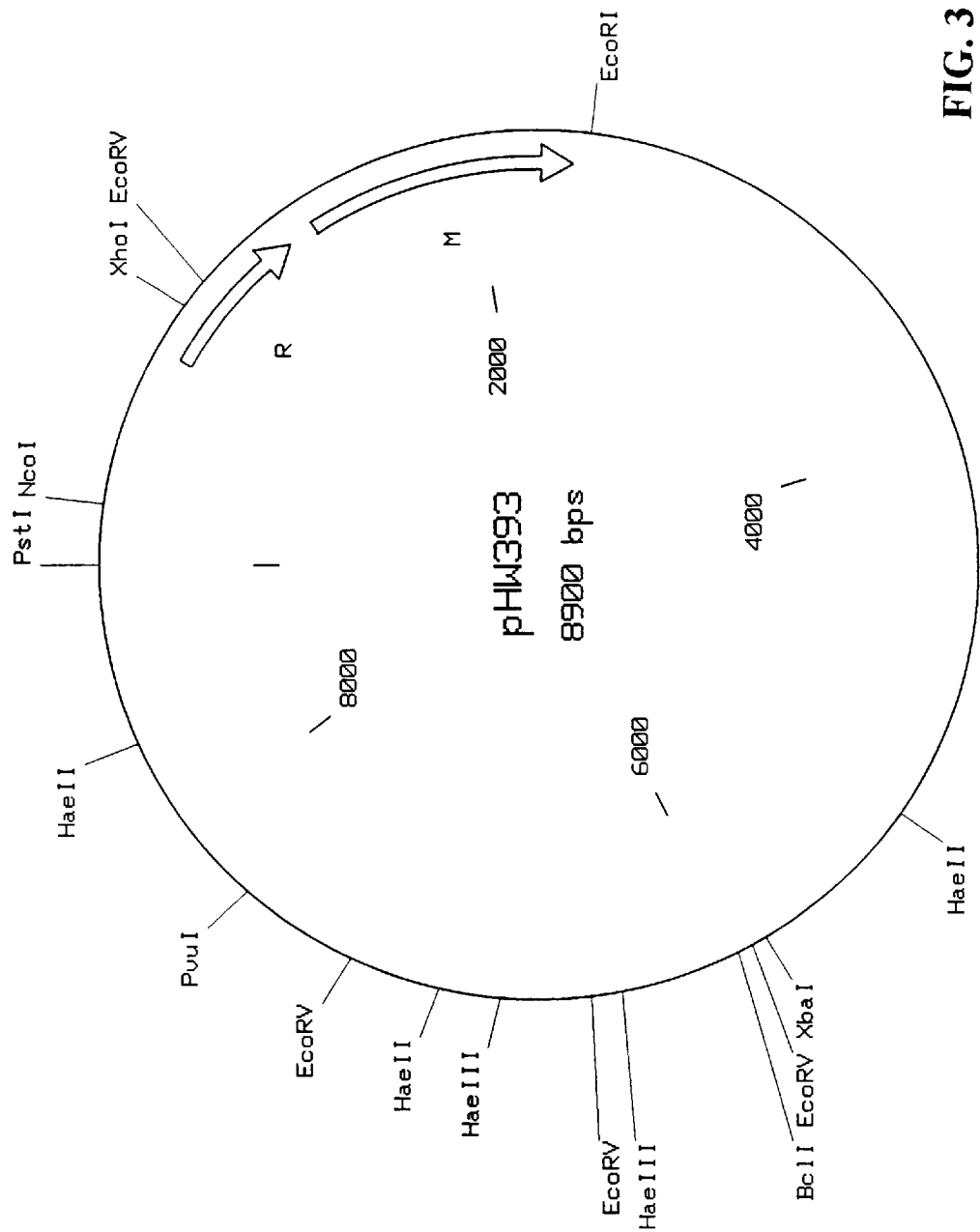
FIG. 3. Restriction map of plasmid pHW393.

Cloning and localization of the LlaDII R-M system. A restriction map of the plasmid pHW393 was made (FIG. 3). Two plasmids, designated pCAD1 and pCAD2, containing a 2.4 kbp PstI-EcoRI fragment and a 5.4 kbp XbaI-EcoRI fragment, respectively, in the shuttle vector pCI3340, were constructed and transformed into *L. lactis* LM2301. Both transformants restricted phages jj50 and p2 with an EOP of $10^{-3}$. Phages propagated on transformant *L. lactis* LM2301 [pCAD1] circumvented the restriction, showing that plasmid pCAD1 encodes a R-M system, which was designated LlaDII. It was only possible to transform *E. coli* XL 1-Blue MRF' with plasmid pCAD1; when plasmid pCAD2 was used for transformation only deleted plasmids were obtained.

Deposit. *Lactococcus lactis* subsp. *cremoris* LM2301 transformed with plasmid pCAD1 comprising the LlaDII R-M system has been deposited at the Belgian Coordinated Collections of Microorganisms (BCCM), Laboratorium voor Microbiologie—Bacteriënverzameling (LMG), Universiteit Gent, Belgium, under the accession number LMG P-16901.

Figure 4:
FIG. 4. Agarose gel (0,8%) showing the restriction patterns obtained by cleaving different DNA with: BsoFI (lane 1 and 3) and LlaDII (lane 2 and 4). Lanes 1 and 2: pSA3; Lanes 2 and 4: pBluescript IISK+.

Determination of the recognition site. The restriction endonuclease, LlaDII, of the transformant *L. lactis* LM2301 [pCAD1] was partially purified from cell extract. The restriction patterns of λ DNA digested with the endonucleases from *L. lactis* LM2301 [pCAD1] and *L. lactis* 39.26 were different from each other (data not shown). When pBluescript IISK+ and pSA3 were digested with the LlaDII and BsoFI restriction endonucleases identical restriction pattern were obtained (FIG. 4), showing that the restriction endonucleases LlaDII and BsoFI expressed the same type II activity and are isoschizomers. BsoFI recognized and cleaved the sequence 5'-GC↓NGC-3' (31).

Gene organization and DNA sequence. The PstI-EcoRI fragment was subcloned as PstI-XhoI and XhoI-EcoRI fragments in pBluescript II SK+ resulting in plasmids pSAD1 and pSAD2, respectively. Deletions were made as described in Materials and Methods. The nucleotide sequence of the 2.4 kb fragment revealed 2 major open reading frames (ORFs) (SEQ ID No. 12). ORF1 was putatively 540 bp with a coding potential for a protein of 180 amino acids (SEQ ID No. 13), and ORF2 was 951 bp capable of coding for a protein of 316 amino acids (SEQ ID No. 14). The two ORFs are separated by 108 bp and arranged tandemly with ORF1 preceding ORF2. ORF2 was preceded by a putative Shine-Dalgarno sequence with good identity to consensus, 8 bp in front of the ATG start codon. Plasmid pSAD2, harbouring only ORF2, was resistent to digestion by the LlaDII endonuclease, showing that ORF2 had its own promotor and encodes a methyltransferase, which can be expressed in *E. coli* (data not shown). The results show that the LlaDII R-M system consists of two consecutively transcribed genes, where ORF2 carry the gene for a methyltransferase, M.LlaDII.

Comparison of amino acid sequences. The deduced amino acid sequences of ORF1 and ORF2 were compared with the amino acid sequences of other methylases in the databases. The first ten amino acids encoded by the putative ORF1 may be doubtful as the sequencing first gave base no. 744 in SEQ ID No 12 as TT. However, from base no. 773 this reading frame gives a high homology with the endonuclease of the Bsp6I R-M system. The deduced amino acid sequence of ORF2 showed 60% identity and 76% similarity to the methylase from the Bsp6I R-M system (31) and it contained several amino acid sequence motifs characteristic for C-5-cytosine methyltransferases (50). This also indicates that ORF2 codes for a C-5-cytosine methyltransferase.

Discussion

The 8.9 kb naturally occurring plasmid pHW393 was isolated from *L. lactis* W39. Transformants *L. lactis* LM2301 [pHW393] and *L. lactis* LM2301 [pCAD1] were both able to restrict phages and this restriction was circumvented by propagation of surviving phages on the respective transformants, showing that plasmid pHW393 and the 2.4 kbp PstI-EcoRI fragment in pCAD1 both code for a restriction/modification system, and that both plasmids can be used to increase the level of phage defence in *Lactococcus lactis*. The 2.4 kbp PstI-EcoRI fragment cloned in pCI3340 had in Lactococcus the ability to restrict lactococcal phages with one order of magnitude lower EOP than found for the wild-type plasmid, pHW393, indicating that the expression of the cloned LlaDII R-M system may be depending of the plasmid copy number, or it may require some additional factors or that there are two R-M systems present on plasmid pHW393. Since plasmid pHW393 was found to express LlaDI endonuclease activity, and plasmid pCAD1 containing the 2.4 kb PstI-EcoRI fragment thereof expresses LlaDII activity, plasmid pHW393 must encode two type II R-M systems. This is the first time that two type II R-M systems have been found on the same plasmid.

The 2.4 kbp PstI-EcoRI fragment harbours two tandemly arranged genes, LlaDIIR and LlaDIIM, which encode a restriction endonuclease and a C-5-cytosine methyltransferase, respectively. The R.LlaDII gene precedes the M.LlaDII gene and they are separated by 108 bp. Since plasmid pSAD2 harbouring only the M.LlaDII gene expressed methylase activity in *E. coli*, these genes are most likely transcribed as two monocistronic mRNAs.

The endonuclease of the LlaDII R-M system is an isoschizomer of BsoFI recognizing the sequence 5'-GC↓NGC-3', showing that the LlaDII R-M system is a type II system. This is the first time a R-M system, which recognizes the sequence 5'-GC↓NGC-3', has been identified and cloned in *Lactococcus lactis*.

REFERENCES

1. Andresen, A., A. Geis, U. Krusch, and M. Teuber. Plasmidmuster milchwirtschaftlich genutzter Starterkulturen. Milchwissenschaft 39 (1984): 0–143.

2. Bickle, T. A. and Krüger, D. H.: Biology of DNA restriction. Microbiol. Rev. 57 (1993): 434–450.

3. Boyer, H. W., and Roulland-Dussoix, D.: A complementation analysis of the restriction and modification of DNA in *Escherichia coli*. J. Mol. Biol. 41 (1969): 459.

4. Cerritelli, S., S. S. Springhorn, and S. A. Lacks: DpnA, a methylase for single-strand DNA in the DpnII restriction system, and its biological function. Proc. Natl. Acad. Sci. USA 86 (1989): 9223–9227.

5. Chopin, A., Chopin, M.-C., Moillo-Batt, A. and Langella, P.: Two plasmid-determined restriction and modification systems in *Streptococcus lactis*. Plasmid 11 (1984): 260–263.

6. Daly, C. and Fitzgerald, G. F.: Mechanisms of bacteriophage insensitivity in the lactic streptococci. In: Ferretti, J. J. and Curtis III, R.(Eds.), Streptococcus Genetics. American Society for Microbiology, Washington, D.C., 1987, pp. 259–268.

7. Dao, M. L. and Ferretti, J. J.: Streptococcus-*Escherichia coli* shuttle vector pSA3 and its use in the cloning of streptococcal genes. Appl. Environ. Microbiol. 49 (1985): 115–119.

8. Davis, R., van der Lelie, D., Mercenier, A., Daly, C. and Fitzgerald, G. F.: ScrfI restriction-modification system of *Lactococcus lactis* subsp. *cremoris* UC503: cloning and characterization of two ScrFI MTase genes. Appl. Environ. Microbiol. 59 (1993): 777–785.

9. de la Campa, A. G, Kale, P., Springhorn, S. S. and Lacks, S. A.: Proteins encoded by the DpnII restriction gene cassette. Two methylases and an endonuclease. J. Mol. Biol. 196 (1987): 457469.

10. Devereux, J., P. Haeberli and O. Smithies: A comprehensive set of sequence analysis programs for the VAX. Nucl. Acids Res. 12 (1984): 387–395.

11. Fitzgerald, G. F., Daly, C., Brown, L. R. and Gingeras, T. R.: ScrFI, a new sequence-specific ENase from *Streptococcus cremoris*. Nucleic Acids Res. 10 (1982): 8171–8179.

12. Gasson, M. J.: Plasmid complements of *Streptococcus lactis* NCDO 712 and other lactic streptocci after protoplast-induced curing. J. Bacteriol. 154 (1983): 1–9.

13. Gautier, M., and Chopin, M.-C.: Plasmid-determined systems for restriction and modification activity and abortive infection in *Streptococcus cremoris*. Appl. Environ. Microbiol. 53 (1987): 923–927.

14. Gordon, J.-J., Delome, C., Ehrlich, S. D., and Renault, P.: Divergence of genome sequences between *Lactococcus lactis* subsp. *lactis* and *Lactococcus lactis* subsp. *cremoris*. Appl. Environ. Microbiol. 58 (1992): 4045–4047.

15. Hayes, F, Daly, C., and Fitzgerald, G. F.: Identification of the minimal replicon of *Lactococcus lactis* subsp. *lactis* UC317 plasmid pCI305. Appl. Environ. Microbiol. 56 (1990): 202–209.

16. Higgins, D. L., Sanozky-Dawes, R. B. and Klaenhammer, T. R.: Restriction and modification activities from *Streptococcus lactis* ME2 are encoded by a self-transmissible plasmid, pTN20, that forms cointegrates during mobilization of lactose-fermenting ability. J. Bacteriol. 170 (1988): 3435–3442.

17. Hill, C., Pierce, K. and Klaenhammer, T. R.: The conjugative plasmid pTR2030 encodes two bacteriophage defense mechanisms in lactococci, restriction modification ($R^+/M^+$) and abortive infection ($Hsp^+$). Appl. Environ. Microbiol. 55 (1989): 2416–2419.

18. Hill, C., Miller, L. A. and Klaenhammer, T. R.: In vivo genetic exchange of a functional domain from a type II A methylase between lactococcal plasmid pTR2030 and a virulent bacteriophage. J. Bacteriol. 173 (1991): 4363–4370.

19. Holo, H. and Nes, I. F.: High-frequency transformation, by electroporation, of *Lactococcus lactis* subsp. *cremoris* grown with glycine in osmotically stabilized media. Appl. Environ. Microbiol. 55 (1989): 3119–3123.

20. Janulaitis, A., Petrusyte, M., Maneliene, Z., Klimasauskas, S. and Butkus, V.: Purification and properties of the Eco57I restriction endonuclease and methylase-prototypes of a new class (type IV). Nucleic Acids Res. 20 (1992): 6043–6049.

21. Janulaitis, A., Vaisvila, R., Timinskas, A., Klimasauskas, S., and Butkus, V.: Cloning and sequence analysis of the genes coding for Eco57I type IV restriction-modification enzymes. Nucleic Acids Res. 20 (1992): 6051–6056

22. Josephsen, J. and Nielsen, E. W.: Plasmid profiles and bacteriophage sensitivity of bacteria of a Cheddar starter used for five years without rotation. Milchwissenschaft 43 (1988): 219–223.

23. Josephsen, J. and Vogensen, F. K.: Identification of three different plasmid encoded restriction/modification systems in *Streptococcus lactis* subsp. *cremoris* W56. FEMS Microbiol. Lett. 59 (1989): 161–166.

24. Josephsen, J. and Klaenhammer, T. R.: Stacking of three different restriction and modification systems in *Lactococcus lactis* by cotransformation. Plasmid 23 (1990): 71–75.

25. Keogh, B. P. and Shimmin, P. D.: Morphology of the bacteriophages of lactic streptococcal bacteriophages. Appl. Microbiol. 27 (1974): 411–415.

26. Klaenhammer, J. R.: Plasmid-directed mechanisms for bacteriophage defense in lactic streptococci. FEMS Microbiol. Rev. 46 (1987): 313–325.

27. Klaenhammer, T. R. and Fitzgerald, G. F.: Bacteriophages and bacteriophage resistance. In: M. G. Gasson and W. M. de Vos (Eds.), Genetics and Biotechnology of Lactic Acid Bacteria. Blackie, London, 1994, pp. 106–168.

28. Lacks, S. A., Mannarelli, B. M., Springhorn, S. S., and Greenberg, B.,: Genetic basis of the complementary DpnI and DpnII restriction systems of *S. pneumoniae*: An intercellular cassette mechanism. Cell 46 (1986): 993–1000.

29. Lauster, R.: Evolution of Type II DNA Methytransferases, J. Mol.Biol, 206 (1989): 313–321

30. Lauster, R., Trautner, T. A., and Noyer-Weidner, M.,: Cytosine-specific Type II DNA Methyltransferases. A conserved enzyme core with variable target-recognizing domains. J. Molecular Biology 206 (1989): 305–312.

31. Lubys, A., and Janulaitis, A.: Cloning and analysis of the plasmid-borne genes encoding the Bsp6I restriction and modification enzymes. Gene 157 (1995): 25–29.

32. Mayo, B., C. Hardisson and A. F. Brana. Nucleolytic activities in *Lactococcus lactis* subsp. *lactis* NCDO 497. FEMS Microbiol. Lett. 79 (1991): 195–198.

33. Nielsen, E. Waagner, Josephsen, J. and Vogensen, F. K.: Lactic starters—improvement of bacteriophage resistance and application of DNA-technology. Danish J. Agro. Special Issue March 1987, 35–45.

34. Nyengaard, N., Vogensen, F. K. and Josephsen, J.: LlaAI and LlaBI, two type-II restriction endonucleases from *Lactococcus lactis* subsp. *cremoris* W9 and W56 recognizing, respectively, 5'-/GATC-3 and 5'-C/TRYAG-3'. Gene 136 (1993): 371–372.

35. Pósfai, J., Bhagwat, A. S., Pósfai, G., and Roberts, R. J.: Predictive motifs derived from cytosine methyltransferases. Nucleic. Acids Res. 17 (1989): 2421–2435.

36. Roberts, R. J.: Restriction enzymes and their isoschizomers. Nucleic Acids Res. 18 (1990): 2331–2365

37. Sambrook, J., Fritsch, E. F. and Maniatis, T. Molecular Cloning: A Laboratory Manual, 2nd. ed., Cold Spring Harbor University Press, Cold Spring Harbor, 1989.

38. Sanders, M. A.: Phage resistance in lactic acid bacteria. Biochimie 70 (1988): 411–421.

39. Sanger, F., S. Nickelsen and A. R. Coulson: DNA sequencing with chain terminating inhibitors. Proc. Natl. Acad. Sci. 82 (1977): 1074–1078.

40. Schleifer, K. H., Kraus,J., Dvorak, C., Kilpper-Bälz, R., Collins, M. D., Fischer, W., Transfer of *Streptococcus lactis* and related streptococci to the genus Lactococcus gen. nov. System. Appl. Microbiol. 6 (1985): 183–195.

41. Sing, W. D. and Klaenhammer, T. R.: Characterization of restriction-modification plasmids from *Lactococcus lactis* ssp. *cremoris* and their effect when combined with pTR2030. J. Dairy Sci. 74 (1991): 1133–1144.

42. Sing, W. D. and Klaenhammer, T. R.: A strategy for rotation of different bacteriophage defenses in a lactococcal single-strain starter culture system. Appl. Environ. Microbiol. 59 (1993): 3429–3443.

43. Tao, T., and Blumenthal, R. M.: Sequence and characterization of pvuIIR, the PvuII endonuclease gene, and of pvIIC, its regulatory gene. J. Bacteriol. 174 (1992): 3395–3398.

44. Terzaghi, B. E., and W. E. Sandine. Improved medium for lactic streptococci and their bacteriophages. Appl. Microbiol. 29 (1975): 807–813.

45. Twomey, D. P., Davis, R., Daly, C., and Fitzgerald, G. F.: Sequence of the gene encoding a second ScrFI m$^5$C methyltransferase of *Lactococcus lactis*. Gene 136 (1993): 205–209.

46. Tynkkynen, S., Buist, G., Kunji, E., Kok, J., Poolman, B., Venema, G., and Haandrikman, A. J.: Genetic and biochemical characterization of the oligopeptide transport system of *Lactococcus lactis*. J. Bacteriol. 175 (1993): 7523–7532.

47. Ueno, T., Ito, H., Kimizuka, F., Kotani, H. and Nakajima, K; Gene structure and expression of the MboI restriction—modification system, Nucleic Acids Research, 21 (1993): 2309–2313.

48. Walsh, P. M., and McKay, : Recombinant plasmid associated with cell aggregation and high frequency conjugation of *Streptococcus lactis* ML3. J. Bacteriol. 146 (1981): 937–944.

49. Wilson, G. G.: Organization of restriction-modification systems. Nucleic Acids Res. 19 (1991): 2539–2566.

50. Wilson, G. G.: Amino acid sequence arrangements of DNA-methyltransferases. Methods in Enzymology 216 (1992): 259–279.

51. Wilson, G. G. and Murray, N. E.: Restriction and Modification system, Ann. Rev. Genet 25 (1991): 585–627.

52. Withers, B. E., Ambroso, L. A. and Dunbar, J. C.; Structure and evolution of the XcyI restriction-modification system, Nucleic Acids Research 20 (1992): 6267–6273.

53. von Wright, A., Tynkkynen, S. and Suominen, M.: Cloning of a *Streptococcus lactis* subsp. *lactis* chromosomal fragment associated with the ability to grow in milk. Appl. Environ. Microbiol. 53 (1987): 1584–1588.

What is claimed is:

1. A plasmid-derived type II restriction-modification (R-M) system, termed LlaDII, from *Lactococcus lactis* subsp. *cremoris* W39, said system encoding at least one methylase and a restriction endonuclease, characterized in that the system comprises
   i) an open reading frame, termed ORF1, from about nucleotide 743 to nucleotide 1282 in the enclosed SEQ ID No. 12, coding for a restriction endonuclease, termed R.LlaDII, having the amino acid sequence essentially as shown in the enclosed SEQ ID No. 13 and with the recognition sequence 5'-GC↓NGC-3', and
   ii) an open reading frame, termed ORF2, from nucleotide 1391 to nucleotide 2341 in the enclosed SEQ ID No. 12, coding for a methylase, termed M.LlaDII, having the amino acid sequence shown in the enclosed SEQ ID No. 14.

2. A DNA fragment coding for a restriction endonuclease, termed R.LlaDII, said fragment comprising the DNA sequence from nucleotide 743 to nucleotide 1282 in the enclosed SEQ ID No.12.

3. A DNA fragment coding for a methylase, termed M.LlaDII, said fragment comprising the DNA sequence from nucleotide 1391 to nucleotide 2341 in the enclosed SEQ ID No. 12.

4. A DNA cassette comprising the R-M system and DNA fragments according to any one of the preceding claims in combination with DNA encoding other phage resistance mechanisms selected from the group consisting of adsorption blocking, abortive infection and R-M systems.

5. A cloning vector including DNA of the R-M system according to claim 1 and a DNA cassette according to claim 4.

6. A cloning vector according to claim 5 which is the plasmid pCAD1 introduced in *Lactococcus lactis* subsp. *cremoris* LM2301 and deposited under the accession number LMG P-16901.

7. An expression vector including DNA of the R-M system according to claim 1 and a DNA cassette according to claim 4 under the control of a promoter capable of providing expression thereof in a host cell.

8. An expression vector according to claim 7 wherein said DNA is under the control of a promoter capable of providing expression thereof in a Gram-positive bacterium.

9. An expression vector according to claim 8 wherein said DNA is under the control of a promoter capable of providing expression thereof in a lactic acid bacterium.

10. An expression vector according to claim 9 wherein said DNA is under the control of a promoter capable of providing expression thereof in *Lactococcus lactis*.

11. A cloning vector including DNA selected from the group consisting of DNA fragments according to claims 2 and 3 and a DNA cassette according to claim 4.

12. A cloning vector according to claim 11 comprising the plasmid pCAD I introduced in *Lactococcus lactis* subsp. *cremoris* LM2301 and deposited under the accession number LMG P-16901.

13. An expression vector including DNA selected from the group consisting of DNA fragments according to claims 2 and 3 and a DNA cassette according to claim 4, under the control of a promoter capable of providing expression of said DNA in a host cell.

14. An expression vector according to claim 13 wherein said DNA is under the control of a promoter capable of providing expression of said DNA in a Gram-positive bacterium.

15. An expression vector according to claim 14 wherein said DNA is under the control of a promoter capable of providing expression of said DNA in a lactic acid bacterium.

16. An expression vector according to claim 15 wherein said DNA is under the control of a promoter capable of providing expression of said DNA in *Lactococcus lactis*.

17. A method of conferring increased virus resistance on a cell wherein said cell is transformed with an expression vector according to claim 7.

18. A method of conferring increased phage resistance on a Gram-positive bacterium wherein said bacterium is transformed with an expression vector according to claim 8.

19. A method of conferring increased phage resistance on a lactic acid bacterium wherein said bacterium is transformed with an expression vector according to claim 9.

20. A method of conferring increased phage resistance on a *Lactococcus lactis* strain wherein said strain is transformed with an expression vector according to claim 10.

21. A cell which carries an expression vector according to claim 7.

22. A Gram-positive bacterium which carries an expression vector according to claim 8.

23. A lactic acid bacterium which carries an expression vector according to claim 9.

24. A *Lactococcus lactis* strain which carries an expression vector according to claim 10.

25. A method of conferring increased virus resistance on a cell which comprises transforming said cell with an expression vector according to claim 13.

26. A method of conferring increased phage resistance on a Gram-positive bacterium which comprises transforming said bacterium with an expression vector according to claim 14.

27. A method of conferring increased phage resistance on a lactic acid bacterium which comprises transforming said bacterium with an expression vector according to claim 15.

28. A method of conferring increased phage resistance on a *Lactococcus lactis* strain which comprises transforming said strain with an expression vector according to claim 16.

29. A cell which carries an expression vector according to claim 13.

30. A Gram-positive bacterium which carries an expression vector according to claim 14.

31. A lactic acid bacterium which carries an expression vector according to claim 15.

32. A *Lactococcus lactis* strain which carries an expression vector according to claim 16.

33. A plasmid comprising the DNA sequence encoding the R-M system of claim 1.

34. A plasmid comprising the DNA sequence encoding the DNA cassette of claim 4.

35. A restriction endonuclease, termed R.LlaDII, with the recognition sequence 5'-GC↓NGC-3', said endonuclease having the amino acid sequence essentially as shown in the enclosed SEQ ID No. 13.

36. A methylase, termed M.LlaDII, having the amino acid sequence shown in the enclosed SEQ ID No. 14.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
       (A) LENGTH: 3695 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Lactococcus lactis subsp. cremoris
       (B) STRAIN: W9

(ix) FEATURE:
       (A) NAME/KEY: CDS
       (B) LOCATION:769..1620
       (C) IDENTIFICATION METHOD: experimental
       (D) OTHER INFORMATION:/codon_start= 769
           /product= "LlaAI -GATC- N-6-adenine methylase A"
           /evidence= EXPERIMENTAL
           /gene= "ORF"
           /number= 1
           /standard_name= "Gene coding for M.LlaAIA"
           /label= m-llaAIA (ix) FEATURE:
       (A) NAME/KEY: CDS
       (B) LOCATION:1613..2419
       (C) IDENTIFICATION METHOD: experimental
       (D) OTHER INFORMATION:/codon_start= 1613
           /product= "LlaAI -GATC- adenine methylase B"
           /evidence= EXPERIMENTAL
           /gene= "ORF"
           /number= 2
           /standard_name= "Gene coding for M.LlaAIB"
           /label= m-llaAIB (ix) FEATURE:
       (A) NAME/KEY: CDS
       (B) LOCATION:2412..3323
       (C) IDENTIFICATION METHOD: experimental
       (D) OTHER INFORMATION:/codon_start= 2412
           /product= "LlaAI restriction endonuclease"
           /evidence= EXPERIMENTAL
           /gene= "ORF"
           /number= 3
           /standard_name= "Gene coding for LlaAI restriction
           endonuclease"
           /label= r-llaAI (xi) SEQUENCE DESCRIPTION: SEQ ID NO: 1:

```
ATATAAGATA TATAAATCAG TTCGCCTTTT TCTACTCCGT TCTAAAATCT TAAAATCAAG      60

GTCAAAAGAA AAAGTCAAAA CCATTGAATT GAGGTTCTAA AATTAAACTC CCTGCGTTGC     120

TCTTGGCTGC CGCTTGTACA CTCTGATTTT ATATTAGATA CATTCTGCCA TTAAAAAGAA    180

CTCCTAACGG TCGTGGCTAC TTTGTTTAGT CTAAACGCTT TAAATAGTCC TACAAGCTCA    240

TATTTTGCCT TTTAAGCGAT TTTAAACGTG AGTTAGTAAT AATTATCATG GATAAAAGAA    300

AAAGCCCTTA AATAGGCTTG TATGTAATTG ACTAAAACGT ACAATTTAGC TTTTAAATAT    360

GACCCTTATT TATGACCTGC TCTAACCTCA CTATTCATCA GCATTCAAAA AAGAGGTCAA    420
```

```
                                                           -continued

AACTGTTAAG TTATGAGCTG AATAGATTTT ATTAAATTTT ATTTGGTTTA AAAGACCAAT      480

TATCTATTTT TTAACAAACA CTAAAATAGA TTTTTTGGAA AACTTTGCAA CAGAACCAGC      540

AATCTGATGT TGCGAGATGG ACGTTCTTTC GGTTTTGAAC CTCAAGGGGA ACACTCGTTT      600

GATAAAGCGT CTCAATGGTT GTCAGTAAAC AAACAAAAAC TTTTGGAAGT GTGCTATTAT      660

AAGTCATATA AGTCGTGCGC TTTCTAATGC TTAGTGCTTT AAGATTAGGA TAGCACGACT      720

TATTTATTTT CCAATAAAAT TAACTAGCAA TTCGGGTATA ATATATTT ATG AAT TTA      777
                                                    Met Asn Leu
                                                      1

TTA CAA AAA AAC AAG ATC AAC TTA CGT CCG TTT ACT AAA TGG ACA GGT      825
Leu Gln Lys Asn Lys Ile Asn Leu Arg Pro Phe Thr Lys Trp Thr Gly
      5                  10                  15

GGG AAA AGG CAA CTA CTG CCA CAC ATT CAA TAC CTA ATG CCA GAA AAA      873
Gly Lys Arg Gln Leu Leu Pro His Ile Gln Tyr Leu Met Pro Glu Lys
 20                  25                  30                  35

TAC AAT CAT TTT TTC GAA CCT TTT ATT GGT GGT GGC GCT TTG TTT TTT      921
Tyr Asn His Phe Phe Glu Pro Phe Ile Gly Gly Gly Ala Leu Phe Phe
                 40                  45                  50

GAA CTC GCT CCT CAA AAA GCA GTT ATT AAC GAC TTC AAT TCT GAG CTT      969
Glu Leu Ala Pro Gln Lys Ala Val Ile Asn Asp Phe Asn Ser Glu Leu
             55                  60                  65

ATA AAC TGT TAC CGG CAG ATG AAA GAT AAT CCT GAG CAA TTG ATA GAA     1017
Ile Asn Cys Tyr Arg Gln Met Lys Asp Asn Pro Glu Gln Leu Ile Glu
         70                  75                  80

TTG TTG ACT AAT CAT CAG CGG GAA AAT TCT AAA GAA TAT TAT TTA GAC     1065
Leu Leu Thr Asn His Gln Arg Glu Asn Ser Lys Glu Tyr Tyr Leu Asp
 85                  90                  95

TTA CGT TCT TCT GAT AGA GAT GGA AGA ATT GAT AAG ATG AGC GAA GTT     1113
Leu Arg Ser Ser Asp Arg Asp Gly Arg Ile Asp Lys Met Ser Glu Val
100                 105                 110                 115

GAA CGT GCT GCT AGA ATT ATG TAT ATG CTA CGT GTT GAT TTT AAT GGT     1161
Glu Arg Ala Ala Arg Ile Met Tyr Met Leu Arg Val Asp Phe Asn Gly
                120                 125                 130

TTA TAT CGT GTT AAT TCG AAA AAC CAG TTT AAT GTG CCT TAT GGA AGA     1209
Leu Tyr Arg Val Asn Ser Lys Asn Gln Phe Asn Val Pro Tyr Gly Arg
            135                 140                 145

TAT AAA AAT CCT AAG ATA GTT GAT AAA GAA TTG ATT GAA AGT ATT TCC     1257
Tyr Lys Asn Pro Lys Ile Val Asp Lys Glu Leu Ile Glu Ser Ile Ser
        150                 155                 160

GAG TAC TTG AAT AAC AAT TCT ATT AAG ATC ATG AGT GGA GAT TTT GAA     1305
Glu Tyr Leu Asn Asn Asn Ser Ile Lys Ile Met Ser Gly Asp Phe Glu
    165                 170                 175

AAA GCC GTT AAA GAA GCA CAG GAT GGA GAT TTT GTT TAT TTC GAC CCT     1353
Lys Ala Val Lys Glu Ala Gln Asp Gly Asp Phe Val Tyr Phe Asp Pro
180                 185                 190                 195

CCA TAC ATT CCA CTT TCT GAA ACT AGC GCC TTT ACT TCT TAT ACA CAC     1401
Pro Tyr Ile Pro Leu Ser Glu Thr Ser Ala Phe Thr Ser Tyr Thr His
                200                 205                 210

GAA GGC TTT AGC TAC GAA GAT CAA GTT AGG CTA AGA GAT TGT TTC AAA     1449
Glu Gly Phe Ser Tyr Glu Asp Gln Val Arg Leu Arg Asp Cys Phe Lys
            215                 220                 225

CAG TTA GAT TCA AAA GGG GTA TTC GTC ATG CTT TCA AAT TCT TCA AGC     1497
Gln Leu Asp Ser Lys Gly Val Phe Val Met Leu Ser Asn Ser Ser Ser
        230                 235                 240

CCT TTA GCG GAG GAA TTA TAT AAA GAT TTT TAC ATC CAT AAA ATT GAA     1545
Pro Leu Ala Glu Glu Leu Tyr Lys Asp Phe Tyr Ile His Lys Ile Glu
    245                 250                 255

GCT ACT CGA ACA AAT GGG GCT AAA TCA TCT AGT CGT GGA AAA ATC ACT     1593
```

```
Ala Thr Arg Thr Asn Gly Ala Lys Ser Ser Arg Gly Lys Ile Thr
260                 265                 270                 275

GAA ATC ATC GTA ACC AAT TAT GGC AAT TAACGAATAT AAGTATGGAG                1640
Glu Ile Ile Val Thr Asn Tyr Gly Asn
                280

GTGTTTTAAT GATAAAACCA TACTATGAAA AAGAAAACGC AATTCTCGTT CACGCAGATT        1700

CATTTAAATT ATTAGAAAAA ATTAAACCTG AAAGCATGGA CATGATATTT GCTGACCCTC        1760

CTTACTTTTT AAGTAATGGA GGAATGTCAA ATTCAGGTGG TCAAATTGTT TCTGTTGATA        1820

AAGGGGATTG GGATAAAATT TCTTCATTTG AAGAAAAACA TGACTTTAAT AGACGTTGGA        1880

TTAGGTTAGC AAGATTGGTT TTAAAACCCA ACGGAACTAT TTGGGTTTCC GGAAGCCTTC        1940

ATAACATATA TTCTGTCGGG ATGGCGCTGG AACAGGAAGG TTTCAAAATC TTAAATAATA        2000

TAACTTGGCA AAAGACAAAT CCTGCACCTA ATCTATCATG TCGGTACTTC ACCCACTCTA        2060

CAGAGACAAT TTTATGGGCA AGAAAGAACG ATAAAAAATC TCGCCATTAT TATAACTATG        2120

AATTGATGAA AGAGTTTAAT GACGGGAAAC AAATGAAAGA TGTTTGGACA GGTAGTCTGA        2180

CAAAAAAATC AGAAAAATGG GCTGGGAAAC ATCCAACTCA GAAGCCAGAG TATATTTTAG        2240

AACGGATAAT CTTAGCTAGT ACAAAGGAAA ATGATTATAT TTTAGACCCT TTCGTCGGAA        2300

GTGGAACTAC TGGTGTAGTA GCCAAGAGAT TGGGGCGTAA ATTTATTGGG ATTGATTCTG        2360

AGAAAGAATA TCTTAAAATT GCTAAAAAAA GGCTAAATAA AGGAGCAACA TATGGACTTT        2420

AATAATTACA TCGGTTTAGA ATCTGACGAT AGATTAAATG CTTTTATGGC AACACTTTCC        2480

GTAACTAATA GAACTCCCGA ATACTACGTG AACTGGGAAA AGTTGAACG TGAAACACGA         2540

AAATTTGAAT TAGAACTAAA TACTTTAAAC TATCTCATTG GGAAAGAAGA TATTTATAGT        2600

GAAGCACTTG AACTATTTAC CAATCAACCT GAATTGCTTA AAGCTATTCC TAGTTTGATT        2660

GCTAGTAGAG ATACATCTTT AGATATACTA ACATTGACG AAAATGATGA TATGAGTTTT        2720

GAACAACTTA ACTTTCTTGT TATCGACGAA AATTGTATCG CTGATTATGT AGACTTTATT        2780

AACCAGGCAG GTTACTAGA TTTTCTACAG AATAAAGCAA AACGTTCTCT GGTAGACTAT         2840

GTGTATGGTG TTGAAGCAGG GCTTGATAGC AATGCTCGAA AAACCGAAG CGGTACAACC         2900

ATGGAGGGGA TTTTAGAACG TACTGTTTCA AAAATAGCTC AAGAGAAAGG GCTTGAATGG        2960

AAGCCACAGG CAACCGCTTC TTTTATCAAG TCTCAATGGG ACATAGAAGT CCCTGTAGAC        3020

AAATCAAAAA GACGCTTTGA TGCAGCAGTT TACTCTCGTG CGCTCAATAA GGTTTGGCTC       3080

ATAGAAACAA ATTACTACGG CGGTGGAGGA AGTAAACTCA AAGCAGTTGC TGGAGAATTT       3140

ACAGAATTGA GTCAGTTTGT AAAAACATCA AAAGATAATG TTGAATTTGT ATGGGTAACA       3200

GACGGCCAAG GGTGGAAATT TTCCCGCTTA CCACTTGCAG AAGCTTTCGG ACACATCGAT       3260

AACGTTTTCA ATCTAACCAT GTTGAAAGAA GGTTTCTTGT CTGATTTATT CGAAAAAGAA       3320

ATTTAAAAAG ACAGAGAATC TCTGTCTTTT TAAATTTCAA TTCCTTCCTT CTGCTAGCTA       3380

TAACTTTCCA AAAACCTGA AAAACGGTTC TGTTGCAATT GTATGTGGGG TCGGAACTTA        3440

CTACTATATC ATGAGAAATG AAGATTAAAG TTGAAACAAA AAAACAGATT ATTTAAAAT        3500

GTAAATCTGT TTTTGTTTGG GCTGATTTTA TCACACCAAT TCTATGTTCA GAAAATGGTC       3560

ATTTTCTGGA CACTCTTCTT TTGTTATTAA AACTCTCAAA ATCATTTACA TTTATTGTTC       3620

ATTAACCCAT AATTTATTCT ATGTTCATTT ATAGATATCG AATTCCTGCA GGGCCCTCCA       3680

CTAGTTCTAG AGGCG                                                         3695
```

(2) INFORMATION FOR SEQ ID NO: 2:

(i) SEQUENCE CHARACTERISTICS:
    (A) LENGTH: 284 amino acids
    (B) TYPE: amino acid
    (D) TOPOLOGY: linear (ii) MOLECULE TYPE: protein (xi) SEQUENCE DESCRIPTION: SEQ ID NO: 2:

```
Met Asn Leu Leu Gln Lys Asn Lys Ile Asn Leu Arg Pro Phe Thr Lys
  1               5                  10                  15

Trp Thr Gly Gly Lys Arg Gln Leu Leu Pro His Ile Gln Tyr Leu Met
             20                  25                  30

Pro Glu Lys Tyr Asn His Phe Phe Glu Pro Phe Ile Gly Gly Gly Ala
         35                  40                  45

Leu Phe Phe Glu Leu Ala Pro Gln Lys Ala Val Ile Asn Asp Phe Asn
 50                  55                  60

Ser Glu Leu Ile Asn Cys Tyr Arg Gln Met Lys Asp Asn Pro Glu Gln
 65                  70                  75                  80

Leu Ile Glu Leu Leu Thr Asn His Gln Arg Glu Asn Ser Lys Glu Tyr
                 85                  90                  95

Tyr Leu Asp Leu Arg Ser Ser Arg Asp Gly Arg Ile Asp Lys Met
                100                 105                 110

Ser Glu Val Glu Arg Ala Ala Arg Ile Met Tyr Met Leu Arg Val Asp
                115                 120                 125

Phe Asn Gly Leu Tyr Arg Val Asn Ser Lys Asn Gln Phe Asn Val Pro
    130                 135                 140

Tyr Gly Arg Tyr Lys Asn Pro Lys Ile Val Asp Lys Glu Leu Ile Glu
145                 150                 155                 160

Ser Ile Ser Glu Tyr Leu Asn Asn Ser Ile Lys Ile Met Ser Gly
                165                 170                 175

Asp Phe Glu Lys Ala Val Lys Glu Ala Gln Asp Gly Asp Phe Val Tyr
                180                 185                 190

Phe Asp Pro Pro Tyr Ile Pro Leu Ser Glu Thr Ser Ala Phe Thr Ser
    195                 200                 205

Tyr Thr His Glu Gly Phe Ser Tyr Glu Asp Gln Val Arg Leu Arg Asp
210                 215                 220

Cys Phe Lys Gln Leu Asp Ser Lys Gly Val Phe Val Met Leu Ser Asn
225                 230                 235                 240

Ser Ser Ser Pro Leu Ala Glu Glu Leu Tyr Lys Asp Phe Tyr Ile His
                245                 250                 255

Lys Ile Glu Ala Thr Arg Thr Asn Gly Ala Lys Ser Ser Ser Arg Gly
                260                 265                 270

Lys Ile Thr Glu Ile Ile Val Thr Asn Tyr Gly Asn
                275                 280
```

(2) INFORMATION FOR SEQ ID NO: 3:

(i) SEQUENCE CHARACTERISTICS:
        (A) LENGTH: 3695 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Lactococcus lactis subsp. cremoris
    (B) STRAIN: W9

(ix) FEATURE:
    (A) NAME/KEY: CDS
    (B) LOCATION:1613..2419
    (C) IDENTIFICATION METHOD: experimental
    (D) OTHER INFORMATION:/codon_start= 1613
        /product= "LlaAI -GATC- adenine methylase B"
        /evidence= EXPERIMENTAL
        /gene= "ORF"
        /number= 2
        /standard_name= "Gene coding for M.LlaAIB"
        /label= m-llaAIB (xi) SEQUENCE DESCRIPTION: SEQ ID NO: 3:

```
ATATAAGATA TATAAATCAG TTCGCCTTTT TCTACTCCGT TCTAAAATCT TAAAATCAAG      60

GTCAAAAGAA AAAGTCAAAA CCATTGAATT GAGGTTCTAA AATTAAACTC CCTGCGTTGC     120

TCTTGGCTGC CGCTTGTACA CTCTGATTTT ATATTAGATA CATTCTGCCA TTAAAAAGAA     180

CTCCTAACGG TCGTGGCTAC TTTGTTTAGT CTAAACGCTT TAAATAGTCC TACAAGCTCA     240

TATTTTGCCT TTTAAGCGAT TTTAAACGTG AGTTAGTAAT AATTATCATG GATAAAAGAA     300

AAAGCCCTTA ATAGGCTTG TATGTAATTG ACTAAAACGT ACAATTTAGC TTTTAAATAT      360

GACCCTTATT TATGACCTGC TCTAACCTCA CTATTCATCA GCATTCAAAA AAGAGGTCAA     420

AACTGTTAAG TTATGAGCTG AATAGATTTT ATTAAATTTT ATTTGGTTTA AAAGACCAAT     480

TATCTATTTT TTAACAAACA CTAAAATAGA TTTTTTGGAA AACTTTGCAA CAGAACCAGC     540

AATCTGATGT TGCAGATGG ACGTTCTTTC GGTTTTGAAC CTCAAGGGGA ACACTCGTTT       600

GATAAAGCGT CTCAATGGTT GTCAGTAAAC AAACAAAAAC TTTTGGAAGT GTGCTATTAT     660

AAGTCATATA AGTCGTGCGC TTTCTAATGC TTAGTGCTTT AAGATTAGGA TAGCACGACT     720

TATTTATTTT CCAATAAAAT TAACTAGCAA TTCGGGTATA ATATATTTAT GAATTTATTA     780

CAAAAAAACA AGATCAACTT ACGTCCGTTT ACTAAATGGA CAGGTGGGAA AAGGCAACTA     840

CTGCCACACA TTCAATACCT AATGCCAGAA AAATACAATC ATTTTTTCGA ACCTTTTATT     900

GGTGGTGGCG CTTTGTTTTT TGAACTCGCT CCTCAAAAAG CAGTTATTAA CGACTTCAAT     960

TCTGAGCTTA TAAACTGTTA CCGGCAGATG AAAGATAATC CTGAGCAATT GATAGAATTG    1020

TTGACTAATC ATCAGCGGGA AAATTCTAAA GAATATTATT TAGACTTACG TTCTTCTGAT    1080

AGAGATGGAA GAATTGATAA GATGAGCGAA GTTGAACGTG CTGCTAGAAT TATGTATATG    1140

CTACGTGTTG ATTTTAATGG TTTATATCGT GTTAATTCGA AAAACCAGTT TAATGTGCCT    1200

TATGGAAGAT ATAAAAATCC TAAGATAGTT GATAAAGAAT TGATTGAAAG TATTTCCGAG    1260

TACTTGAATA ACAATTCTAT TAAGATCATG AGTGGAGATT TTGAAAAAGC CGTTAAAGAA    1320

GCACAGGATG GAGATTTTGT TTATTTCGAC CCTCCATACA TTCCACTTTC TGAAACTAGC    1380

GCCTTTACTT CTTATACACA CGAAGGCTTT AGCTACGAAG ATCAAGTTAG CTAAGAGAT    1440

TGTTTCAAAC AGTTAGATTC AAAAGGGGTA TTCGTCATGC TTTCAAATTC TTCAAGCCCT    1500

TTAGCGGAGG AATTATATAA AGATTTTTAC ATCCATAAAA TTGAAGCTAC TCGAACAAAT    1560

GGGGCTAAAT CATCTAGTCG TGGAAAAATC ACTGAAATCA TCGTAACCAA TT ATG        1615
                                                              Met
                                                              285

GCA ATT AAC GAA TAT AAG TAT GGA GGT GTT TTA ATG ATA AAA CCA TAC       1663
Ala Ile Asn Glu Tyr Lys Tyr Gly Gly Val Leu Met Ile Lys Pro Tyr
         290                 295                 300

TAT GAA AAA GAA AAC GCA ATT CTC GTT CAC GCA GAT TCA TTT AAA TTA       1711
```

```
Tyr Glu Lys Glu Asn Ala Ile Leu Val His Ala Asp Ser Phe Lys Leu
        305                 310                 315

TTA GAA AAA ATT AAA CCT GAA AGC ATG GAC ATG ATA TTT GCT GAC CCT      1759
Leu Glu Lys Ile Lys Pro Glu Ser Met Asp Met Ile Phe Ala Asp Pro
        320                 325                 330

CCT TAC TTT TTA AGT AAT GGA GGA ATG TCA AAT TCA GGT GGT CAA ATT      1807
Pro Tyr Phe Leu Ser Asn Gly Gly Met Ser Asn Ser Gly Gly Gln Ile
        335                 340                 345

GTT TCT GTT GAT AAA GGG GAT TGG GAT AAA ATT TCT TCA TTT GAA GAA      1855
Val Ser Val Asp Lys Gly Asp Trp Asp Lys Ile Ser Ser Phe Glu Glu
350                 355                 360                 365

AAA CAT GAC TTT AAT AGA CGT TGG ATT AGG TTA GCA AGA TTG GTT TTA      1903
Lys His Asp Phe Asn Arg Arg Trp Ile Arg Leu Ala Arg Leu Val Leu
                370                 375                 380

AAA CCC AAC GGA ACT ATT TGG GTT TCC GGA AGC CTT CAT AAC ATA TAT      1951
Lys Pro Asn Gly Thr Ile Trp Val Ser Gly Ser Leu His Asn Ile Tyr
            385                 390                 395

TCT GTC GGG ATG GCG CTG GAA CAG GAA GGT TTC AAA ATC TTA AAT AAT      1999
Ser Val Gly Met Ala Leu Glu Gln Glu Gly Phe Lys Ile Leu Asn Asn
            400                 405                 410

ATA ACT TGG CAA AAG ACA AAT CCT GCA CCT AAT CTA TCA TGT CGG TAC      2047
Ile Thr Trp Gln Lys Thr Asn Pro Ala Pro Asn Leu Ser Cys Arg Tyr
        415                 420                 425

TTC ACC CAC TCT ACA GAG ACA ATT TTA TGG GCA AGA AAG AAC GAT AAA      2095
Phe Thr His Ser Thr Glu Thr Ile Leu Trp Ala Arg Lys Asn Asp Lys
430                 435                 440                 445

AAA TCT CGC CAT TAT TAT AAC TAT GAA TTG ATG AAA GAG TTT AAT GAC      2143
Lys Ser Arg His Tyr Tyr Asn Tyr Glu Leu Met Lys Glu Phe Asn Asp
                450                 455                 460

GGG AAA CAA ATG AAA GAT GTT TGG ACA GGT AGT CTG ACA AAA AAA TCA      2191
Gly Lys Gln Met Lys Asp Val Trp Thr Gly Ser Leu Thr Lys Lys Ser
            465                 470                 475

GAA AAA TGG GCT GGG AAA CAT CCA ACT CAG AAG CCA GAG TAT ATT TTA      2239
Glu Lys Trp Ala Gly Lys His Pro Thr Gln Lys Pro Glu Tyr Ile Leu
            480                 485                 490

GAA CGG ATA ATC TTA GCT AGT ACA AAG GAA AAT GAT TAT ATT TTA GAC      2287
Glu Arg Ile Ile Leu Ala Ser Thr Lys Glu Asn Asp Tyr Ile Leu Asp
        495                 500                 505

CCT TTC GTC GGA AGT GGA ACT ACT GGT GTA GTA GCC AAG AGA TTG GGG      2335
Pro Phe Val Gly Ser Gly Thr Thr Gly Val Val Ala Lys Arg Leu Gly
510                 515                 520                 525

CGT AAA TTT ATT GGG ATT GAT TCT GAG AAA GAA TAT CTT AAA ATT GCT      2383
Arg Lys Phe Ile Gly Ile Asp Ser Glu Lys Glu Tyr Leu Lys Ile Ala
                530                 535                 540

AAA AAA AGG CTA AAT AAA GGA GCA ACA TAT GGA CTT TAATAATTAC           2429
Lys Lys Arg Leu Asn Lys Gly Ala Thr Tyr Gly Leu
            545                 550

ATCGGTTTAG AATCTGACGA TAGATTAAAT GCTTTTATGG CAACACTTTC CGTAACTAAT    2489

AGAACTCCCG AATACTACGT GAACTGGGAA AAAGTTGAAC GTGAAACACG AAAATTTGAA    2549

TTAGAACTAA ATACTTTAAA CTATCTCATT GGGAAAGAAG ATATTTATAG TGAAGCACTT    2609

GAACTATTTA CCAATCAACC TGAATTGCTT AAAGCTATTC CTAGTTTGAT TGCTAGTAGA    2669

GATACATCTT TAGATATACT AAACATTGAC GAAAATGATG ATATGAGTTT TGAACAACTT    2729

AACTTTCTTG TTATCGACGA AAATTGTATC GCTGATTATG TAGACTTTAT TAACCAGGCA    2789

GGTTTACTAG ATTTTCTACA GAATAAAGCA AAACGTTCTC TGGTAGACTA TGTGTATGGT    2849

GTTGAAGCAG GCTTGATAG CAATGCTCGA AAAAACCGAA GCGGTACAAC CATGGAGGGG     2909
```

```
ATTTTAGAAC GTACTGTTTC AAAAATAGCT CAAGAGAAAG GGCTTGAATG GAAGCCACAG      2969

GCAACCGCTT CTTTTATCAA GTCTCAATGG GACATAGAAG TCCCTGTAGA CAAATCAAAA      3029

AGACGCTTTG ATGCAGCAGT TTACTCTCGT GCGCTCAATA AGGTTTGGCT CATAGAAACA      3089

AATTACTACG GCGGTGGAGG AAGTAAACTC AAAGCAGTTG CTGGAGAATT TACAGAATTG      3149

AGTCAGTTTG TAAAAACATC AAAAGATAAT GTTGAATTTG TATGGGTAAC AGACGGCCAA      3209

GGGTGGAAAT TTTCCCGCTT ACCACTTGCA GAAGCTTTCG GACACATCGA TAACGTTTTC      3269

AATCTAACCA TGTTGAAAGA AGGTTTCTTG TCTGATTTAT TCGAAAAAGA ATTTAAAAA       3329

GACAGAGAAT CTCTGTCTTT TTAAATTTCA ATTCCTTCCT TCTGCTAGCT ATAACTTTCC      3389

AAAAAACCTG AAAACGGTT CTGTTGCAAT TGTATGTGGG GTCGGAACTT ACTACTATAT       3449

CATGAGAAAT GAAGATTAAA GTTGAAACAA AAAAACAGAT TATTTTAAAA TGTAAATCTG      3509

TTTTGTTTG GGCTGATTTT ATCACACCAA TTCTATGTTC AGAAAATGGT CATTTTCTGG       3569

ACACTCTTCT TTTGTTATTA AAACTCTCAA AATCATTTAC ATTTATTGTT CATTAACCCA      3629

TAATTTATTC TATGTTCATT TATAGATATC GAATTCCTGC AGGGCCCTCC ACTAGTTCTA      3689

GAGGCG                                                                 3695
```

(2) INFORMATION FOR SEQ ID NO: 4:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Ile Asn Glu Tyr Lys Tyr Gly Gly Val Leu Met Ile Lys Pro
 1               5                  10                  15

Tyr Tyr Glu Lys Glu Asn Ala Ile Leu Val His Ala Asp Ser Phe Lys
                20                  25                  30

Leu Leu Glu Lys Ile Lys Pro Glu Ser Met Asp Met Ile Phe Ala Asp
            35                  40                  45

Pro Pro Tyr Phe Leu Ser Asn Gly Gly Met Ser Asn Ser Gly Gly Gln
        50                  55                  60

Ile Val Ser Val Asp Lys Gly Asp Trp Asp Lys Ile Ser Ser Phe Glu
65                  70                  75                  80

Glu Lys His Asp Phe Asn Arg Arg Trp Ile Arg Leu Ala Arg Leu Val
                85                  90                  95

Leu Lys Pro Asn Gly Thr Ile Trp Val Ser Gly Ser Leu His Asn Ile
            100                 105                 110

Tyr Ser Val Gly Met Ala Leu Glu Gln Glu Gly Phe Lys Ile Leu Asn
        115                 120                 125

Asn Ile Thr Trp Gln Lys Thr Asn Pro Ala Pro Asn Leu Ser Cys Arg
    130                 135                 140

Tyr Phe Thr His Ser Thr Glu Thr Ile Leu Trp Ala Arg Lys Asn Asp
145                 150                 155                 160

Lys Lys Ser Arg His Tyr Tyr Asn Tyr Glu Leu Met Lys Glu Phe Asn
                165                 170                 175

Asp Gly Lys Gln Met Lys Asp Val Trp Thr Gly Ser Leu Thr Lys Lys
            180                 185                 190

Ser Glu Lys Trp Ala Gly Lys His Pro Thr Gln Lys Pro Glu Tyr Ile
        195                 200                 205
```

```
Leu Glu Arg Ile Ile Leu Ala Ser Thr Lys Glu Asn Asp Tyr Ile Leu
    210                 215                 220

Asp Pro Phe Val Gly Ser Gly Thr Thr Gly Val Val Ala Lys Arg Leu
225                 230                 235                 240

Gly Arg Lys Phe Ile Gly Ile Asp Ser Glu Lys Glu Tyr Leu Lys Ile
                245                 250                 255

Ala Lys Lys Arg Leu Asn Lys Gly Ala Thr Tyr Gly Leu
            260                 265
```

(2) INFORMATION FOR SEQ ID NO: 5:

(i) SEQUENCE CHARACTERISTICS:
        (A) LENGTH: 3695 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Lactococcus lactis subsp. cremoris
        (B) STRAIN: W9

(ix) FEATURE:
        (A) NAME/KEY: CDS
        (B) LOCATION:1649..2419
        (C) IDENTIFICATION METHOD: experimental
        (D) OTHER INFORMATION:/codon_start= 1649
            /product= "LlaAI -GATC-adenine methylase B"
            /evidence= EXPERIMENTAL
            /gene= "ORF"
            /number= 2
            /standard_name= "Gene coding for M.LlaAIB"
            /label= m-llaAIB (xi) SEQUENCE DESCRIPTION: SEQ ID NO: 5:

```
ATATAAGATA TATAAATCAG TTCGCCTTTT TCTACTCCGT TCTAAAATCT TAAAATCAAG      60

GTCAAAAGAA AAAGTCAAAA CCATTGAATT GAGGTTCTAA AATTAAACTC CCTGCGTTGC     120

TCTTGGCTGC CGCTTGTACA CTCTGATTTT ATATTAGATA CATTCTGCCA TTAAAAAGAA     180

CTCCTAACGG TCGTGGCTAC TTTGTTTAGT CTAAACGCTT TAAATAGTCC TACAAGCTCA     240

TATTTTGCCT TTTAAGCGAT TTTAAACGTG AGTTAGTAAT AATTATCATG GATAAAAGAA     300

AAAGCCCTTA AATAGGCTTG TATGTAATTG ACTAAAACGT ACAATTTAGC TTTTAAATAT     360

GACCCTTATT TATGACCTGC TCTAACCTCA CTATTCATCA GCATTCAAAA AAGAGGTCAA     420

AACTGTTAAG TTATGAGCTG AATAGATTTT ATTAAATTTT ATTTGGTTTA AAAGACCAAT     480

TATCTATTTT TTAACAAACA CTAAAATAGA TTTTTTGGAA AACTTTGCAA CAGAACCAGC     540

AATCTGATGT TGCGAGATGG ACGTTCTTTC GGTTTTGAAC CTCAAGGGGA ACACTCGTTT     600

GATAAAGCGT CTCAATGGTT GTCAGTAAAC AAACAAAAAC TTTTGGAAGT GTGCTATTAT     660

AAGTCATATA AGTCGTGCGC TTTCTAATGC TTAGTGCTTT AAGATTAGGA TAGCACGACT     720

TATTTATTTT CCAATAAAAT TAACTAGCAA TTCGGGTATA ATATATTTAT GAATTTATTA     780

CAAAAAAACA AGATCAACTT ACGTCCGTTT ACTAAATGGA CAGGTGGGAA AAGGCAACTA     840

CTGCCACACA TTCAATACCT AATGCCAGAA AAATACAATC ATTTTTTCGA ACCTTTTATT     900

GGTGGTGGCG CTTTGTTTTT TGAACTCGCT CCTCAAAAAG CAGTTATTAA CGACTTCAAT     960

TCTGAGCTTA TAAACTGTTA CCGGCAGATG AAAGATAATC CTGAGCAATT GATAGAATTG    1020
```

```
TTGACTAATC ATCAGCGGGA AAATTCTAAA GAATATTATT TAGACTTACG TTCTTCTGAT      1080

AGAGATGGAA GAATTGATAA GATGAGCGAA GTTGAACGTG CTGCTAGAAT TATGTATATG      1140

CTACGTGTTG ATTTTAATGG TTTATATCGT GTTAATTCGA AAAACCAGTT TAATGTGCCT      1200

TATGGAAGAT ATAAAAATCC TAAGATAGTT GATAAAGAAT TGATTGAAAG TATTTCCGAG      1260

TACTTGAATA ACAATTCTAT TAAGATCATG AGTGGAGATT TGAAAAAGC CGTTAAAGAA       1320

GCACAGGATG GAGATTTTGT TTATTTCGAC CCTCCATACA TTCCACTTTC TGAAACTAGC      1380

GCCTTTACTT CTTATACACA CGAAGGCTTT AGCTACGAAG ATCAAGTTAG CTAAGAGAT       1440

TGTTTCAAAC AGTTAGATTC AAAAGGGGTA TTCGTCATGC TTTCAAATTC TTCAAGCCCT     1500

TTAGCGGAGG AATTATATAA AGATTTTTAC ATCCATAAAA TTGAAGCTAC TCGAACAAAT     1560

GGGGCTAAAT CATCTAGTCG TGGAAAAATC ACTGAAATCA TCGTAACCAA TTATGGCAAT    1620

TAACGAATAT AAGTATGGAG GTGTTTTA ATG ATA AAA CCA TAC TAT GAA AAA       1672
                              Met Ile Lys Pro Tyr Tyr Glu Lys
                                  270                 275

GAA AAC GCA ATT CTC GTT CAC GCA GAT TCA TTT AAA TTA TTA GAA AAA      1720
Glu Asn Ala Ile Leu Val His Ala Asp Ser Phe Lys Leu Leu Glu Lys
        280                 285                 290

ATT AAA CCT GAA AGC ATG GAC ATG ATA TTT GCT GAC CCT CCT TAC TTT      1768
Ile Lys Pro Glu Ser Met Asp Met Ile Phe Ala Asp Pro Pro Tyr Phe
295                 300                 305

TTA AGT AAT GGA GGA ATG TCA AAT TCA GGT GGT CAA ATT GTT TCT GTT      1816
Leu Ser Asn Gly Gly Met Ser Asn Ser Gly Gly Gln Ile Val Ser Val
310                 315                 320                 325

GAT AAA GGG GAT TGG GAT AAA ATT TCT TCA TTT GAA GAA AAA CAT GAC      1864
Asp Lys Gly Asp Trp Asp Lys Ile Ser Ser Phe Glu Glu Lys His Asp
                330                 335                 340

TTT AAT AGA CGT TGG ATT AGG TTA GCA AGA TTG GTT TTA AAA CCC AAC      1912
Phe Asn Arg Arg Trp Ile Arg Leu Ala Arg Leu Val Leu Lys Pro Asn
            345                 350                 355

GGA ACT ATT TGG GTT TCC GGA AGC CTT CAT AAC ATA TAT TCT GTC GGG      1960
Gly Thr Ile Trp Val Ser Gly Ser Leu His Asn Ile Tyr Ser Val Gly
        360                 365                 370

ATG GCG CTG GAA CAG GAA GGT TTC AAA ATC TTA AAT AAT ATA ACT TGG      2008
Met Ala Leu Glu Gln Glu Gly Phe Lys Ile Leu Asn Asn Ile Thr Trp
375                 380                 385

CAA AAG ACA AAT CCT GCA CCT AAT CTA TCA TGT CGG TAC TTC ACC CAC      2056
Gln Lys Thr Asn Pro Ala Pro Asn Leu Ser Cys Arg Tyr Phe Thr His
390                 395                 400                 405

TCT ACA GAG ACA ATT TTA TGG GCA AGA AAG AAC GAT AAA AAA TCT CGC      2104
Ser Thr Glu Thr Ile Leu Trp Ala Arg Lys Asn Asp Lys Lys Ser Arg
                410                 415                 420

CAT TAT TAT AAC TAT GAA TTG ATG AAA GAG TTT AAT GAC GGG AAA CAA      2152
His Tyr Tyr Asn Tyr Glu Leu Met Lys Glu Phe Asn Asp Gly Lys Gln
            425                 430                 435

ATG AAA GAT GTT TGG ACA GGT AGT CTG ACA AAA AAA TCA GAA AAA TGG      2200
Met Lys Asp Val Trp Thr Gly Ser Leu Thr Lys Lys Ser Glu Lys Trp
        440                 445                 450

GCT GGG AAA CAT CCA ACT CAG AAG CCA GAG TAT ATT TTA GAA CGG ATA      2248
Ala Gly Lys His Pro Thr Gln Lys Pro Glu Tyr Ile Leu Glu Arg Ile
455                 460                 465

ATC TTA GCT AGT ACA AAG GAA AAT GAT TAT ATT TTA GAC CCT TTC GTC      2296
Ile Leu Ala Ser Thr Lys Glu Asn Asp Tyr Ile Leu Asp Pro Phe Val
470                 475                 480                 485

GGA AGT GGA ACT ACT GGT GTA GTA GCC AAG AGA TTG GGG CGT AAA TTT      2344
Gly Ser Gly Thr Thr Gly Val Val Ala Lys Arg Leu Gly Arg Lys Phe
                490                 495                 500
```

```
ATT GGG ATT GAT TCT GAG AAA GAA TAT CTT AAA ATT GCT AAA AAA AGG      2392
Ile Gly Ile Asp Ser Glu Lys Glu Tyr Leu Lys Ile Ala Lys Lys Arg
            505                 510                 515

CTA AAT AAA GGA GCA ACA TAT GGA CTT TAATAATTAC ATCGGTTTAG            2439
Leu Asn Lys Gly Ala Thr Tyr Gly Leu
        520                 525

AATCTGACGA TAGATTAAAT GCTTTTATGG CAACACTTTC CGTAACTAAT AGAACTCCCG    2499

AATACTACGT GAACTGGGAA AAAGTTGAAC GTGAAACACG AAAATTTGAA TTAGAACTAA    2559

ATACTTTAAA CTATCTCATT GGGAAAGAAG ATATTTATAG TGAAGCACTT GAACTATTTA    2619

CCAATCAACC TGAATTGCTT AAAGCTATTC CTAGTTTGAT TGCTAGTAGA GATACATCTT    2679

TAGATATACT AAACATTGAC GAAAATGATG ATATGAGTTT TGAACAACTT AACTTTCTTG    2739

TTATCGACGA AAATTGTATC GCTGATTATG TAGACTTTAT TAACCAGGCA GGTTTACTAG    2799

ATTTTCTACA GAATAAAGCA AAACGTTCTC TGGTAGACTA TGTGTATGGT GTTGAAGCAG    2859

GGCTTGATAG CAATGCTCGA AAAAACCGAA GCGGTACAAC CATGGAGGGG ATTTTAGAAC    2919

GTACTGTTTC AAAAATAGCT CAAGAGAAAG GGCTTGAATG GAAGCCACAG GCAACCGCTT    2979

CTTTTATCAA GTCTCAATGG GACATAGAAG TCCCTGTAGA CAAATCAAAA AGACGCTTTG    3039

ATGCAGCAGT TTACTCTCGT GCGCTCAATA AGGTTTGGCT CATAGAAACA AATTACTACG    3099

GCGGTGGAGG AAGTAAACTC AAAGCAGTTG CTGGAGAATT TACAGAATTG AGTCAGTTTG    3159

TAAAAACATC AAAAGATAAT GTTGAATTTG TATGGGTAAC AGACGGCCAA GGGTGGAAAT    3219

TTTCCCGCTT ACCACTTGCA GAAGCTTTCG GACACATCGA TAACGTTTTC AATCTAACCA    3279

TGTTGAAAGA AGGTTTCTTG TCTGATTTAT TCGAAAAAGA AATTTAAAAA GACAGAGAAT    3339

CTCTGTCTTT TTAAATTTCA ATTCCTTCCT TCTGCTAGCT ATAACTTTCC AAAAAACCTG    3399

AAAAACGGTT CTGTTGCAAT TGTATGTGGG GTCGGAACTT ACTACTATAT CATGAGAAAT    3459

GAAGATTAAA GTTGAAACAA AAAAACAGAT TATTTTAAAA TGTAAATCTG TTTTTGTTTG    3519

GGCTGATTTT ATCACACCAA TTCTATGTTC AGAAAATGGT CATTTTCTGG ACACTCTTCT    3579

TTTGTTATTA AAACTCTCAA AATCATTTAC ATTTATTGTT CATTAACCCA TAATTTATTC    3639

TATGTTCATT TATAGATATC GAATTCCTGC AGGGCCCTCC ACTAGTTCTA GAGGCG       3695

(2) INFORMATION FOR SEQ ID NO: 6:

(i) SEQUENCE CHARACTERISTICS:
        (A) LENGTH: 257 amino acids
        (B) TYPE: amino acid
        (D) TOPOLOGY: linear (ii) MOLECULE TYPE: protein (xi) SEQUENCE DESCRIPTION: SEQ ID NO: 6:

Met Ile Lys Pro Tyr Tyr Glu Lys Glu Asn Ala Ile Leu Val His Ala
  1               5                  10                  15

Asp Ser Phe Lys Leu Leu Glu Lys Ile Lys Pro Glu Ser Met Asp Met
             20                  25                  30

Ile Phe Ala Asp Pro Pro Tyr Phe Leu Ser Asn Gly Gly Met Ser Asn
         35                  40                  45

Ser Gly Gly Gln Ile Val Ser Val Asp Lys Gly Asp Trp Asp Lys Ile
     50                  55                  60

Ser Ser Phe Glu Glu Lys His Asp Phe Asn Arg Arg Trp Ile Arg Leu
 65                  70                  75                  80

Ala Arg Leu Val Leu Lys Pro Asn Gly Thr Ile Trp Val Ser Gly Ser
```

```
                    85                  90                  95
Leu His Asn Ile Tyr Ser Val Gly Met Ala Leu Glu Gln Glu Gly Phe
                100                 105                 110

Lys Ile Leu Asn Asn Ile Thr Trp Gln Lys Thr Asn Pro Ala Pro Asn
            115                 120                 125

Leu Ser Cys Arg Tyr Phe Thr His Ser Thr Glu Thr Ile Leu Trp Ala
        130                 135                 140

Arg Lys Asn Asp Lys Lys Ser Arg His Tyr Tyr Asn Tyr Glu Leu Met
145                 150                 155                 160

Lys Glu Phe Asn Asp Gly Lys Gln Met Lys Asp Val Trp Thr Gly Ser
                165                 170                 175

Leu Thr Lys Lys Ser Glu Lys Trp Ala Gly Lys His Pro Thr Gln Lys
            180                 185                 190

Pro Glu Tyr Ile Leu Glu Arg Ile Ile Leu Ala Ser Thr Lys Glu Asn
        195                 200                 205

Asp Tyr Ile Leu Asp Pro Phe Val Gly Ser Gly Thr Thr Gly Val Val
    210                 215                 220

Ala Lys Arg Leu Gly Arg Lys Phe Ile Gly Ile Asp Ser Glu Lys Glu
225                 230                 235                 240

Tyr Leu Lys Ile Ala Lys Lys Arg Leu Asn Lys Gly Ala Thr Tyr Gly
                245                 250                 255

Leu
```

(2) INFORMATION FOR SEQ ID NO: 7:

(i) SEQUENCE CHARACTERISTICS:
  (A) LENGTH: 3695 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Lactococcus lactis subsp. cremoris
  (B) STRAIN: W9

(ix) FEATURE:
  (A) NAME/KEY: CDS
  (B) LOCATION:2412..3323
  (C) IDENTIFICATION METHOD: experimental
  (D) OTHER INFORMATION:/codon_start= 2412
   /product= "LlaAI restriction endonuclease"
   /evidence= EXPERIMENTAL
   /gene= "ORF"
   /number= 3
   /standard_name= "Gene coding for LlaAI restriction
   endonuclease"
   /label= r-llaAI (xi) SEQUENCE DESCRIPTION: SEQ ID NO: 7:

```
ATATAAGATA TATAAATCAG TTCGCCTTTT TCTACTCCGT TCTAAAATCT TAAAATCAAG      60

GTCAAAAGAA AAAGTCAAAA CCATTGAATT GAGGTTCTAA AATTAAACTC CCTGCGTTGC     120

TCTTGGCTGC CGCTTGTACA CTCTGATTTT ATATTAGATA CATTCTGCCA TTAAAAAGAA     180

CTCCTAACGG TCGTGGCTAC TTTGTTTAGT CTAAACGCTT TAAATAGTCC TACAAGCTCA     240

TATTTTGCCT TTTAAGCGAT TTTAAACGTG AGTTAGTAAT AATTATCATG GATAAAAGAA     300

AAAGCCCTTA AATAGGCTTG TATGTAATTG ACTAAAACGT ACAATTTAGC TTTTAAATAT     360
```

```
GACCCTTATT TATGACCTGC TCTAACCTCA CTATTCATCA GCATTCAAAA AAGAGGTCAA      420

AACTGTTAAG TTATGAGCTG AATAGATTTT ATTAAATTTT ATTTGGTTTA AAAGACCAAT      480

TATCTATTTT TTAACAAACA CTAAAATAGA TTTTTTGGAA AACTTTGCAA CAGAACCAGC      540

AATCTGATGT TGCGAGATGG ACGTTCTTTC GGTTTTGAAC CTCAAGGGGA ACACTCGTTT      600

GATAAAGCGT CTCAATGGTT GTCAGTAAAC AAACAAAAAC TTTTGGAAGT GTGCTATTAT      660

AAGTCATATA AGTCGTGCGC TTTCTAATGC TTAGTGCTTT AAGATTAGGA TAGCACGACT      720

TATTTATTTT CCAATAAAAT TAACTAGCAA TTCGGGTATA ATATATTTAT GAATTTATTA      780

CAAAAAAACA AGATCAACTT ACGTCCGTTT ACTAAATGGA CAGGTGGGAA AAGGCAACTA      840

CTGCCACACA TTCAATACCT AATGCCAGAA AAATACAATC ATTTTTTCGA ACCTTTTATT      900

GGTGGTGGCG CTTTGTTTTT TGAACTCGCT CCTCAAAAAG CAGTTATTAA CGACTTCAAT      960

TCTGAGCTTA TAAACTGTTA CCGGCAGATG AAAGATAATC TGAGCAATT GATAGAATTG     1020

TTGACTAATC ATCAGCGGGA AAATTCTAAA GAATATTATT TAGACTTACG TTCTTCTGAT     1080

AGAGATGGAA GAATTGATAA GATGAGCGAA GTTGAACGTG CTGCTAGAAT TATGTATATG     1140

CTACGTGTTG ATTTTAATGG TTTATATCGT GTTAATTCGA AAAACCAGTT TAATGTGCCT     1200

TATGAAGAT ATAAAAATCC TAAGATAGTT GATAAAGAAT TGATTGAAAG TATTTCCGAG     1260

TACTTGAATA ACAATTCTAT TAAGATCATG AGTGGAGATT TTGAAAAAGC CGTTAAAGAA     1320

GCACAGGATG GAGATTTTGT TTATTTCGAC CCTCCATACA TTCCACTTTC TGAAACTAGC     1380

GCCTTTACTT CTTATACACA CGAAGGCTTT AGCTACGAAG ATCAAGTTAG CTAAGAGAT     1440

TGTTTCAAAC AGTTAGATTC AAAAGGGGTA TTCGTCATGC TTTCAAATTC TTCAAGCCCT     1500

TTAGCGGAGG AATTATATAA AGATTTTTAC ATCCATAAAA TTGAAGCTAC TCGAACAAAT     1560

GGGGCTAAAT CATCTAGTCG TGGAAAAATC ACTGAAATCA TCGTAACCAA TTATGGCAAT     1620

TAACGAATAT AAGTATGGAG GTGTTTTAAT GATAAAACCA TACTATGAAA AAGAAAACGC     1680

AATTCTCGTT CACGCAGATT CATTTAAATT ATTAGAAAAA ATTAAACCTG AAAGCATGGA     1740

CATGATATTT GCTGACCCTC CTTACTTTTT AAGTAATGGA GGAATGTCAA ATTCAGGTGG     1800

TCAAATTGTT TCTGTTGATA AAGGGGATTG GGATAAAATT TCTTCATTTG AAGAAAAACA     1860

TGACTTTAAT AGACGTTGGA TTAGGTTAGC AAGATTGGTT TTAAAACCCA ACGGAACTAT     1920

TTGGGTTTCC GGAAGCCTTC ATAACATATA TTCTGTCGGG ATGGCGCTGG AACAGGAAGG     1980

TTTCAAAATC TTAAATAATA TAACTTGGCA AAAGACAAAT CCTGCACCTA ATCTATCATG     2040

TCGGTACTTC ACCCACTCTA CAGAGACAAT TTTATGGGCA AGAAAGAACG ATAAAAAATC     2100

TCGCCATTAT TATAACTATG AATTGATGAA AGAGTTTAAT GACGGGAAAC AAATGAAAGA     2160

TGTTTGGACA GGTAGTCTGA CAAAAAAATC AGAAAAATGG GCTGGGAAAC ATCCAACTCA     2220

GAAGCCAGAG TATATTTTAG AACGGATAAT CTTAGCTAGT ACAAAGGAAA ATGATTATAT     2280

TTTAGACCCT TTCGTCGGAA GTGGAACTAC TGGTGTAGTA GCCAAGAGAT TGGGGCGTAA     2340

ATTTATTGGG ATTGATTCTG AGAAAGAATA TCTTAAAATT GCTAAAAAAA GGCTAAATAA     2400

AGGAGCAACA T ATG GAC TTT AAT AAT TAC ATC GGT TTA GAA TCT GAC GAT      2450
             Met Asp Phe Asn Asn Tyr Ile Gly Leu Glu Ser Asp Asp
                 260                 265                 270

AGA TTA AAT GCT TTT ATG GCA ACA CTT TCC GTA ACT AAT AGA ACT CCC      2498
Arg Leu Asn Ala Phe Met Ala Thr Leu Ser Val Thr Asn Arg Thr Pro
            275                 280                 285

GAA TAC TAC GTG AAC TGG GAA AAA GTT GAA CGT GAA ACA CGA AAA TTT      2546
Glu Tyr Tyr Val Asn Trp Glu Lys Val Glu Arg Glu Thr Arg Lys Phe
```

-continued

|  |  |  | 290 |  |  |  | 295 |  |  |  | 300 |  |  |  |  |
|---|---|---|---|---|---|---|---|---|---|---|---|---|---|---|---|
| GAA | TTA | GAA | CTA | AAT | ACT | TTA | AAC | TAT | CTC | ATT | GGG | AAA | GAA | GAT | ATT | 2594 |
| Glu | Leu | Glu | Leu | Asn | Thr | Leu | Asn | Tyr | Leu | Ile | Gly | Lys | Glu | Asp | Ile |
|  |  | 305 |  |  |  |  | 310 |  |  |  |  | 315 |  |  |  |

| TAT | AGT | GAA | GCA | CTT | GAA | CTA | TTT | ACC | AAT | CAA | CCT | GAA | TTG | CTT | AAA | 2642 |
|---|---|---|---|---|---|---|---|---|---|---|---|---|---|---|---|---|
| Tyr | Ser | Glu | Ala | Leu | Glu | Leu | Phe | Thr | Asn | Gln | Pro | Glu | Leu | Leu | Lys |
|  | 320 |  |  |  |  | 325 |  |  |  |  | 330 |  |  |  |  |

| GCT | ATT | CCT | AGT | TTG | ATT | GCT | AGT | AGA | GAT | ACA | TCT | TTA | GAT | ATA | CTA | 2690 |
|---|---|---|---|---|---|---|---|---|---|---|---|---|---|---|---|---|
| Ala | Ile | Pro | Ser | Leu | Ile | Ala | Ser | Arg | Asp | Thr | Ser | Leu | Asp | Ile | Leu |
| 335 |  |  |  |  | 340 |  |  |  |  | 345 |  |  |  |  | 350 |

| AAC | ATT | GAC | GAA | AAT | GAT | GAT | ATG | AGT | TTT | GAA | CAA | CTT | AAC | TTT | CTT | 2738 |
|---|---|---|---|---|---|---|---|---|---|---|---|---|---|---|---|---|
| Asn | Ile | Asp | Glu | Asn | Asp | Asp | Met | Ser | Phe | Glu | Gln | Leu | Asn | Phe | Leu |
|  |  |  |  | 355 |  |  |  |  | 360 |  |  |  |  | 365 |  |

| GTT | ATC | GAC | GAA | AAT | TGT | ATC | GCT | GAT | TAT | GTA | GAC | TTT | ATT | AAC | CAG | 2786 |
|---|---|---|---|---|---|---|---|---|---|---|---|---|---|---|---|---|
| Val | Ile | Asp | Glu | Asn | Cys | Ile | Ala | Asp | Tyr | Val | Asp | Phe | Ile | Asn | Gln |
|  |  |  | 370 |  |  |  |  | 375 |  |  |  |  | 380 |  |  |

| GCA | GGT | TTA | CTA | GAT | TTT | CTA | CAG | AAT | AAA | GCA | AAA | CGT | TCT | CTG | GTA | 2834 |
|---|---|---|---|---|---|---|---|---|---|---|---|---|---|---|---|---|
| Ala | Gly | Leu | Leu | Asp | Phe | Leu | Gln | Asn | Lys | Ala | Lys | Arg | Ser | Leu | Val |
|  |  | 385 |  |  |  |  | 390 |  |  |  |  | 395 |  |  |  |

| GAC | TAT | GTG | TAT | GGT | GTT | GAA | GCA | GGG | CTT | GAT | AGC | AAT | GCT | CGA | AAA | 2882 |
|---|---|---|---|---|---|---|---|---|---|---|---|---|---|---|---|---|
| Asp | Tyr | Val | Tyr | Gly | Val | Glu | Ala | Gly | Leu | Asp | Ser | Asn | Ala | Arg | Lys |
| 400 |  |  |  |  | 405 |  |  |  |  | 410 |  |  |  |  |  |

| AAC | CGA | AGC | GGT | ACA | ACC | ATG | GAG | GGG | ATT | TTA | GAA | CGT | ACT | GTT | TCA | 2930 |
|---|---|---|---|---|---|---|---|---|---|---|---|---|---|---|---|---|
| Asn | Arg | Ser | Gly | Thr | Thr | Met | Glu | Gly | Ile | Leu | Glu | Arg | Thr | Val | Ser |
| 415 |  |  |  |  | 420 |  |  |  |  | 425 |  |  |  |  | 430 |

| AAA | ATA | GCT | CAA | GAG | AAA | GGG | CTT | GAA | TGG | AAG | CCA | CAG | GCA | ACC | GCT | 2978 |
|---|---|---|---|---|---|---|---|---|---|---|---|---|---|---|---|---|
| Lys | Ile | Ala | Gln | Glu | Lys | Gly | Leu | Glu | Trp | Lys | Pro | Gln | Ala | Thr | Ala |
|  |  |  | 435 |  |  |  |  | 440 |  |  |  |  | 445 |  |  |

| TCT | TTT | ATC | AAG | TCT | CAA | TGG | GAC | ATA | GAA | GTC | CCT | GTA | GAC | AAA | TCA | 3026 |
|---|---|---|---|---|---|---|---|---|---|---|---|---|---|---|---|---|
| Ser | Phe | Ile | Lys | Ser | Gln | Trp | Asp | Ile | Glu | Val | Pro | Val | Asp | Lys | Ser |
|  |  | 450 |  |  |  |  | 455 |  |  |  |  | 460 |  |  |  |

| AAA | AGA | CGC | TTT | GAT | GCA | GCA | GTT | TAC | TCT | CGT | GCG | CTC | AAT | AAG | GTT | 3074 |
|---|---|---|---|---|---|---|---|---|---|---|---|---|---|---|---|---|
| Lys | Arg | Arg | Phe | Asp | Ala | Ala | Val | Tyr | Ser | Arg | Ala | Leu | Asn | Lys | Val |
|  |  | 465 |  |  |  |  | 470 |  |  |  |  | 475 |  |  |  |

| TGG | CTC | ATA | GAA | ACA | AAT | TAC | TAC | GGC | GGT | GGA | GGA | AGT | AAA | CTC | AAA | 3122 |
|---|---|---|---|---|---|---|---|---|---|---|---|---|---|---|---|---|
| Trp | Leu | Ile | Glu | Thr | Asn | Tyr | Tyr | Gly | Gly | Gly | Gly | Ser | Lys | Leu | Lys |
|  | 480 |  |  |  |  | 485 |  |  |  |  | 490 |  |  |  |  |

| GCA | GTT | GCT | GGA | GAA | TTT | ACA | GAA | TTG | AGT | CAG | TTT | GTA | AAA | ACA | TCA | 3170 |
|---|---|---|---|---|---|---|---|---|---|---|---|---|---|---|---|---|
| Ala | Val | Ala | Gly | Glu | Phe | Thr | Glu | Leu | Ser | Gln | Phe | Val | Lys | Thr | Ser |
| 495 |  |  |  |  | 500 |  |  |  |  | 505 |  |  |  |  | 510 |

| AAA | GAT | AAT | GTT | GAA | TTT | GTA | TGG | GTA | ACA | GAC | GGC | CAA | GGG | TGG | AAA | 3218 |
|---|---|---|---|---|---|---|---|---|---|---|---|---|---|---|---|---|
| Lys | Asp | Asn | Val | Glu | Phe | Val | Trp | Val | Thr | Asp | Gly | Gln | Gly | Trp | Lys |
|  |  |  | 515 |  |  |  |  | 520 |  |  |  |  | 525 |  |  |

| TTT | TCC | CGC | TTA | CCA | CTT | GCA | GAA | GCT | TTC | GGA | CAC | ATC | GAT | AAC | GTT | 3266 |
|---|---|---|---|---|---|---|---|---|---|---|---|---|---|---|---|---|
| Phe | Ser | Arg | Leu | Pro | Leu | Ala | Glu | Ala | Phe | Gly | His | Ile | Asp | Asn | Val |
|  |  | 530 |  |  |  |  | 535 |  |  |  |  | 540 |  |  |  |

| TTC | AAT | CTA | ACC | ATG | TTG | AAA | GAA | GGT | TTC | TTG | TCT | GAT | TTA | TTC | GAA | 3314 |
|---|---|---|---|---|---|---|---|---|---|---|---|---|---|---|---|---|
| Phe | Asn | Leu | Thr | Met | Leu | Lys | Glu | Gly | Phe | Leu | Ser | Asp | Leu | Phe | Glu |
|  |  | 545 |  |  |  |  | 550 |  |  |  |  | 555 |  |  |  |

| AAA | GAA | ATT | TAAAAGACA | GAGAATCTCT | GTCTTTTTAA | ATTTCAATTC | 3363 |
|---|---|---|---|---|---|---|---|
| Lys | Glu | Ile |
|  |  | 560 |

CTTCCTTCTG CTAGCTATAA CTTTCCAAAA AACCTGAAAA ACGGTTCTGT TGCAATTGTA 3423

TGTGGGGTCG GAACTTACTA CTATATCATG AGAAATGAAG ATTAAAGTTG AAACAAAAAA 3483

ACAGATTATT TTAAAATGTA AATCTGTTTT TGTTTGGGCT GATTTTATCA CACCAATTCT 3543

ATGTTCAGAA AATGGTCATT TTCTGGACAC TCTTCTTTTG TTATTAAAAC TCTCAAAATC 3603

ATTTACATTT ATTGTTCATT AACCCATAAT TTATTCTATG TTCATTTATA GATATCGAAT 3663

TCCTGCAGGG CCCTCCACTA GTTCTAGAGG CG                                    3695

(2) INFORMATION FOR SEQ ID NO: 8:

(i) SEQUENCE CHARACTERISTICS:
        (A) LENGTH: 304 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Asp Phe Asn Asn Tyr Ile Gly Leu Glu Ser Asp Asp Arg Leu Asn
  1               5                  10                  15

Ala Phe Met Ala Thr Leu Ser Val Thr Asn Arg Thr Pro Glu Tyr Tyr
             20                  25                  30

Val Asn Trp Glu Lys Val Glu Arg Glu Thr Arg Lys Phe Glu Leu Glu
         35                  40                  45

Leu Asn Thr Leu Asn Tyr Leu Ile Gly Lys Glu Asp Ile Tyr Ser Glu
     50                  55                  60

Ala Leu Glu Leu Phe Thr Asn Gln Pro Glu Leu Leu Lys Ala Ile Pro
 65                  70                  75                  80

Ser Leu Ile Ala Ser Arg Asp Thr Ser Leu Asp Ile Leu Asn Ile Asp
                 85                  90                  95

Glu Asn Asp Asp Met Ser Phe Glu Gln Leu Asn Phe Leu Val Ile Asp
            100                 105                 110

Glu Asn Cys Ile Ala Asp Tyr Val Asp Phe Ile Asn Gln Ala Gly Leu
        115                 120                 125

Leu Asp Phe Leu Gln Asn Lys Ala Lys Arg Ser Leu Val Asp Tyr Val
    130                 135                 140

Tyr Gly Val Glu Ala Gly Leu Asp Ser Asn Ala Arg Lys Asn Arg Ser
145                 150                 155                 160

Gly Thr Thr Met Glu Gly Ile Leu Glu Arg Thr Val Ser Lys Ile Ala
                165                 170                 175

Gln Glu Lys Gly Leu Glu Trp Lys Pro Gln Ala Thr Ala Ser Phe Ile
            180                 185                 190

Lys Ser Gln Trp Asp Ile Glu Val Pro Val Asp Lys Ser Lys Arg Arg
        195                 200                 205

Phe Asp Ala Ala Val Tyr Ser Arg Ala Leu Asn Lys Val Trp Leu Ile
    210                 215                 220

Glu Thr Asn Tyr Tyr Gly Gly Gly Ser Lys Leu Lys Ala Val Ala
225                 230                 235                 240

Gly Glu Phe Thr Glu Leu Ser Gln Phe Val Lys Thr Ser Lys Asp Asn
                245                 250                 255

Val Glu Pro Val Trp Val Thr Asp Gly Gln Gly Trp Lys Phe Ser Arg
            260                 265                 270

Leu Pro Leu Ala Glu Ala Phe Gly His Ile Asp Asn Val Phe Asn Leu
    275                 280                 285

Thr Met Leu Lys Glu Gly Phe Leu Ser Asp Leu Phe Glu Lys Glu Ile
290                 295                 300
```

(2) INFORMATION FOR SEQ ID NO: 9:

(i) SEQUENCE CHARACTERISTICS:
        (A) LENGTH: 3706 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Lactococcus lactis subsp. cremoris
         (B) STRAIN: W56

(ix) FEATURE:
         (A) NAME/KEY: CDS
         (B) LOCATION:complement (422..2161)
         (C) IDENTIFICATION METHOD: experimental
         (D) OTHER INFORMATION:/codon_start= 422
             /product= "LlaBI methylase"
             /evidence= EXPERIMENTAL
             /gene= "ORF"
             /number= 1
             /standard_name= "Gene coding for LlaBI methylase"
             /label= m-llaBI (ix) FEATURE:
         (A) NAME/KEY: CDS
         (B) LOCATION:2464..3360
         (C) IDENTIFICATION METHOD: experimental
         (D) OTHER INFORMATION:/codon_start= 2464
             /product= "LlaBI endonuclease"
             /evidence= EXPERIMENTAL
             /gene= "ORF"
             /number= 2
             /standard_name= "Gene coding for LlaBI endonuclease"
             /label= r-llaBI (xi) SEQUENCE DESCRIPTION: SEQ ID NO: 9:

```
GAATTCGCAA GGTCTTTTAT AGATATAATT CCTAGCTTAT TTAAACGTTT CTCAGTTCGT      60

TTTCCAATGC CCCAGAAGGC AGTAATCTTG GACTAATGTC AAATAAATAG ACACGAAAAA     120

GTAAATAATA TACCCGAATT GCTAGTTAAT TTCATTGGAA AATAAATAAG TCGTGCTATC     180

CTAATCTTAA ACCACTAAGC ATTAGAAAGC GCACGACTTA TAACACTGAA AAGCTTTCGG     240

TTTCTAGTAT TATGCTCGGT CTTGGAGGTT TGGCAAGCTC TATGTTTGCT ACGCTTCGTG     300

GCGCAAACGA CCTTGTTGGG GGAGTGTTTC ACTTCCCCCG AAACCCCCTT AAAAAACTGT     360

CAAAACGTAG CCGTTTTGTA TTAAAAAAGA TCAGCAGGAG AAGCCCAGCT GATCTTTTTT     420

AATATAGTTC TTCGAACACA ATTCGTTTAT TCATATACTC TTCATAATTT ATATTTAATT     480

GGTATTTTTC AATTAAATAT AAATCAAGCT CTCTTTTAGA ATCGCAATTT TTAATAAAAG     540

TTAATTCGTC TTTTTCAAAA TGTGGAATTG AAAAATTTTT AAGATATTTT TTTTGAAAGC     600

AAAAGTATCC TCCGCCTATC ATATAACTAG TGTTTTCAAT ATAATATTTC ATAATAACTG     660

AGTTCAATAT CTTAGCTAAA ATGTCTAAAT CGATACTTTC TACTGAATTT TTTACTCCAT     720

AAATTGCATA TCCATTATTA AAAGAGCAT AATCTGTAAA ATATACAAAG TTTGGATTCA      780

AAGAATTTGT AGGAAAAATT ATTTTAGGTA CATGGCTATT CAATGCTTGA GATCGCCCAT     840

ATTCATACCA AATGTTAACG GTTGGTTTCC CAGCATTGCG TTTACTGAGC TCGTCTTTAA     900

TAGCAATAAA ATAATTTAAA GTATTAGGGA ATTTTTCCTT CATTGAGACA ATGCTGATTG     960

GTACAGCATT GCCGTTCATA TTTTCATAAG GATATATTAT TCGATTAAAT TCGTAAAAAT    1020

TATTGTTAGT ATTAACTTTT TTTTCTCCAG ATCCTTTAAT AATAGGAATA GTTATTTCTT    1080

TCTCTATGAG AAAAGGTGTG TCATTATACT TTTTCACGAA ATATTCTTTA TCATTATTAA    1140

CTTCTTTTTT AGTATAGTCT ATTAAATAAA GTTTATCTTT TTGAGTAGCA ATACCAGTAG    1200

ATATATTCAG TGTAAAAGGT TGATTTTCTA TTTTATTTAT ATTTAATAAT TCAATTTCAT    1260
```

-continued

```
CTAACAAATT AATAGATTCA GGATTAACAT CATCATACCT AATTTGATCA AACTTGTTTT    1320

TTAATTCTTT TTTCATTGAT ACACTATTAC TATTCGACTG TATATTTTTA TATAATATAT    1380

GACTTTTTTC ACTTTTGTCT AAAAATAATA TAGCAGAATA AGTTTGAGCA TTTGAAAAAA    1440

GTTGATTATC TTTAAAATCT ATTACTTTGT ATATTGATCT AGAATCTACT AAAAGAGCCC    1500

GCAAACCAAA AGCAGATTTC ATTTTTAAAA GGTGATTTGG AACAATATAA CCAATCTTTC    1560

CATTTTCAGA AAGAATATTT AAACTTAATT CTATAAATGC GTAAAATAAA TTATAGCTCC    1620

CAGATTTGCA AGACATATAA TGTTGTTGTA AATACTTTTT TTGATTGGAG GAGAGTTCTT    1680

GTATTTTTAC ATATGGAGGA TTACCGATAA TAAAATCGAT TAAAGAAAGG CTTGGTATTA    1740

TATGTTTAGC ATACTTTAAT GCCGATAGTA GAAATTCGCC ACACCCACAA GAAAAATCAC    1800

CAATGGAGCT TTTTTTATTA ACTGACTTTA AAGTTCTTC AACTATAAAG TCTGAAACTA     1860

GTGAGGGAGT ATATACGATT CCATTTTCTT TCTTTGAGTT CTCACTCAAA CTAGCATATA    1920

AAAATTCTTC AATATTTTA AGAGAAAAAT GAAGCTCATT TTCTTCAATA TAATTTCTTA     1980

TGTCTAAATT TGAGTAGCCT AATAGCTCGT TTATCAAACT ATTTTTAAGG GATTCTATGG    2040

GTATTTTTTT TTCGGTGAAG TAATTTCTTA TTATCTCGCT TAATATTTCT TTGCTTGAAT    2100

ATTTATCGAG TATTTTTTTT ATAAACTCTA TATTTGTTTG TTTATCTATA ACCTCAAGCA    2160

TAATAGCACC TCATTTTTAT TTAATTATAA CTCCTAGGGT TATAAAAGTC AAGTGGAAAG    2220

GAGTAACATT ATGATTATTT TTGTTCTTAA CGAACGGCTA AAAGAACTAA ATATATCACA    2280

AAATAAGTTT GCGAAGCAAT CACATATTAG GCCGATACAA TAAATGATAT CTGCAATAAC    2340

AGTACTAAAA GAATAGAAGT TTCAACTATC AACAAAATAC TAATTCAATT AAATAAGATA    2400

GGTATTCGTA AATACTCTAT TGAAGACATA ATAAAATATA AGCATGAATA AGGAGATTTT    2460

CAT ATG AAT ATA GAT CAA GTT GCA AAT AAA ATG AAA AGG GAT TTA GAA     2508
    Met Asn Ile Asp Gln Val Ala Asn Lys Met Lys Arg Asp Leu Glu
    305             310                 315

CTA GCT ATT ACT GAT CAA ATA GTT GAC GGT TCT AAA GTA AAT AAA AAA     2556
Leu Ala Ile Thr Asp Gln Ile Val Asp Gly Ser Lys Val Asn Lys Lys
320                 325                 330                 335

GGG AAA TTA TTT TTA AAT GGA GCA GAA GCA AAA CAA TCT TTA ATT AGA     2604
Gly Lys Leu Phe Leu Asn Gly Ala Glu Ala Lys Gln Ser Leu Ile Arg
                340                 345                 350

TCT AGT AAA CTT ATT AAT TAT GTT CAC GAG TTT GTA AAA CAT GAA CTA     2652
Ser Ser Lys Leu Ile Asn Tyr Val His Glu Phe Val Lys His Glu Leu
            355                 360                 365

ATA AGA AAT AGT GTT GAA GAA TCT CTG ATA TTC CCC CCA TTA GGT CAG     2700
Ile Arg Asn Ser Val Glu Glu Ser Leu Ile Phe Pro Pro Leu Gly Gln
        370                 375                 380

ACA AAC CCT GAA ATA AAA CTT ACT GGT ATG TTT AAA CAA AAG GAT CAA     2748
Thr Asn Pro Glu Ile Lys Leu Thr Gly Met Phe Lys Gln Lys Asp Gln
    385                 390                 395

GAT GTT TGT GTA AAG CCT CAG GGA GTT TTA CCC GAA AGA ACT TTA ATT     2796
Asp Val Cys Val Lys Pro Gln Gly Val Leu Pro Glu Arg Thr Leu Ile
400                 405                 410                 415

GGA TGG GGA CCT ATG ATA AAT TCG GGA TTA TAC TGT GAT TAT GGT CGC     2844
Gly Trp Gly Pro Met Ile Asn Ser Gly Leu Tyr Cys Asp Tyr Gly Arg
                420                 425                 430

GCT TAT GCA GAA AGA GTA TTA TCT ATC AAT GTA AGA AGT CAA TTA AGT     2892
Ala Tyr Ala Glu Arg Val Leu Ser Ile Asn Val Arg Ser Gln Leu Ser
            435                 440                 445

AGT CTA GAT AAA AAT TCT GAT ACG TTA TTT GAG CGG ATG TTT GCA GAA     2940
Ser Leu Asp Lys Asn Ser Asp Thr Leu Phe Glu Arg Met Phe Ala Glu
```

-continued

```
               450                 455                 460
GCA TTA AAT TTA CAC GAG TTG TAT CCA AAA ATA GTT ATG GGA GAA GTA      2988
Ala Leu Asn Leu His Glu Leu Tyr Pro Lys Ile Val Met Gly Glu Val
        465                 470                 475

TAT GTT ATT CCA GTT TAT GAA TAC GAC GAC CAA GCA ATG ATA AAT AAT      3036
Tyr Val Ile Pro Val Tyr Glu Tyr Asp Asp Gln Ala Met Ile Asn Asn
480                 485                 490                 495

CAA GTT AAG TTC AAG TCA AGA AGA ACA AAT TTA GAA AAA TAC ATT AAT      3084
Gln Val Lys Phe Lys Ser Arg Arg Thr Asn Leu Glu Lys Tyr Ile Asn
                500                 505                 510

TTT TTC TAT TAT TTA AGT GGC AGA GAT GAA CAG GAT CTT GAA GAA GAC      3132
Phe Phe Tyr Tyr Leu Ser Gly Arg Asp Glu Gln Asp Leu Glu Glu Asp
            515                 520                 525

AAA CAA AAG TAC GAA AGG TGC GCA TTG GTT ATA ATA GAT TTT AGA GGA      3180
Lys Gln Lys Tyr Glu Arg Cys Ala Leu Val Ile Ile Asp Phe Arg Gly
        530                 535                 540

GAT CAA GCC AAA GTC TAT AAA AAT ACT GCA GAG TTA AAA GCT AGG GGC      3228
Asp Gln Ala Lys Val Tyr Lys Asn Thr Ala Glu Leu Lys Ala Arg Gly
    545                 550                 555

TTA GTC AGA AAT GAT TTT GAG GTT GAG TTA GCA GAA CTT TCA ACG GAT      3276
Leu Val Arg Asn Asp Phe Glu Val Glu Leu Ala Glu Leu Ser Thr Asp
560                 565                 570                 575

AAA TTT ATT GAA GAC TTA TTA CTT ATT TAT AAT AAT AGA TTT CCT GGT      3324
Lys Phe Ile Glu Asp Leu Leu Leu Ile Tyr Asn Asn Arg Phe Pro Gly
                580                 585                 590

TCT GTT GCG AAG TTT GAA AAT CAA ACG CGC CCT CTC TGAACTCCAA           3370
Ser Val Ala Lys Phe Glu Asn Gln Thr Arg Pro Leu
            595                 600

ATATCTTAGG CTGGTATTCC CATTAATACC TTGATTTCAG TAGACACCGA AAAGCCGAAG    3430

AGAGTTCCAT TCTTCGGTT CTTTTTATAT ATTCCTCGAA TGGTCTGCAT CCCCTTAATC     3490

GTGGAAGAGG CTGTACGGAG ACTTTGATAA AATTTATTCC GTCGTTTAAT AGGTCGATGG    3550

TCTTGTTCTA TTAAATTGTT AAGATACTTC ACAGTTCGGT GCTCTGTCTT AGTATATAAA    3610

CCCACACTCT GTAACTTTCT AAAGCGGAGC CAAGAGAAGG TGCTTTATCG TGCAATTGAT    3670

GCGGACGATC AAAATATTAT TGGGAATACC TGCTTA                              3706
```

(2) INFORMATION FOR SEQ ID NO: 10:

(i) SEQUENCE CHARACTERISTICS:
        (A) LENGTH: 580 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Leu Glu Val Ile Asp Lys Gln Thr Asn Ile Glu Phe Ile Lys Lys
1               5                  10                  15

Ile Leu Asp Lys Tyr Ser Ser Lys Glu Ile Leu Ser Glu Ile Ile Arg
            20                  25                  30

Asn Tyr Phe Thr Glu Lys Lys Ile Pro Ile Glu Ser Leu Lys Asn Ser
        35                  40                  45

Leu Ile Asn Glu Leu Leu Gly Tyr Ser Asn Leu Asp Ile Arg Asn Tyr
    50                  55                  60

Ile Glu Glu Asn Glu Leu His Phe Ser Leu Lys Asn Ile Glu Glu Phe
65                  70                  75                  80

Leu Tyr Ala Ser Leu Ser Glu Asn Ser Lys Lys Glu Asn Gly Ile Val
                85                  90                  95
```

-continued

```
Tyr Thr Pro Ser Leu Val Ser Asp Phe Ile Val Glu Thr Leu Lys
            100                 105                 110

Ser Val Asn Lys Lys Ser Ser Ile Gly Asp Phe Ser Cys Gly Cys Gly
            115                 120                 125

Glu Phe Leu Leu Ser Ala Leu Lys Tyr Ala Lys His Ile Ile Pro Ser
            130                 135                 140

Leu Ser Leu Ile Asp Phe Ile Ile Gly Asn Pro Pro Tyr Val Lys Ile
145                 150                 155                 160

Gln Glu Leu Ser Ser Asn Gln Lys Lys Tyr Leu Gln Gln His Tyr Met
                165                 170                 175

Ser Cys Lys Ser Gly Ser Tyr Asn Leu Phe Tyr Ala Phe Ile Glu Leu
            180                 185                 190

Ser Leu Asn Ile Leu Ser Glu Asn Gly Lys Ile Gly Tyr Ile Val Pro
            195                 200                 205

Asn His Leu Leu Lys Met Lys Ser Ala Phe Gly Leu Arg Ala Leu Leu
            210                 215                 220

Val Asp Ser Arg Ser Ile Tyr Lys Val Ile Asp Phe Lys Asp Asn Gln
225                 230                 235                 240

Leu Phe Ser Asn Ala Gln Thr Tyr Ser Ala Ile Leu Phe Leu Asp Lys
                245                 250                 255

Ser Glu Lys Ser His Ile Leu Tyr Lys Asn Ile Gln Ser Asn Ser Asn
            260                 265                 270

Ser Val Ser Met Lys Lys Glu Leu Lys Asn Lys Phe Asp Gln Ile Arg
            275                 280                 285

Tyr Asp Asp Val Asn Pro Glu Ser Ile Asn Leu Leu Asp Glu Ile Glu
            290                 295                 300

Leu Leu Asn Ile Asn Lys Ile Glu Asn Gln Pro Phe Thr Leu Asn Ile
305                 310                 315                 320

Ser Thr Gly Ile Ala Thr Gln Lys Asp Lys Leu Tyr Leu Ile Asp Tyr
                325                 330                 335

Thr Lys Lys Glu Val Asn Asn Asp Lys Glu Tyr Phe Val Lys Lys Tyr
            340                 345                 350

Asn Asp Thr Pro Phe Leu Ile Glu Lys Glu Ile Thr Ile Pro Ile Ile
            355                 360                 365

Lys Gly Ser Gly Glu Lys Lys Val Asn Thr Asn Asn Asn Phe Tyr Glu
370                 375                 380

Phe Asn Arg Ile Ile Tyr Pro Tyr Glu Asn Met Asn Gly Asn Ala Val
385                 390                 395                 400

Pro Ile Ser Ile Val Ser Met Lys Glu Lys Phe Pro Asn Thr Leu Asn
                405                 410                 415

Tyr Phe Ile Ala Ile Lys Asp Glu Leu Ser Lys Arg Asn Ala Gly Lys
            420                 425                 430

Pro Thr Val Asn Ile Trp Tyr Glu Tyr Gly Arg Ser Gln Ala Leu Asn
            435                 440                 445

Ser His Val Pro Lys Ile Ile Phe Pro Thr Asn Ser Leu Asn Pro Asn
            450                 455                 460

Phe Val Tyr Phe Thr Asp Tyr Ala Leu Phe Asn Asn Gly Tyr Ala Ile
465                 470                 475                 480

Tyr Gly Val Lys Asn Ser Val Glu Ser Ile Asp Leu Asp Ile Leu Ala
                485                 490                 495

Lys Ile Leu Asn Ser Val Ile Met Lys Tyr Tyr Ile Glu Asn Thr Ser
            500                 505                 510
```

```
Tyr Met Ile Gly Gly Gly Tyr Phe Cys Phe Gln Lys Lys Tyr Leu Lys
        515                 520                 525

Asn Phe Ser Ile Pro His Phe Glu Lys Asp Glu Leu Thr Phe Ile Lys
        530                 535                 540

Asn Cys Asp Ser Lys Arg Glu Leu Asp Leu Tyr Leu Ile Glu Lys Tyr
545                 550                 555                 560

Gln Leu Asn Ile Asn Tyr Glu Gly Tyr Met Asn Lys Arg Ile Val Phe
                565                 570                 575

Glu Glu Leu Tyr
            580

(2) INFORMATION FOR SEQ ID NO: 11:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO: 11:

Met Asn Ile Asp Gln Val Ala Asn Lys Met Lys Arg Asp Leu Glu Leu
1               5                   10                  15

Ala Ile Thr Asp Gln Ile Val Asp Gly Ser Lys Val Asn Lys Lys Gly
            20                  25                  30

Lys Leu Phe Leu Asn Gly Ala Glu Ala Lys Gln Ser Leu Ile Arg Ser
        35                  40                  45

Ser Lys Leu Ile Asn Tyr Val His Glu Phe Val Lys His Glu Leu Ile
    50                  55                  60

Arg Asn Ser Val Glu Glu Ser Leu Ile Phe Pro Pro Leu Gly Gln Thr
65                  70                  75                  80

Asn Pro Glu Ile Lys Leu Thr Gly Met Phe Lys Gln Lys Asp Gln Asp
                85                  90                  95

Val Cys Val Lys Pro Gln Gly Val Leu Pro Glu Arg Thr Leu Ile Gly
            100                 105                 110

Trp Gly Pro Met Ile Asn Ser Gly Leu Tyr Cys Asp Tyr Gly Arg Ala
        115                 120                 125

Tyr Ala Glu Arg Val Leu Ser Ile Asn Val Arg Ser Gln Leu Ser Ser
    130                 135                 140

Leu Asp Lys Asn Ser Asp Thr Leu Phe Glu Arg Met Phe Ala Glu Ala
145                 150                 155                 160

Leu Asn Leu His Glu Leu Tyr Pro Lys Ile Val Met Gly Glu Val Tyr
                165                 170                 175

Val Ile Pro Val Tyr Glu Tyr Asp Asp Gln Ala Met Ile Asn Asn Gln
            180                 185                 190

Val Lys Phe Lys Ser Arg Arg Thr Asn Leu Glu Lys Tyr Ile Asn Phe
        195                 200                 205

Phe Tyr Tyr Leu Ser Gly Arg Asp Glu Gln Asp Leu Glu Glu Asp Lys
    210                 215                 220

Gln Lys Tyr Glu Arg Cys Ala Leu Val Ile Ile Asp Phe Arg Gly Asp
225                 230                 235                 240

Gln Ala Lys Val Tyr Lys Asn Thr Ala Glu Leu Lys Ala Arg Gly Leu
                245                 250                 255

Val Arg Asn Asp Phe Glu Val Glu Leu Ala Glu Leu Ser Thr Asp Lys
            260                 265                 270

Phe Ile Glu Asp Leu Leu Leu Ile Tyr Asn Asn Arg Phe Pro Gly Ser
```

```
                275                 280                 285
Val Ala Lys Phe Glu Asn Gln Thr Arg Pro Leu
    290                 295
```

(2) INFORMATION FOR SEQ ID NO: 12:

(i) SEQUENCE CHARACTERISTICS:
        (A) LENGTH: 2355 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Lactococcus lactis subsp. cremoris
        (B) STRAIN: W39

(ix) FEATURE:
        (A) NAME/KEY: CDS
        (B) LOCATION:744..1283
        (C) IDENTIFICATION METHOD: experimental
        (D) OTHER INFORMATION:/codon_start= 744
           /product= "LlaDII restriction endonuclease"
           /evidence= EXPERIMENTAL
           /gene= "ORF"
           /number= 1
           /standard_name= "Gene coding for R.LlaDII"
           /label= r-llaDII
           /note= "The first ten amino acids in this sequence may be
           doubtful. However, from base 773 this reading frame gives
           a high homology with the Bsp6I endonuclease"

(ix) FEATURE:
        (A) NAME/KEY: CDS
        (B) LOCATION:1392..2342
        (C) IDENTIFICATION METHOD: experimental
        (D) OTHER INFORMATION:/codon_start= 1392
           /product= "LlaDII methylase"
           /evidence= EXPERIMENTAL
           /gene= "ORF"
           /number= 2
           /standard_name= "Gene coding for M.LlaDII"
           /label= m-llaDII
           /note= "The sequence shows 60 % identity and 76 %
           similarity with the Bsp6I methylase."

(xi) SEQUENCE DESCRIPTION: SEQ ID NO: 12:

```
CTGCAGAAAA AAAAGTAATT GGTCGTAACG AAACACGATT ATTTTCAGAC GAGCAACTAA      60

ATCACTTATC TATTGAAGTT GAACCTTATC TATTAAAGCA AGGAAATGTA GATATAGAAG     120

AATTAGAAGA ATATCGTCAA AACTTTGAAA ACTATATAGA AGAAGTAAGA AATCAGACAA     180

ATGAAAGTTA TCAGCAACAA CTTGAAGCAG AACAATACGA ACCGCCAAAA GTTACAAAAA     240

GGGAAGCCAT GGAAGTCATG CTGACCGCTC TATTTGAAAA ATTTTTTGAA CCGCTCGACA     300

TTGAGCAATG GAACAAAGAT AAAGCGACAA CTCATTTTTC AGAATTATCA GATATGACTG     360

ATACTGATTA TATACTTGCT TGTATGAGAT TAAACAATCC TACAACTTCA TACACAAAAG     420

AAAATGATAT AATATAGATA AAATTTAGAT ATAAAAGGAA AAACGATTAG AAAGCTTTTC     480

TTTTTTATGT CTAATTATTT GATAATAGTC CACTTTAGCG AGCTTCGCAT TGTTTTAATT     540

GTCTGATAAT TAAGAATTAC AAGGCAACAA CATCTTTTAT AGATATACCA ATTACGCTTT     600

GCAAGCGGAC TGCTTCTGTC GTCAAGCAGA CCAACGAGCA TAAACAAAAA GACTTGCGAC     660

ACTACCTTAT TTCTTTTCTT TAGAAATCTC TATGGATATG ATAAAATTCT ACTTAGGGGA     720
```

```
                                                        -continued

TAAAACAACT CCAAGGTGAT TTA TTG GCT TAT AAA AAG TTT GGC TAT ATT          770
                    Leu Ala Tyr Lys Lys Phe Gly Tyr Ile
                    300                 305

GAA ATT GAT GAT GCC AGA ATA GAT GCA ACT TGT GAT GCT TAC TTT AAA       818
Glu Ile Asp Asp Ala Arg Ile Asp Ala Thr Cys Asp Ala Tyr Phe Lys
    310                 315                 320

TGG AAA GAC CTA AAC TCC TAT ATT AAA AAC ACT AGT TCT CGA GGA ATG       866
Trp Lys Asp Leu Asn Ser Tyr Ile Lys Asn Thr Ser Ser Arg Gly Met
325                 330                 335                 340

AAT ATG CCT GAT GCA ATT AGT GAA CCT ATG GGG TGT TAT TGC TTA GGA       914
Asn Met Pro Asp Ala Ile Ser Glu Pro Met Gly Cys Tyr Cys Leu Gly
                345                 350                 355

TAT CTA TGG AAT AGG GGC AGT GAA GTC GGT GAT GCA ACA GAC CCA ATC       962
Tyr Leu Trp Asn Arg Gly Ser Glu Val Gly Asp Ala Thr Asp Pro Ile
            360                 365                 370

ACA AAT AAA AAA ATT GAG TTT AAG GCA ACA TCA AAG TTT GAA GGG GAT      1010
Thr Asn Lys Lys Ile Glu Phe Lys Ala Thr Ser Lys Phe Glu Gly Asp
            375                 380                 385

TTA TCT TCT TTC GGA CCT AAA ACA GTC TTT GAT AAT TTA GTA TTT CTG      1058
Leu Ser Ser Phe Gly Pro Lys Thr Val Phe Asp Asn Leu Val Phe Leu
        390                 395                 400

AGA TTT TAT CTT GAT GAA AAT AAA TTA TAT ATT TAT GAT TTA AAC ATT      1106
Arg Phe Tyr Leu Asp Glu Asn Lys Leu Tyr Ile Tyr Asp Leu Asn Ile
405                 410                 415                 420

AAT TCA GAA GAG TTT GAG AAA TAT CCA GCA AAT AAG ACT CAA ACT ATA      1154
Asn Ser Glu Glu Phe Glu Lys Tyr Pro Ala Asn Lys Thr Gln Thr Ile
                425                 430                 435

CAA GAA CAA AAA GCT GTT GGA AGG CGT CCT CAC GTG AGT TTA CAA TCT      1202
Gln Glu Gln Lys Ala Val Gly Arg Arg Pro His Val Ser Leu Gln Ser
            440                 445                 450

TTG TTT GTA GAC GCA AAA AAC TTA CAA CCA GAT ATT ATT TTT GAT ATT      1250
Leu Phe Val Asp Ala Lys Asn Leu Gln Pro Asp Ile Ile Phe Asp Ile
        455                 460                 465

AGA CGA TGT CGA ATT ATC GAA GAT AAT AGA CAC TAAACTGAAA GGGGAGTTGT    1303
Arg Arg Cys Arg Ile Ile Glu Asp Asn Arg His
470                 475

TTTATCTCCC TTTTCATCAT ATTAAAATTG CGGCGTGCCG CTTTTTGTTG TATACTATAT    1363

ATCATACTTG ATTTATAGGA GAATATTT ATG TTG AAA ATT GCT TCT TTT TTC       1415
                                Met Leu Lys Ile Ala Ser Phe Phe
                                1               5

GCC GGA GTT GGC GGA ATT GAT TTA GGT TTT GAA AAT GCA GGT TTC AAA      1463
Ala Gly Val Gly Gly Ile Asp Leu Gly Phe Glu Asn Ala Gly Phe Lys
        10                  15                  20

ACA ATA TAT GCT AAT GAA TTT GAT AAT TAT GCT GCT GAT ACT TTT GAA      1511
Thr Ile Tyr Ala Asn Glu Phe Asp Asn Tyr Ala Ala Asp Thr Phe Glu
25                  30                  35                  40

ATG AAC TTT GAC GTT AAG GTA GAC CGA CGT GAT ATA AAT GAT GTA CAA      1559
Met Asn Phe Asp Val Lys Val Asp Arg Arg Asp Ile Asn Asp Val Gln
            45                  50                  55

GCT GAT GAA ATA CCA GAT TTT GAT ATT ATG TTA GCA GGT TTT CCT TGC      1607
Ala Asp Glu Ile Pro Asp Phe Asp Ile Met Leu Ala Gly Phe Pro Cys
        60                  65                  70

CAA GCC TTT TCT ATT GCT GGT TAT CGT CAA GGC TTT AAC GAT GAA CAA      1655
Gln Ala Phe Ser Ile Ala Gly Tyr Arg Gln Gly Phe Asn Asp Glu Gln
    75                  80                  85

GGT CGA GGT AAT CTT TTT TTT GAA CTT GTT CGT ATT TTA GAA ACA AAA      1703
Gly Arg Gly Asn Leu Phe Phe Glu Leu Val Arg Ile Leu Glu Thr Lys
90                  95                  100

AAA CCT CGT GTT GCA TTC TTT GAA AAT GTT AAA AAT CTT GTT TCT CAC      1751
```

```
                                                     -continued

Lys Pro Arg Val Ala Phe Phe Glu Asn Val Lys Asn Leu Val Ser His
105                 110                 115                 120

GAT AGC GGG AAC ACA TTT AGA GTT ATT TGT TCT GAG TTA GAA AGA CTA      1799
Asp Ser Gly Asn Thr Phe Arg Val Ile Cys Ser Glu Leu Glu Arg Leu
                125                 130                 135

GGG TAC AAG TAT CTT TTT CAA GTG TTT AAT GCT TCT GAA TAT GGA AAT      1847
Gly Tyr Lys Tyr Leu Phe Gln Val Phe Asn Ala Ser Glu Tyr Gly Asn
            140                 145                 150

ATA CCT CAA AAT AGA GAA CGT ATC TAT ATT GTT GCT TTC AAA AAT AAA      1895
Ile Pro Gln Asn Arg Glu Arg Ile Tyr Ile Val Ala Phe Lys Asn Lys
        155                 160                 165

AAA GAT TAT GCA AAT TTT GAA CTA CCA AAA TCT ATA CCT TTA AAA ACA      1943
Lys Asp Tyr Ala Asn Phe Glu Leu Pro Lys Ser Ile Pro Leu Lys Thr
    170                 175                 180

ACG ATT CAC GAT GTT ATT GAT TTT TCT AAA AAA CAA GAC GAT AAG TTC      1991
Thr Ile His Asp Val Ile Asp Phe Ser Lys Lys Gln Asp Asp Lys Phe
185                 190                 195                 200

TAC TAT ACC TCT GAA AAG AAT AAA TTT TTT GAT GAG TTA AAA GAA AAT      2039
Tyr Tyr Thr Ser Glu Lys Asn Lys Phe Phe Asp Glu Leu Lys Glu Asn
                205                 210                 215

ATG ACT AAT CAC GAC ACT ACA TAT CAG TGG CGT AGA GTT TAT GTA AGA      2087
Met Thr Asn His Asp Thr Thr Tyr Gln Trp Arg Arg Val Tyr Val Arg
                220                 225                 230

GAA AAC AAA AGT AAT TTA GTA CCA ACA CTA ACG GCT AAT ATG GGA ACA      2135
Glu Asn Lys Ser Asn Leu Val Pro Thr Leu Thr Ala Asn Met Gly Thr
            235                 240                 245

GGT GGG CAT AAT GTG CCT ATA ATC CTT ACA TAT AGC GGA GAT ATT CGT      2183
Gly Gly His Asn Val Pro Ile Ile Leu Thr Tyr Ser Gly Asp Ile Arg
        250                 255                 260

AAA TTA ACA CCA AGA GAA TGC TTT AAC GTT CAA GGT TTC CCA AAA GAA      2231
Lys Leu Thr Pro Arg Glu Cys Phe Asn Val Gln Gly Phe Pro Lys Glu
265                 270                 275                 280

TAT AAA CTT CCA AAC CAA AGT AAT GGG AGA TTA TAT AAA CAA GCA GGA      2279
Tyr Lys Leu Pro Asn Gln Ser Asn Gly Arg Leu Tyr Lys Gln Ala Gly
                285                 290                 295

AAC AGT GTT GTA GTA CCA GTT ATA GAA AGA ATT GCA AAA AAT CTT GCA      2327
Asn Ser Val Val Val Pro Val Ile Glu Arg Ile Ala Lys Asn Leu Ala
                300                 305                 310

GAT ACT ATA GTC GAA TAACTATGAA TTC                                   2355
Asp Thr Ile Val Glu
            315

(2) INFORMATION FOR SEQ ID NO: 13:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 13:

Leu Ala Tyr Lys Lys Phe Gly Tyr Ile Glu Ile Asp Asp Ala Arg Ile
1               5                   10                  15

Asp Ala Thr Cys Asp Ala Tyr Phe Lys Trp Lys Asp Leu Asn Ser Tyr
                20                  25                  30

Ile Lys Asn Thr Ser Ser Arg Gly Met Asn Met Pro Asp Ala Ile Ser
            35                  40                  45

Glu Pro Met Gly Cys Tyr Cys Leu Gly Tyr Leu Trp Asn Arg Gly Ser
        50                  55                  60
```

```
Glu Val Gly Asp Ala Thr Asp Pro Ile Thr Asn Lys Ile Glu Phe
 65                  70                  75                  80

Lys Ala Thr Ser Lys Phe Glu Gly Asp Leu Ser Ser Phe Gly Pro Lys
                 85                  90                  95

Thr Val Phe Asp Asn Leu Val Phe Leu Arg Phe Tyr Leu Asp Glu Asn
            100                 105                 110

Lys Leu Tyr Ile Tyr Asp Leu Asn Ile Asn Ser Glu Glu Phe Glu Lys
                115                 120                 125

Tyr Pro Ala Asn Lys Thr Gln Thr Ile Gln Glu Gln Lys Ala Val Gly
    130                 135                 140

Arg Arg Pro His Val Ser Leu Gln Ser Leu Phe Val Asp Ala Lys Asn
145                 150                 155                 160

Leu Gln Pro Asp Ile Ile Phe Asp Ile Arg Arg Cys Arg Ile Ile Glu
                165                 170                 175

Asp Asn Arg His
        180
```

(2) INFORMATION FOR SEQ ID NO: 14:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Leu Lys Ile Ala Ser Phe Phe Ala Gly Val Gly Gly Ile Asp Leu
  1               5                  10                  15

Gly Phe Glu Asn Ala Gly Phe Lys Thr Ile Tyr Ala Asn Glu Phe Asp
                 20                  25                  30

Asn Tyr Ala Ala Asp Thr Phe Glu Met Asn Phe Asp Val Lys Val Asp
            35                  40                  45

Arg Arg Asp Ile Asn Asp Val Gln Ala Asp Glu Ile Pro Asp Phe Asp
 50                  55                  60

Ile Met Leu Ala Gly Phe Pro Cys Gln Ala Phe Ser Ile Ala Gly Tyr
 65                  70                  75                  80

Arg Gln Gly Phe Asn Asp Glu Gln Gly Arg Gly Asn Leu Phe Phe Glu
                 85                  90                  95

Leu Val Arg Ile Leu Glu Thr Lys Lys Pro Arg Val Ala Phe Phe Glu
            100                 105                 110

Asn Val Lys Asn Leu Val Ser His Asp Ser Gly Asn Thr Phe Arg Val
                115                 120                 125

Ile Cys Ser Glu Leu Glu Arg Leu Gly Tyr Lys Tyr Leu Phe Gln Val
130                 135                 140

Phe Asn Ala Ser Glu Tyr Gly Asn Ile Pro Gln Asn Arg Glu Arg Ile
145                 150                 155                 160

Tyr Ile Val Ala Phe Lys Asn Lys Lys Asp Tyr Ala Asn Phe Glu Leu
                165                 170                 175

Pro Lys Ser Ile Pro Leu Lys Thr Thr Ile His Asp Val Ile Asp Phe
            180                 185                 190

Ser Lys Lys Gln Asp Asp Lys Phe Tyr Tyr Thr Ser Glu Lys Asn Lys
                195                 200                 205

Phe Phe Asp Glu Leu Lys Glu Asn Met Thr Asn His Asp Thr Thr Tyr
210                 215                 220

Gln Trp Arg Arg Val Tyr Val Arg Glu Asn Lys Ser Asn Leu Val Pro
```

-continued

```
                225                 230                 235                 240

Thr Leu Thr Ala Asn Met Gly Thr Gly Gly His Asn Val Pro Ile Ile
                245                 250                 255

Leu Thr Tyr Ser Gly Asp Ile Arg Lys Leu Thr Pro Arg Glu Cys Phe
            260                 265                 270

Asn Val Gln Gly Phe Pro Lys Glu Tyr Lys Leu Pro Asn Gln Ser Asn
        275                 280                 285

Gly Arg Leu Tyr Lys Gln Ala Gly Asn Ser Val Val Val Pro Val Ile
    290                 295                 300

Glu Arg Ile Ala Lys Asn Leu Ala Asp Thr Ile Val Glu
305                 310                 315
```